(12) United States Patent
Matthews et al.

(10) Patent No.: US 8,877,247 B2
(45) Date of Patent: *Nov. 4, 2014

(54) ABUSE-DETERRENT MULTI-LAYER PHARMACEUTICAL COMPOSITION COMPRISING AN OPIOID ANTAGONIST AND AN OPIOID AGONIST

(75) Inventors: Frank Matthews, Edison, NJ (US); Garth Boehm, Westfield, NJ (US); Lijuan Tang, Flemington, NJ (US); Alfred Liang, Edison, NJ (US)

(73) Assignee: Alpharma Pharmaceuticals LLC, Bridgewater, NJ (US)

( * ) Notice: Subject to any disclaimer, the term of this patent is extended or adjusted under 35 U.S.C. 154(b) by 34 days.

This patent is subject to a terminal disclaimer.

(21) Appl. No.: 12/710,016

(22) Filed: Feb. 22, 2010

(65) Prior Publication Data

US 2010/0143483 A1    Jun. 10, 2010

Related U.S. Application Data

(63) Continuation of application No. 12/399,923, filed on Mar. 6, 2009, now Pat. No. 7,682,634, which is a continuation of application No. 11/820,499, filed on Jun. 19, 2007, now Pat. No. 8,158,156.

(60) Provisional application No. 60/814,949, filed on Jun. 19, 2006.

(51) Int. Cl.
| A61K 9/16 | (2006.01) |
| A61K 9/14 | (2006.01) |
| A61K 9/20 | (2006.01) |
| A61K 9/22 | (2006.01) |
| A61K 9/24 | (2006.01) |
| A61P 25/04 | (2006.01) |
| A61K 9/50 | (2006.01) |
| A61K 9/48 | (2006.01) |

(52) U.S. Cl.
CPC ............... *A61K 9/50* (2013.01); *A61K 9/1676* (2013.01); *A61K 9/5078* (2013.01); *A61K 9/4808* (2013.01); *A61K 9/5026* (2013.01); *A61K 9/5073* (2013.01); *A61K 9/16* (2013.01); *A61K 9/167* (2013.01)
USPC ........... 424/490; 424/489; 424/497; 424/494; 424/471; 424/468; 424/465; 514/282

(58) Field of Classification Search
None
See application file for complete search history.

(56) References Cited

U.S. PATENT DOCUMENTS

| 2,770,569 A | 11/1956 | Fromherz et al. |
| 2,945,049 A | 7/1960 | Chang et al. |
| 2,981,641 A | 4/1961 | O'Neill |
| 3,071,509 A | 1/1963 | O'Neill |
| 3,332,950 A | 7/1967 | Blumberg et al. |
| 3,493,657 A | 2/1970 | Lewenstein et al. |
| 3,676,557 A | 7/1972 | Lachman et al. |
| 3,689,574 A | 9/1972 | Engelhart |
| 3,773,955 A | 11/1973 | Pachter et al. |
| 3,845,770 A | 11/1974 | Theeuwes et al. |
| 3,852,058 A | 12/1974 | Huffman |
| 3,860,619 A | 1/1975 | Christensen et al. |
| 3,879,555 A | 4/1975 | Pachter et al. |
| 3,916,889 A | 11/1975 | Russell |
| 3,965,256 A | 6/1976 | Leslie |
| 3,966,940 A | 6/1976 | Pachter et al. |
| 3,971,725 A | 7/1976 | Douglass |
| 3,980,766 A | 9/1976 | Shaw et al. |
| 3,993,073 A | 11/1976 | Zaffaroni |
| 4,008,719 A | 2/1977 | Theeuwes et al. |
| 4,036,228 A | 7/1977 | Theeuwes |
| 4,063,064 A | 12/1977 | Saunders et al. |
| 4,088,864 A | 5/1978 | Theeuwes et al. |
| 4,111,201 A | 9/1978 | Theeuwes |
| 4,111,202 A | 9/1978 | Theeuwes |
| 4,122,084 A | 10/1978 | Douglass |
| 4,176,186 A | 11/1979 | Goldberg |
| 4,237,140 A | 12/1980 | Dudzinski |
| 4,293,539 A | 10/1981 | Ludwig et al. |
| 4,327,725 A | 5/1982 | Cortese et al. |
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |
| 4,457,933 A | 7/1984 | Gordon et al. |
| 4,464,378 A | 8/1984 | Hussain et al. |
| 4,519,801 A | 5/1985 | Edgren |
| 4,573,995 A | 3/1986 | Chen et al. |

(Continued)

FOREIGN PATENT DOCUMENTS

| AU | 9211180 | 9/1992 |
| CA | 2229621 | 9/1998 |

(Continued)

OTHER PUBLICATIONS

Pakkanen, Jukka. S. , University of Helsinki."Upregulation and Functionality of Neuronal Nicotinic Acetylcholine Receptors," Academic Dissertation, 2006.

(Continued)

*Primary Examiner* — Kevin S Orwig

(74) *Attorney, Agent, or Firm* — Stephanie J. Monaco

(57) ABSTRACT

Provided herein is a pharmaceutical composition comprising an antagonist, an agonist, a seal coat, and a sequestering polymer, wherein the antagonist, agonist, seal coat and at least one sequestering polymer are all components of a single unit, and wherein the seal coat forms a layer physically separating the antagonist from the agonist from one another. Methods for manufacturing such a pharmaceutical composition are also provided.

16 Claims, 14 Drawing Sheets

(56) References Cited

U.S. PATENT DOCUMENTS

| | | |
|---|---|---|
| 4,576,604 A | 3/1986 | Guittard et al. |
| 4,582,835 A | 4/1986 | Lewis et al. |
| 4,588,580 A | 5/1986 | Gale et al. |
| 4,597,961 A | 7/1986 | Etscorn |
| 4,606,909 A | 8/1986 | Bechgaard |
| 4,608,376 A | 8/1986 | Pasternak |
| 4,612,008 A | 9/1986 | Wong et al. |
| 4,626,539 A | 12/1986 | Aungst et al. |
| 4,655,766 A | 4/1987 | Theeuwes et al. |
| 4,661,492 A | 4/1987 | Lewis et al. |
| 4,719,215 A | 1/1988 | Goldberg |
| 4,730,048 A | 3/1988 | Portoghese et al. |
| 4,760,069 A | 7/1988 | Rzeszotarski et al. |
| 4,769,372 A | 9/1988 | Kreek et al. |
| 4,783,456 A | 11/1988 | Glassman |
| 4,785,000 A | 11/1988 | Kreek et al. |
| 4,795,327 A | 1/1989 | Gaylord et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,846,199 A | 7/1989 | Rose |
| 4,861,598 A | 8/1989 | Oshlack et al. |
| 4,861,781 A | 8/1989 | Goldberg |
| 4,867,985 A | 9/1989 | Heafield et al. |
| 4,867,987 A | 9/1989 | Seth |
| 4,871,546 A | 10/1989 | Feltz et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,935,429 A | 6/1990 | Dackis et al. |
| 4,940,587 A | 7/1990 | Jenkins et al. |
| 4,954,298 A | 9/1990 | Yamamoto et al. |
| 4,957,681 A | 9/1990 | Klimesch et al. |
| 4,970,075 A | 11/1990 | Oshlack |
| 4,987,136 A | 1/1991 | Kreek et al. |
| 4,990,341 A | 2/1991 | Goldie et al. |
| 4,992,464 A | 2/1991 | Brooks et al. |
| 4,994,279 A | 2/1991 | Aoki et al. |
| 5,021,053 A | 6/1991 | Barclay et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,189,064 A | 2/1993 | Blum et al. |
| 5,198,229 A | 3/1993 | Wong et al. |
| 5,202,128 A | 4/1993 | Morella et al. |
| 5,215,758 A | 6/1993 | Krishnamurthy |
| 5,219,858 A | 6/1993 | Parnell |
| 5,225,440 A | 7/1993 | London et al. |
| 5,226,331 A | 7/1993 | Thompson et al. |
| 5,236,714 A | 8/1993 | Lee et al. |
| 5,256,669 A | 10/1993 | Askanazi et al. |
| 5,266,331 A | 11/1993 | Oshlack et al. |
| 5,266,574 A | 11/1993 | Zagon et al. |
| 5,273,760 A | 12/1993 | Oshlack et al. |
| 5,286,493 A | 2/1994 | Oshlack et al. |
| 5,312,389 A | 5/1994 | Theeuwes et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,326,571 A | 7/1994 | Wright et al. |
| 5,330,766 A | 7/1994 | Morella et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,362,496 A | 11/1994 | Baker et al. |
| 5,376,384 A | 12/1994 | Eichel et al. |
| 5,376,662 A | 12/1994 | Ockert |
| 5,378,474 A | 1/1995 | Morella et al. |
| 5,385,903 A | 1/1995 | Steppuhn et al. |
| 5,403,595 A | 4/1995 | Kitchell et al. |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,451,408 A | 9/1995 | Mezei et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,475,995 A | 12/1995 | Livingston |
| 5,478,573 A | 12/1995 | Eichel et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,507,277 A | 4/1996 | Rubsamen et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,529,787 A | 6/1996 | Merrill et al. |
| 5,529,790 A | 6/1996 | Eichel |
| 5,529,813 A | 6/1996 | Kobsa et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,565,455 A | 10/1996 | Bjork et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,629,011 A | 5/1997 | Illum |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,725,883 A | 3/1998 | Staniforth et al. |
| 5,763,452 A | 6/1998 | Miller et al. |
| 5,767,125 A | 6/1998 | Crain et al. |
| 5,780,057 A | 7/1998 | Conte |
| 5,780,479 A | 7/1998 | Kim |
| 5,800,836 A | 9/1998 | Morella et al. |
| 5,811,126 A | 9/1998 | Krishnamurthy |
| 5,834,024 A | 11/1998 | Heinicke et al. |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Dempulos et al. |
| 5,860,950 A | 1/1999 | Demopulos et al. |
| 5,866,164 A | 2/1999 | Kuczynski et al. |

(56) References Cited

U.S. PATENT DOCUMENTS

| | | |
|---|---|---|
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,919,473 A | 7/1999 | Elkhoury |
| 5,935,975 A | 8/1999 | Rose et al. |
| 5,942,241 A | 8/1999 | Chasin et al. |
| 5,952,005 A | 9/1999 | Olsson et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,954 A | 10/1999 | Foss |
| 5,998,434 A | 12/1999 | Mitch et al. |
| 6,024,982 A | 2/2000 | Oshlack et al. |
| 6,033,687 A | 3/2000 | Heinicke et al. |
| 6,068,855 A | 5/2000 | Leslie et al. |
| 6,077,532 A | 6/2000 | Malkowska et al. |
| 6,077,533 A | 6/2000 | Oshlack et al. |
| 6,103,258 A | 8/2000 | Simon |
| 6,103,261 A | 8/2000 | Chasin et al. |
| 6,103,734 A | 8/2000 | Legarda Ibanez |
| 6,143,322 A | 11/2000 | Sackler et al. |
| 6,143,328 A | 11/2000 | Heafield et al. |
| 6,149,940 A | 11/2000 | Maggi et al. |
| 6,156,343 A | 12/2000 | Morita et al. |
| 6,162,467 A | 12/2000 | Miller et al. |
| 6,194,000 B1 | 2/2001 | Smith et al. |
| 6,197,348 B1 | 3/2001 | Morella et al. |
| 6,210,714 B1 | 4/2001 | Oshlack et al. |
| 6,214,385 B1 | 4/2001 | Heinicke et al. |
| 6,228,863 B1 | 5/2001 | Palermo et al. |
| 6,254,887 B1 | 7/2001 | Miller et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,316,031 B1 | 11/2001 | Oshlack |
| 6,326,027 B1 | 12/2001 | Miller et al. |
| 6,335,033 B2 | 1/2002 | Oshlack et al. |
| 6,375,957 B1 | 4/2002 | Kaiko et al. |
| 6,387,404 B2 | 5/2002 | Oshlack et al. |
| 6,399,096 B1 | 6/2002 | Miller et al. |
| 6,475,494 B2 | 11/2002 | Kaiko et al. |
| 6,495,120 B2 | 12/2002 | McCoy et al. |
| 6,627,635 B2 | 9/2003 | Palermo et al. |
| 6,635,277 B2 | 10/2003 | Sharma et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,765,010 B2 | 7/2004 | Crain et al. |
| 6,865,444 B2 | 3/2005 | Howard |
| 6,872,407 B2 | 3/2005 | Notario et al. |
| 6,878,717 B2 | 4/2005 | DeCorte et al. |
| 6,905,709 B2 | 6/2005 | Oshlack et al. |
| 7,056,532 B1 | 6/2006 | Kabanov et al. |
| 7,067,151 B1 | 6/2006 | Heinicke et al. |
| 7,070,806 B2 | 7/2006 | Oshlack et al. |
| 7,081,255 B2 | 7/2006 | Baert et al. |
| 7,101,574 B1 | 9/2006 | Criere et al. |
| 7,125,561 B2 | 10/2006 | Sackler |
| 7,144,587 B2 | 12/2006 | Oshlack et al. |
| 7,163,696 B2 | 1/2007 | Davis et al. |
| 7,172,767 B2 | 2/2007 | Kaiko et al. |
| 7,202,240 B2 | 4/2007 | Gilkerson et al. |
| 7,241,458 B1 | 7/2007 | Verreck et al. |
| 7,268,138 B2 | 9/2007 | Kalish et al. |
| 7,332,182 B2 | 2/2008 | Sackler |
| 7,338,928 B2 | 3/2008 | Lau et al. |
| 7,384,653 B2 | 6/2008 | Wright, IV et al. |
| 7,402,607 B2 | 7/2008 | Smith et al. |
| 7,419,686 B2 | 9/2008 | Kaiko et al. |
| 7,682,633 B2 | 3/2010 | Matthews et al. |
| 7,682,634 B2 | 3/2010 | Matthews et al. |
| 7,744,924 B2 | 6/2010 | Heinicke |
| 2002/0010127 A1 | 1/2002 | Oshlack et al. |
| 2002/0058673 A1 | 5/2002 | Kaiko et al. |
| 2003/0004177 A1 | 1/2003 | Kao et al. |
| 2003/0026838 A1 | 2/2003 | Farrell |
| 2003/0049317 A1 | 3/2003 | Lindsay |
| 2003/0059397 A1 | 3/2003 | Hughes |
| 2003/0064099 A1 | 4/2003 | Oshlack et al. |
| 2003/0064122 A1 | 4/2003 | Goldberg et al. |
| 2003/0065002 A1 | 4/2003 | Caruso et al. |
| 2003/0068276 A1 | 4/2003 | Hughes et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0073714 A1 | 4/2003 | Breder et al. |
| 2003/0091635 A1 | 5/2003 | Baichwal et al. |
| 2003/0124061 A1 | 7/2003 | Roberts |
| 2003/0124185 A1 | 7/2003 | Oshlack et al. |
| 2003/0143269 A1 | 7/2003 | Oshlack et al. |
| 2003/0157167 A1 | 8/2003 | Kao et al. |
| 2003/0157168 A1 | 8/2003 | Breder et al. |
| 2003/0190362 A1 | 10/2003 | Sackler et al. |
| 2004/0013716 A1 | 1/2004 | Gale et al. |
| 2004/0024004 A1 | 2/2004 | Sherman et al. |
| 2004/0024006 A1 | 2/2004 | Simon |
| 2004/0092542 A1 | 5/2004 | Oshlack et al. |
| 2004/0110781 A1 | 6/2004 | Harmon et al. |
| 2004/0131552 A1 | 7/2004 | Boehm |
| 2004/0176402 A1 | 9/2004 | Oshlack et al. |
| 2004/0180916 A1 | 9/2004 | Levine |
| 2004/0186121 A1 | 9/2004 | Oshlack et al. |
| 2004/0202717 A1 | 10/2004 | Mehta |
| 2004/0241218 A1 | 12/2004 | Tavares et al. |
| 2005/0095291 A1 | 5/2005 | Oshlack et al. |
| 2005/0142203 A1 | 6/2005 | Heinicke |
| 2005/0163856 A1 | 7/2005 | Maloney et al. |
| 2005/0181046 A1 | 8/2005 | Oshlack et al. |
| 2005/0191244 A1 | 9/2005 | Bartholomaus et al. |
| 2005/0192309 A1 | 9/2005 | Palermo et al. |
| 2005/0245557 A1 | 11/2005 | Schoenhard |
| 2006/0039970 A1 | 2/2006 | Oshlack et al. |
| 2006/0099258 A1 | 5/2006 | Heinicke |
| 2006/0099259 A1 | 5/2006 | Heinicke |
| 2006/0104909 A1 | 5/2006 | Vaghefi et al. |
| 2006/0110327 A1 | 5/2006 | Emigh et al. |
| 2006/0159744 A1 | 7/2006 | Alaux et al. |
| 2006/0182801 A1 | 8/2006 | Breder et al. |
| 2006/0182891 A1 | 8/2006 | Usoskin et al. |
| 2006/0198881 A1 | 9/2006 | Howard et al. |
| 2006/0204575 A1 | 9/2006 | Hengsheng et al. |
| 2006/0257460 A1 | 11/2006 | Jansen et al. |
| 2006/0269605 A1 | 11/2006 | Lizio et al. |
| 2007/0014732 A1 | 1/2007 | Sackler |
| 2007/0020339 A1 | 1/2007 | Bear |
| 2007/0042045 A1 | 2/2007 | Lizio et al. |
| 2007/0134329 A1 | 6/2007 | Heinicke |
| 2007/0185145 A1 | 8/2007 | Royds |
| 2007/0196396 A1 | 8/2007 | Pilgaonkar et al. |
| 2007/0243245 A1 | 10/2007 | Heinicke |
| 2007/0243250 A1 | 10/2007 | Heinicke |
| 2007/0243252 A1 | 10/2007 | Heinicke |
| 2008/0069871 A1 | 3/2008 | Vaughn et al. |
| 2008/0069881 A1 | 3/2008 | Caruso et al. |
| 2008/0075768 A1 | 3/2008 | Vaughn et al. |
| 2008/0075770 A1 | 3/2008 | Vaughn et al. |
| 2008/0075771 A1 | 3/2008 | Vaughn et al. |
| 2008/0166405 A1 | 7/2008 | Mehta |
| 2008/0233156 A1 | 9/2008 | Matthews et al. |
| 2008/0233197 A1 | 9/2008 | Matthews et al. |
| 2008/0280975 A1 | 11/2008 | Badul |
| 2008/0306104 A2 | 12/2008 | Oshlack |
| 2008/0318993 A1 | 12/2008 | Ahdieh |
| 2008/0318994 A1 | 12/2008 | Ahdieh |
| 2009/0028942 A1 | 1/2009 | Kandi et al. |
| 2009/0131466 A1 | 5/2009 | Liang et al. |
| 2009/0162450 A1 | 6/2009 | Matthews et al. |
| 2009/0162451 A1 | 6/2009 | Matthews et al. |

(56) References Cited

U.S. PATENT DOCUMENTS

| | | |
|---|---|---|
| 2009/0238869 A1 | 9/2009 | Heinicke |
| 2010/0151014 A1 | 6/2010 | Liang et al. |
| 2010/0152221 A1 | 6/2010 | Liang et al. |
| 2010/0159018 A1 | 6/2010 | Heinicke |

FOREIGN PATENT DOCUMENTS

| | | |
|---|---|---|
| DE | 2222039 | 11/1972 |
| DE | 4325465 A1 | 2/1995 |
| DE | 29719704 U1 | 3/1998 |
| DE | 19651551 | 6/1998 |
| EP | 0074105 | 3/1983 |
| EP | 0144243 A1 | 6/1985 |
| EP | 0185472 A1 | 6/1986 |
| EP | 0193355 A2 | 9/1986 |
| EP | 0220805 A3 | 5/1987 |
| EP | 0232877 A2 | 8/1987 |
| EP | 0205282 | 12/1987 |
| EP | 0319243 A1 | 6/1989 |
| EP | 0352361 | 1/1990 |
| EP | 502642 | 9/1992 |
| EP | 0502642 A1 | 9/1992 |
| EP | 0647448 A1 | 4/1995 |
| EP | 0913152 A1 | 5/1999 |
| EP | 1041987 B1 | 4/2006 |
| GB | 751767 | 7/1956 |
| GB | 769517 | 3/1957 |
| GB | 791644 | 3/1958 |
| GB | 808269 | 1/1959 |
| GB | 2196848 | 10/1987 |
| WO | WO 8303197 | 9/1983 |
| WO | WO 8701282 A2 | 3/1987 |
| WO | WO 9004965 A1 | 5/1990 |
| WO | WO 9406426 A1 | 3/1994 |
| WO | WO 9503804 A1 | 2/1995 |
| WO | WO 9602251 A1 | 2/1996 |
| WO | WO 9732573 | 9/1997 |
| WO | WO 9733566 A2 | 9/1997 |
| WO | WO 9825613 A2 | 6/1998 |
| WO | WO 9835679 A1 | 8/1998 |
| WO | 9930714 A1 | 6/1999 |
| WO | WO 9932119 | 7/1999 |
| WO | WO 9932120 A1 | 7/1999 |
| WO | WO 0001377 A2 | 1/2000 |
| WO | WO 0038649 A1 | 7/2000 |
| WO | WO 0132180 A2 | 5/2001 |
| WO | WO 0137785 A2 | 5/2001 |
| WO | WO 0152851 A1 | 7/2001 |
| WO | WO 0158447 A1 | 8/2001 |
| WO | WO 0158451 | 8/2001 |
| WO | WO 0168080 A2 | 9/2001 |
| WO | WO 0185257 A2 | 11/2001 |
| WO | WO 0193852 A2 | 12/2001 |
| WO | WO 02092059 | 11/2002 |
| WO | WO 2004026256 | 4/2004 |
| WO | WO 2004026283 | 4/2004 |
| WO | WO 2004/091512 | 10/2004 |
| WO | WO 2004093801 | 11/2004 |
| WO | WO 2005018616 | 3/2005 |
| WO | WO 2005055981 | 6/2005 |
| WO | WO 2005081825 | 9/2005 |
| WO | WO 2006130471 | 12/2006 |
| WO | WO 2008/011169 | 1/2008 |
| WO | WO 2009/088673 | 7/2009 |

OTHER PUBLICATIONS

Bodmeier, Roland, et al. "The influence of Buffer Species and Strength of Diltiazem HCl Release from Beads Coated with the Aqueous Cationic Polymer Dispersions, Eudragit RS, RL 30 D," Pharmaceutical Research, 13(1), 52-56, 1996.

Wagner, Karl G. et al "Influence of chloride ion exchange on the permeability and drug release of Eudragit RS 30 D films," Journal of Controlled Release, 82, (2002).

Felton, Linda A., et al. "Influence of Insoluble Excipients on Film Coating Systems," Drug Development and Industrial Pharmacy, 28(3), 225-243 (2002).

Knop, K., et al. "Influence of Surfactants of Different Charge and Concentration on Drug Release from Pellets Coated with an Aqueous Dispersion of Quaternary Acrylic Polymers," S.T.P. Pharma Sciences, 7(6), 507-512 (1997).

Rao, et al., "Effect of Sodium Lauryl Sulfate on the Release of Rifampicin from Guar Gum Matrix", Indiana J. of Pharm. Sci. pp. 404-406 (Sep.-Oct. 2000).

Bloom et al., Clinical Studies with Naloxone/Methadone in a Ratio of 1:20"; 5.sup.th National Conference on Methadone Treatment (1973), p. 1342-1349, vol. 2.

Bigelow et al., "Abuse Liability Assessment . . ."; Dept. of Psychiatry and Behavioral Sciences—The Johns Hopkins University School of Medicine. p. 145-149.

Crabtree et al., "Review of Naltrexone, a long-acting opiate antagonist"; Clinical Pharmacy, (1984) p. 273-280, vol. 3.

Gonzalez et al., "Naltrexone: A Review of its Pharmacodynamic and Pharmacokinetic Properties and Therapeutic . . . " Drugs (1988), p. 192-213., v. 35.

Holmes et al., Anesth. Analg. (1993), p. 1166-73, v. 77.

Goodman et al., Pharmacological Basis of Therapeutics, 3rd Edition, 1965, pp. 274-279.

Gawin, FH. "Chronic Neuropharmacology of Cocaine", Jr. of Clin. Psychiatry, Feb. 1988, p. 11-16. v. 49(2).

Gan et al., "Opioid-Sparing Effects of a Low-Dose Infusion of Naloxone in Patent-Administered Morphine Sulfate," Anesthesiology (1997), 1075-1080, v. 87(5).

Glick et al "Titration of Oral nicotine Intake . . . ". Nature, 1971, p. 207-208, v. 233.

Harris et al. "Protection Againts Disipropyfluorophosphate Intox." Arch. of Pharm. 1984. p. 64-69, v.327.

Harris, LS. Central Neuropunoral Systems, Fed Proceed., Jan.-Feb. 1970, p. 28-32, v. 20:1.

Hawkes et al., "Effect of an enteric-release formulation of naloxone on intestinal transit in volunteers taking codeine"; Aliment Pharm Ther (2001), p. 625-630, vol. 15.

Levine, et al. "Potentiation of Pentazocine Analgesia by Low-dose Naloxone". J. Clin. Invest.,1988, p. 1574-1577, vol. 82.

Hogger et al., "Comparison of tilidine/naloxone, tramadol and bromfenac in experimental pain . . . ", International J. Clin Pharm and Ther (1999), p. 377-385, vol. 37, No. 8.

Hussain et al., "Buccal and oral bioavailability of naloxone and naltrexone in rats"; (1987), p. 127-130, vol. 36.

King et al., "Naltrexone Biotransformation and Incidence of Subjective Side Effects: A Preliminary Study"; Alcoholism: Clin and Exp Res (1997), p. 906-909, vol. 21, No. 5.

Kurland et al., "Naloxone and the Narcotic Abuser: A Controlled Study of Partial Blockade"; Inter. J. of the Addictions (1974), p. 663-672, vol. 9, No. 5.

Martin et al., "Bioavailability Investigation of a New Tilidine/Naloxone Liquid Formulation Compared . . . "; Arzneim.-Forsch./Drug Res. (1999),p. 599-607, vol. 49.

Lehmann et al., "Influence of Naloxone on the Postoperative Analgesic and Respiratory Effects of Buprenorphine"; Eur J. Clin. Pharm. (1988), 343-352, vol. 34.

Jasinski D.R., "Assessment of the Abuse Potentiality of Morhinelike Drugs (Methods Used in Man)"; Drug Addiction (1977) p. 197-258.

Johnson et al., "Buprenorphine and Naloxone for Heroin Dependence"; Substance Use Disorders(2000) p. 519-526.

Suzuki, et al., Morphine conditioned place preference after chronic treatment with naloxone . . . : Research Communications in Substances of Abuse (1991), vol. 12(3), p. 191-131.

Wikler et al., N-Allylnormorphine: Effects of single doses and precipitation of acute . . . N-Allylnormorphine During Narcotic Addiction (1953) p. 8-20.

Vaccarino et al., Pain, 1989, p. 103-109, v. 36.

Yuan et al., Clinical Trials and Therapeutics, (Apr. 1997) 467-475, v. 61.

Zaks et al., "Naloxone Treatment of Opiate Dependence"; JAMA (1971), p. 2108-2110, vol. 215, No. 13.

(56) References Cited

OTHER PUBLICATIONS

Alvarez-Fuentes, et al., "Study of a complexation process between naltrexone and Eudragit..", Int'l Journal of Pharmaceutics 148 (1997) 219-230.
W.K. Asbeck, et al. "Critical Pigment Volume Relationships", Ind. Eng. Chem., 1949, (41), 1470-1475.
Bashaw, et al. "Relative bioavailability of controlled-release oral morphine sulfate . . . ", Int'l Journal of Clincial Pharmacology and Therapeutics, vol. 33, No. 9 1995(524-529).
Bierwagen, et al., "Studies of the Effects of Particle Size Distribution on the Packing Efficiency of Particles", Powder Tech., 10(1974) 111-119.
Bodmeier, et al., "Dry and wet strengths of polymeric films prepared from an aqueous colloidal polymer dispersion, Eudragit RS30D", Int'l Journ. of Pharma., 96(1993) 129-138.
Bodmeier, et al. "Mechanical Properties of Dry and Wet Cellulosic and Acrylic Films Prepared from Aqueous Colloidal Polymer ..", Pharmaceutical Research, vol. 11, No. 6 (1994).
Fernandez-Arevalo, et al., "Water-Insoluble Complexes of Morphine and Carteolol-Eudragit L.A. ..", Supplied by the British Library, p. 158-181.
Knop, "Influence of Buffer Solution Composition on Drug Release from Pellets Coated with Neutral and Quaternary . . . ", Euro. J. Pharm Sci., vol. 4, (1996) pp. 293-300.
Michalson, A.W, "Ion Exchange", Chem. Engineering, Mar. 18, 1963 pp. 163-182.
Pederson, et al., "Dissolution of Hydrocortisone in Human and Simulated Intestinal Fluids" Pharm. Research, vol. 17, No. 2, 2000; pp. 183-189.
Kaufman, et al.,"Narcotic and Narcotic Antagonist pKa's and Partition Coefficients and Their Significance in Clinical Practice", Drug and Alcohol Depend. 1 (1975-76) pp. 103-114.
The Dow Chem. Co., Technical Information,"Dowex Ion Exchange Resins—Using Ion Exchange Resin Selectivity Coefficients", pp. 1-3.
Abdulla, et al., "Axotomy reduces the effect of analgesic opioids yet increases the effect of nociceptin on dorsal root . . . ", J. Neuro Sci 1998, p. 9685-9694, vol. 18.
Alvarez-Fuentes, et al., "Effectiveness of Repeated Administration of a New Oral Naltrexone . . . "; J. Pharm Pharmacol (2001), p. 1201-1205, v. 53.
Alvarez-Fuentes, et al., "Preclinical Study of an Oral Controlled Release Naltrexone Complex in Mice"; J. Pharm Pharmacol (2000), p. 659-663, v. 52.
Barton et al., "Intranasal Administration of Naloxone by Paramedics"; Prehospital Emergency Care (2002), p. 54-58, vol. 6, No. 1.
Baum et al., "The Impact of the Addition of Naloxone on the Use and Abuse of Pentazocine"; Public Health Reports, (1987) p. 426-429. v. 102(4).
Blachly, M.D., "Naloxone in Opiate Addiction"; Current Psychiatric Therapies (1976) p. 209-213.
Bloom et al., Clinical Studies with Naloxone/Methadone in a Ratio of 1:20; 5.sup.th National Conference on Methadone Treatment (1973), p. 1342-1349, vol. 2.
Brennscheidt et al., Pharmacokinetics of Nortilidine and Naloxone . . . , Arzneim.-Forsch/Drug Res. (2000), p. 1015-1022, vol. 50.
Bigelow et al., "Abuse Liability Assessment . . . "; Dept. of Psychiatry and Behavioral Sciences—The Johns Hopkins University School of Medicine. p. 145-149. 1987.
Bromm, et al., "A Sensitive Method to Evaluate Effects of Analgesics in Man"; Meth and Find Exptl Clin Pharmacol, (1983) p. 545-551, v. 5 No. 8.
Bullingham, et al., "Clinical Pharmacokinetics of Narcotic Agonist-Antagonist Drugs"; Clinical Pharm. (1983) p. 332-343, v. 8.
Cherny, N.., "Opioid Analgesics"; Drugs (1996), p. 713-737, v. 51 (5).
Fraser, Albert D., et al., "Clinical Toxicology of Drugs Used in the Treatment of Opiate Dependency"; Clinical Toxicology I, (1990), p. 375-386, vol. 10, No. 2.

Caruso et al., "Methadone and Naloxone in Combination (Naldone. RTM.) for the Treatment of Heroin Addicts"; Bristol Laboratories, p. 1336-1341F.
CRABTREE et al., "Review of Naltrexone, a long-acting opiate antagonist"; Clinical Pharmacy, (1984) p. 273-280, vol. 3.
Crain et al., "Ultra-low concentrations of naloxone selectively antagonize excitatory . . . " Proc. Natl. Acad. Sci (1995), p. 10540-10544, vol. 92.
Czarnecki et al. "The Use of Photography in the Clinical Evaluation of Unequal Pupils." Canad J Ophthal 1979, p. 297-302, v. 14.
Driscoll, P. "Comparitive Toxicity for Mice . . . " Praeventimedizin, 1972, p. 211-213, v. 17 (4).
Gal et al., "Prolonged Blockade of Opioid Effect with Oral Nalmefene"; Clin Pharmacol Ther. (1986) p. 537-542.
Ghodse, et al., "Opioid analgesics and narcotic antagonists"; Side Effects of Drugs (2000), p. 96-113, Annual 23, Ch. 8.
Tai et al., "Naltrexone: An Antagonist Therapy for Heroin Addiction"; NIDA (1997) 5 pages.
Stine et al., "Reduction of Opiate Withdrawal-like Symptoms by Cocaine Abuse during . . . "; Am. J. Drug Alcohol Abuse (1994), p. 445-458, vol. 20, (4).
Stine et al., "Use of Drug Combinations in Treatment of Opioid Withdrawal"; J. of Clinical Psych. (1992), p. 203-209, vol. 12, No. 3.
Suzuki, et al., Morphine conditioned place preference after chronic treatment with naloxone . . . Research Communications in Substances of Abuse (1991), vol. 12(3), p. 191-131.
Tennant et al "Withdrawal From Nicotine Dependence . . . "., NIDA Research Monograph, 1985, p. 291-297, v. 55.
Walsh et al., "Effects of Naltrexone on Response to Intravenous Cocain, Hydromorphone and their Combination in Humans," (1996).
Way et al., "Responsivity to Naloxone during Morphine Dependence"; Annals New York Academy of Sciences, p. 252-261.
Wodak Alex, "Drug Treatment for Opioid Dependence"; Australian Prescriber (2001), p. 4-6, vol. 24, No. 1.
Parwartikar et al., "Naloxone-Methadone Combination for the Treatment of Opiate Dependence"; Missouri Institute of Psychiatry, p. 1350-1354.
Wikler et al., "N-Allylnormorphine: Effects of single doses and precipitation of acute . . . " N-Allylnormorphine During Narcotic Addiction (1953) p. 8-20.
Childs, et al. "Crystal Engineering Approach to Forming Cocrystals of Amine Hydrochlorides With Organic Acids . . . "J.AM.Chem. SOc. 2004, 126 p. 13335-13342.
Fernandez-Arevalo, et al., "Water-Insoluble Complexes of Morphine and Carteolol-Eudragit L.A. . . . ", Supplied by The British Library, p. 158-181.
Gould, "Salt selection for basic drugs", International Journal of Pharmaceutics, 33 (1986) 201-207.
Holgado, et al., "Physical characterization of carteolol: Eudragit L binding interaction", International Journal of Pharmaceutics 114 (1995) p. 13-21.
Judson, et al., "Chapter 1. Uses of Naloxone in the Diagnosis and Treatment of Heroin Addiction", p. 1-13.
Kelly, et al., "Prevalence and characteristics of opioid use in the US adult population", PAIN 138 (2008) p. 507-513.
Lang, et al., "Cardiovascular responses to injections of cholinomimetic drugs into the cerebral ventricles . . . ", Br. J. Pharmac. (1973), 47, p. 196-205.
McGinity, et al., "In Vitro Adsorption of Various Phmarmaceuticals to Montmorillonite", Journal of Pharmaceutical Sciences, vol. 65, Jun. 1976 p. 896-902.
Mendelson, et al. "Buprenorphine and naloxone interactions in opiate-dependent volunteers", Clinical Pharmacology & Therapeutics, (1996) p. 105-114.
Meyer, et al. "A Behavioral Paradigm for the Evaluation of Narcotic Antagonists", Arch. Gen Psychiatry, vol. 33 (1976), pp. 371-377.
Pakkanen, "Upregulation and Functionality of Neuronal Nicotinic Acetylcholine Receptors", Div. of Pharm. and Toxicology Faculty Pharm.Univ. Helsinki, p. 1-89.
Patel, et al. "Nanoclays for Polymer nanocomposites, paints, inks, greases and cosmetics formulations, . . . ", Bull. Mater. Sci., vol. 29, No. 2 (2006) pp. 133-145.

(56) References Cited

OTHER PUBLICATIONS

Peachey, et al. "Assessment of Opioid Dependence with Naloxone", British Journal of Addiction (1988) 83, pp. 193-201.
Sunshine, et al. "Analgesic Efficacy of Pentazocine Versus a Pentazocine-Naloxone Combination Following Oral Administration", The Clinical Journal of Pain (1988) pp. 35-40.
Rogers, et al., Glass Transitions of the Poly-(n-Alkyl Methacrylates), J. Phys. Chem., 1957, 61 (7), pp. 985-991.
Bierwagen et al., "Recent Studies of Particle Packing in Organic Coatings"; Progress in Organic Coatings., 35 (1999) pp. 1-9.
Okhamafe, et al., "Interaction Phenomena in Pharmaceutical Film Coating and Testing Methods" Int. J. Pharmaceutics; vol. 39 (1987) pp. 1-21.
Farris, R.J.; "Prediction of the Viscosity of Multimodal Suspensions from Unimodal Viscosity Data" Trans. Soc. Rheology, vol. 12, No. 2, (1968) pp. 281-301.
Knop, "Influence of Buffer Solution Composition on Drug Release from Pellets Coated with Neutral and Quaternary . . .", Euro. J. Pharm Sci., vol. 4, (1996) pp. 293-300.
Ozturk, et al. "Mechanism of Release from Pellets Coated with an Ethylcellulose Based Film" J. Cont. Release, vol. 14, (1990) pp. 203-213.
Briscoe, B. et al. "Rheology of Solvent-Cast Polymer Films", Journal of Applied Polymer Science, vol. 28 (1983) No. 3, pp. 3827-3848.
Michelson, A.W, "Ion Exchange", Chem. Engineering, Mar. 18, 1963 pp. 163-182.
Hercules Inc., "Physical and Chemical Properties", pp. 1-34.
Dressman J. et al., "Dissolution Testing as a Prognostic Tool for Oral Drug Absorption: . . . " Pharm. Research, 15 (1) pp. 11-22 (1998).
Galia, et al., "Evaluation of Various Dissolution Media for Predicting In Vivo Performance of Class I and II Drugs" Pharm. Research, 15 (5) pp. 698-705 (1998).
Vertzoni, et al., "Dissolution media simulating the intralumenal composition of the small intestine: . . . " J. of Pharmacy and Pharm., vol. 56, 2004; pp. 453-462.
Pederson, et al., " Dissolution of Hydrocortisone in Human and Simulated Intestinal Fluids" Pharm. Research, vol. 17, No. 2, 2000; pp. 183-189.
Powell, et al., "Application of the critical precipitation essay to complex samples: aluminum binding . . . " Chem. Speciation and Bioavailability; vol. 16, No. 3, 2004, pp. 97-104.
Pharm. Coatings Bulletin 102-3, "Influence of Plasticizers on the Dissolution and Physical Properties of Ethyl Cellulose Films and Coated Beads" pp. 1-8 (1995).
Hjartstam, et al. "Effect of Hydroxyl Group Content in Ethyl Cellulose on Permeability in Free Films and Coated Membranes", J. Appl. Polymer Scien., V. 72, pp. 529-535 (1999).
Feller, et al. "Evaluation of Cellulose Ethers for Conservation", The Getty Conserv. Inst., (1990) pp. 1-161.
Rhom GmbH & Co. KG, Specifications and test methods for Eudragit RL 100 and Eudragit RL PO Eudragrit RS 100 and Eudragit RS PO, (Sep. 2004), pp. 1-4.
Lehmann, et al. "Practical Course in Film Coating of Pharmaceutical Dosage Forms with EUDRAGIT", Pharma Polymers (2001) pp. 1-199.
Kaufman, et al.,"Narcotic and Narcotic Antagonist pKa's and Partition Coefficients and Their Significance in Clinical Practice", Drug and Alcohol Depend. 1 (1975-1976) pp. 103-114.
The Dow Chem. Co., Technical Information,"Dowex Ion Exchange Resins—Using Ion Exchange Resin Selectivity Coefficients", pp. 1-3, 2008.
van der Wel,"Moisture in Organic Coatings—a review", Progress in Organic Coatings 37 (1999) pp. 1-14.
Heng, P.W. S., et al., Drug Dev. Ind. Pharm. (2004), 30(2); pp. 213-220.
Non-Pareil Sugar Spheres 2003 Information Sheet, JRS Pharma LP, pp. 1-4, (Mar. 2003).
Goggins et al. "What WOMAC Pain Score Should make a Patient Eligible for a Trial in Knee Osteoarthritis?", The Journal of Rheumatology, Mar. 1, 2005, vol. 32, No. 3, pp. 540-542.

Ferrari, et al. "Serum time course of naltrexone and 6b-naltrexol levels during long term treatment in durg addits", Drug and alcohol Dependence, vol. 52, (1998) pp. 211-220.
Garner-Nix, JAMC, Oct. 28, 2003, 902 and 904 (2 pages).
Mott et al., Cancer Therapy 2, 365-374 (2004) Jan. 2010.
Notification of Certifications of Invalidity and/or Noninfringement for US Patents Nos. 7,682,634; 7,682,634 and 7,815,934 Pursuant to §505*j)(2)(B)(iv) of the Federal Food, Drug, and cosmetic Act dated Aug. 24, 2011, Watson notice to Alpharma Pharmaceuticals, LLC.
Report on the Filing or Determination of an Action Regarding a Patent or Trademark pursuant to 35 USC 290, filed Oct. 6, 2011.
Complaint filed by Pfizer Inc, Alpharma Pharmaceuticals, LLC and King Pharmaceuticals, Inc., dated Oct. 6, 2011.
Heinicke, G., Drug release from cationic polymethacrylate-coating diltiazem particles, Diss. Abstr. Int., B 2007, 68(6).
Heinicke, G., et al., Drug Release from Ammonio-Methacrylate-Coated Diltiazem Particles: Influence of the Reservoir on Membrane Behavior, Pharmaceutical Development and Technology, 2007, p. 473-479, 12(5).
Heinicke, G., et al., The Influence of Surfactants and Additives on Drug Release from a Cationic Eudragit Coated Multiparticulate Diltiazem Formulation, Pharmaceutical Development and Technology, 2007, p. 381-389, 12(4).
Heinicke, G., et al., Ammonio Polymethacrylate-Coated Diltiazem: Drug Release from Single Pellets, Media Dependence and Swelling Behavior, Pharmaceutical Development and Technology, 2007, p. 285-296, 12(3).
Heinicke, G., et al., Assessment of dynamic image analysis as a surrogate dissolution test for a coated multiparticulate product, Pharmaceutical Development and Technology, 2006, p. 403-408, 11(4).
Heinicke, G., et al., The effects of substrate size, surface area, and density on coat thickness of multi-particulate dosage forms, Pharmaceutical Development and Technology, 2005, p. 85-96, 10(1).
Heinicke, G., et al., Particle Size Distributions of Inert Spheres and Pelletized Pharmaceutical Products by Image Analysis, Pharmaceutical Development and Technology, 2004, p. 359-367, 9(4).
Fassihi, R. A., et al., Potential Use of magnesium Stearate and Talc as Dissolution Retardants in the Development of Controlled Drug Delivery Systems, Pharm Ind, 1994, p. 579-583, 56(6).
Fassihi, R., et al., Application of Response Surface Methodology to Design Optimization in Formulation of a Typical Controlled Release System, Drugs made in Germany, 1996, p. 122-126, 39(4).
Schultz, P., et al., A new multiparticulate delayed release system. Part II: Coating formulation and properties of free films, Journal of Controlled Release, 1997, p. 191-199, 47.
Kibbe, A. H. "Talc." Pharmaceutical Excipients. MedicineComplete, Feb. 3, 2009. Web. <http://www.medicinescomplete.com/mc/excipients/current/1001947358.htm?q=talc>.
Knop, K. Influence of buffer solution composition on drug release from pellets coated with neutral and quaternary acrylic polymers and on swelling of free polymer films. Eur J Pharm Sci. 1996; 4:293-300.
Maejima T, et al., Influence of film additives on stabilizing drug release rates from pellets coated with acrylic polymers. Pharm Dev Technol. 2001; 6(2): 211-221.
Wagner, Kg, et al., Influence of chloride ion exchange on the permeability and drug release of Eudragit RS 30D films. J Control Release. 2002; 82: 385-397.
Wagner, Kg, et al. Anion-induced water flux as drug release mechanism through cationic Eudragit RS 30D film coatings. AAPS Journal. 2005; 7(3): E668-E677.
Donbrow et al. Gradation of microcapsule wall porosity by deposition of polymer mixtures (Eudragit RL and Eurdagit RS). Phase Separation of Polymer Mixtures and Effects of External Media and Conditions on Release. J. Microencapsulation. vol. 12, No. 3, pp. 273-285 (1995).
Weinberg et al. Sublingual absorption of selected opioid analgesics. Clin. Pharmacol. Ther. 44:335-340 (1988).
Weinhold et al. Buprenorphine alone and in combination with naloxone in nondependent humans. Drug and Alcohol Dependence, 30:263:274 (1992).
Wells, et al. Effect of Anionic Surfactants on the Release of Clorpheniramine Malate from an Inert, Heterogeneous Matrix. Drug Development and Industrial Pharmacy, 18(2):175-186 (1992).

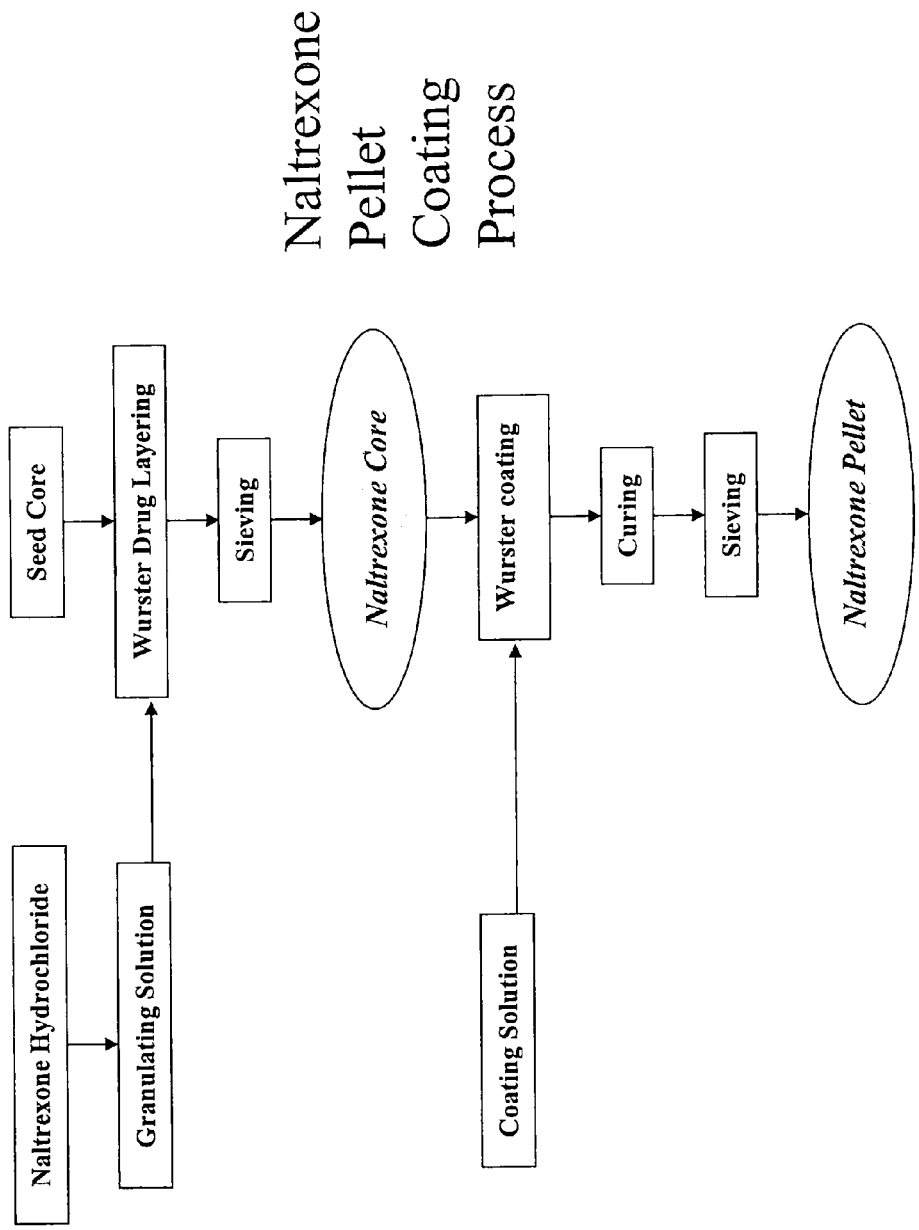
Figure 22A. Manufacturing Process

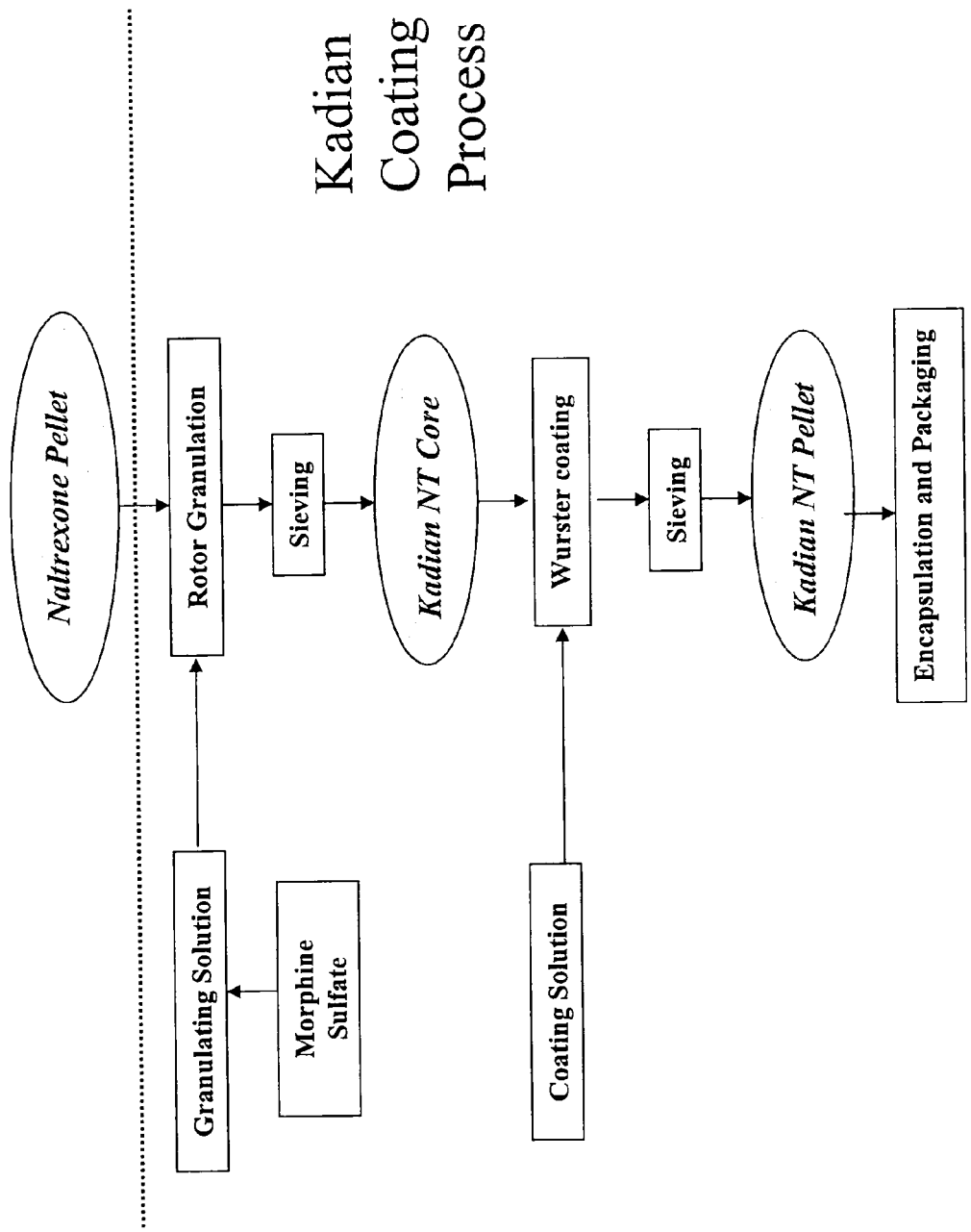
Figure 22B. Manufacturing Process

ABUSE-DETERRENT MULTI-LAYER PHARMACEUTICAL COMPOSITION COMPRISING AN OPIOID ANTAGONIST AND AN OPIOID AGONIST

RELATED APPLICATIONS

This application is a continuation of U.S. Ser. No. 11/820,499, filed on Jun. 19, 2007, which claims priority to U.S. 60/814,949, filed on Jun. 19, 2006.

FIELD OF THE INVENTION

This invention pertains to a sequestering subunit comprising an antagonist and a blocking agent, and related compositions and methods of use, such as in the prevention of abuse of a therapeutic agent.

BACKGROUND OF THE INVENTION

Opioids, also called opioid agonists, are a class of drugs that exhibit opium-like or morphine-like properties. The opioids are employed primarily as moderate to strong analgesics, but have many other pharmacological effects as well, including drowsiness, respiratory depression, changes in mood, and mental clouding without a resulting loss of consciousness. Because of these other pharmacological effects, opioids have become the subject of dependence and abuse. Therefore, a major concern associated with the use of opioids is the diversion of these drugs from the illicit user, e.g., an addict.

Physical dependence may develop upon repeated administrations or extended use of opioids. Physical dependence is gradually manifested after stopping opioid use or is precipitously manifested (e.g., within a few minutes) after administration of a narcotic antagonist (referred to "precipitated withdrawal"). Depending upon the drug upon which dependence has been established and the duration of use and dose, symptoms of withdrawal vary in number and kind, duration and severity. The most common symptoms of the withdrawal syndrome include anorexia, weight loss, pupillary dilation, chills alternating with excessive sweating, abdominal cramps, nausea, vomiting, muscle spasms, hyperirritability, lacrimation, rinorrhea, goose flesh and increased heart rate. Natural abstinence syndromes typically begin to occur 24-48 hours after the last dose, reach maximum intensity about the third day and may not begin to decrease until the third week. Precipitated abstinence syndromes produced by administration of an opioid antagonist vary in intensity and duration with the dose and the specific antagonist, but generally vary from a few minutes to several hours in length.

Psychological dependence or addiction to opioids is characterized by drug-seeking behavior directed toward achieving euphoria and escape from, e.g., psychosocioeconomic pressures. An addict will continue to administer opioids for non-medicinal purposes and in the face of self-harm.

Although opioids, such as morphine, hydromorphone, hydrocodone and oxycodone, are effective in the management of pain, there has been an increase in their abuse by individuals who are psychologically dependent on opioids or who misuse opioids for non-therapeutic reasons. Previous experience with other opioids has demonstrated a decreased abuse potential when opioids are administered in combination with a narcotic antagonist, especially in patients who are ex-addicts (Weinhold et al., *Drug and Alcohol Dependence* 30:263-274 (1992); and Mendelson et al., *Clin. Pharm. Ther.* 60:105-114 (1996)). These combinations, however, do not contain the opioid antagonist that is in a sequestered form. Rather, the opioid antagonist is released in the gastrointestinal system when orally administered and is made available for absorption, relying on the physiology of the host to metabolize differentially the agonist and antagonist and negate the agonist effects.

Previous attempts to control the abuse potential associated with opioid analgesics include, for example, the combination of pentazocine and naloxone in tablets, commercially available in the United States as Talwin®Nx from Sanofi-Winthrop, Canterbury, Australia. Talwin®Nx contains pentazocine hydrochloride equivalent to 50 mg base and naloxone hydrochloride equivalent to 0.5 mg base. Talwin®Nx is indicated for the relief of moderate to severe pain. The amount of naloxone present in this combination has low activity when taken orally, and minimally interferes with the pharmacologic action of pentazocine. However, this amount of naloxone given parenterally has profound antagonistic action to narcotic analgesics. Thus, the inclusion of naloxone is intended to curb a form of misuse of oral pentazocine, which occurs when the dosage form is solubilized and injected. Therefore, this dosage has lower potential for parenteral misuse than previous oral pentazocine formulations. However, it is still subject to patient misuse and abuse by the oral route, for example, by the patient taking multiple doses at once. A fixed combination therapy comprising tilidine (50 mg) and naloxone (4 mg) has been available in Germany for the management of severe pain since 1978 (Valoron®N, Goedecke). The rationale for the combination of these drugs is effective pain relief and the prevention of tilidine addiction through naloxone-induced antagonisms at the tilidine receptors. A fixed combination of buprenorphine and naloxone was introduced in 1991 in New Zealand (Terngesic®Nx, Reckitt & Colman) for the treatment of pain.

International Patent Application No. PCT/US01/04346 (WO 01/58451) to Euroceltique, S.A., describes the use of a pharmaceutical composition that contains a substantially non-releasing opioid antagonist and a releasing opioid agonist as separate subunits that are combined into a pharmaceutical dosage form, e.g., tablet or capsule. However, because the agonist and antagonist are in separate subunits, they can be readily separated. Further, providing the agonist and antagonist as separate subunits, tablets are more difficult to form due to the mechanical sensitivity of some subunits comprising a sequestering agent.

The benefits of the abuse-resistant dosage form are especially great in connection with oral dosage forms of strong opioid agonists (e.g., morphine, hydromorphone, oxycodone or hydrocodone), which provide valuable analgesics but are prone to being abused. This is particularly true for sustained-release opioid agonist products, which have a large dose of a desirable opioid agonist intended to be released over a period of time in each dosage unit. Drug abusers take such sustained release product and crush, grind, extract or otherwise damage the product so that the full contents of the dosage form become available for immediate absorption.

Such abuse-resistant, sustained-release dosage forms have been described in the art (see, for example, U.S. Application Nos. 2003/0124185 and 2003/0044458). However, it is believed that substantial amounts of the opioid antagonist or other antagonist found in these sequestered forms are released over time (usually less than 24 hours) due to the osmotic pressure that builds up in the core of the sequestered form, as water permeates through the sequestered form into the core. The high osmotic pressure inside the core of the sequestered form causes the opioid antagonist or antagonist to be pushed out of the sequestered form, thereby causing the opioid antagonist or antagonist to be released from the sequestered form.

In view of the foregoing drawbacks of the sequestered forms of the prior art, there exists a need in the art for a sequestered form of an opioid antagonist or other antagonist that is not substantially released from the sequestered form due to osmotic pressure. The invention provides such a sequestering form of an opioid antagonist or antagonist. This and other objects and advantages of the invention, as well as additional inventive features, will be apparent from the description of the invention provided herein.

BRIEF SUMMARY OF THE INVENTION

Provided herein is a pharmaceutical composition comprising an antagonist, an agonist, a seal coat, and a sequestering polymer, wherein the antagonist, agonist, seal coat and at least one sequestering polymer are all components of a single unit, and wherein the seal coat forms a layer physically separating the antagonist from the agonist from one another. In one embodiment, a multi-layer pharmaceutical composition comprising an agonist and an antagonist thereof, wherein the agonist and antagonist are not in contact with one another in the intact form of the composition, wherein the agonist is substantially released and the antagonist is substantially sequestered upon administration to a human being is provided. Methods for manufacturing such a pharmaceutical composition are also provided. In another embodiment, a method for measuring the amount of antagonist or derivative thereof in a biological sample, the antagonist or derivative having been released from a pharmaceutical composition in vivo, the method comprising the USP paddle method at 37° C., 100 rpm, but further comprising incubation in a buffer containing a surfactant.

BRIEF DESCRIPTION OF THE DRAWINGS

FIGS. 22 A and B. Exemplary manufacturing process for multi-layer naltrexone-morphine pharmaceutical composition.

DETAILED DESCRIPTION OF THE INVENTION

Figure 1:
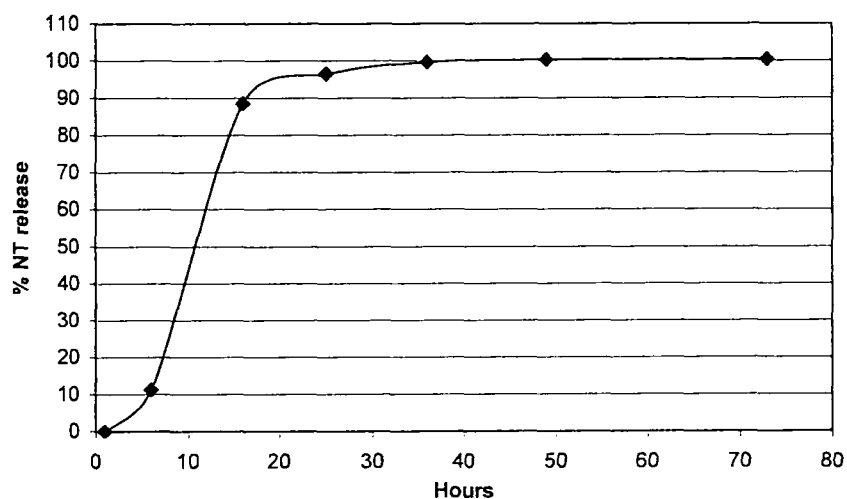
FIG. 1. Naltrexone (NT) release from Eudragit® RS-coated pellets without SLS.

Provided herein are compositions and methods for administering a multiple active agents to a mammal in a form and manner that minimizes the effects of either active agent upon the other in vivo. In certain embodiments, at least two active agents are formulated as part of a pharmaceutical composition. A first active agent may provide a therapeutic effect in vivo. The second active agent may be an antagonist of the first active agent, and may be useful in preventing misuse of the composition. For instance, where the first active agent is a narcotic, the second active agent may be an antagonist of the narcotic. The composition remains intact during normal usage by patients and the antagonist is not released. However, upon tampering with the composition, the antagonist may be released thereby preventing the narcotic from having its intended effect. In certain embodiments, the active agents are both contained within a single unit, such as a bead, in the form of layers. The active agents may be formulated with a substantially impermeable barrier as, for example, a controlled-release composition, such that release of the antagonist from the composition is minimized. In certain embodiments, the antagonist is released in in vitro assays but is substantially not released in vivo. In vitro and in vivo release of the active agent from the composition may be measured by any of several well-known techniques. For instance, in vivo release may be determined by measuring the plasma levels of the active agent or metabolites thereof (i.e., AUC, Cmax).

In one embodiment, the invention provides a sequestering subunit comprising an opioid antagonist and a blocking agent, wherein the blocking agent substantially prevents release of the opioid antagonist from the sequestering subunit in the gastrointestinal tract for a time period that is greater than 24 hours. This sequestering subunit is incorporated into a single pharmaceutical unit that also includes an opioid agonist. The pharmaceutical unit thus includes a core portion to which the opioid antagonist is applied. A seal coat is then optionally applied upon the antagonist. Upon the seal coat is then applied a composition comprising the pharmaceutically active agent. An additional layer containing the same or a different blocking agent may then be applied such that the opioid agonist is released in the digestive tract over time (i.e., controlled release). Thus, the opioid antagonist and the opioid agonist are both contained within a single pharmaceutical unit, which is typically in the form of a bead.

The term "sequestering subunit" as used herein refers to any means for containing an antagonist and preventing or substantially preventing the release thereof in the gastrointestinal tract when intact, i.e., when not tampered with. The term "blocking agent" as used herein refers to the means by which the sequestering subunit is able to prevent substantially the antagonist from being released. The blocking agent may be a sequestering polymer, for instance, as described in greater detail below.

The terms "substantially prevents," "prevents," or any words stemming therefrom, as used herein, means that the antagonist is substantially not released from the sequestering subunit in the gastrointestinal tract. By "substantially not released" is meant that the antagonist may be released in a small amount, but the amount released does not affect or does not significantly affect the analgesic efficacy when the dosage form is orally administered to a host, e.g., a mammal (e.g., a human), as intended. The terms "substantially prevents," "prevents," or any words stemming therefrom, as used herein, does not necessarily imply a complete or 100% prevention. Rather, there are varying degrees of prevention of which one of ordinary skill in the art recognizes as having a potential benefit. In this regard, the blocking agent substantially prevents or prevents the release of the antagonist to the extent that at least about 80% of the antagonist is prevented from being released from the sequestering subunit in the gastrointestinal tract for a time period that is greater than 24 hours. Preferably, the blocking agent prevents release of at least about 90% of the antagonist from the sequestering subunit in the gastrointestinal tract for a time period that is greater than 24 hours. More preferably, the blocking agent prevents release of at least about 95% of the antagonist from the sequestering subunit. Most preferably, the blocking agent prevents release of at least about 99% of the antagonist from the sequestering subunit in the gastrointestinal tract for a time period that is greater than 24 hours.

For purposes of this invention, the amount of the antagonist released after oral administration can be measured in-vitro by dissolution testing as described in the United States Pharmacopeia (USP26) in chapter <711> Dissolution. For example, using 900 mL of 0.1 N HCl, Apparatus 2 (Paddle), 75 rpm, at 37° C. to measure release at various times from the dosage unit. Other methods of measuring the release of an antagonist from a sequestering subunit over a given period of time are known in the art (see, e.g., USP26).

Without being bound to any particular theory, it is believed that the sequestering subunit of the invention overcomes the limitations of the sequestered forms of an antagonist known in the art in that the sequestering subunit of the invention reduces osmotically-driven release of the antagonist from the sequestering subunit. Furthermore, it is believed that the present inventive sequestering subunit reduces the release of the antagonist for a longer period of time (e.g., greater than 24 hours) in comparison to the sequestered forms of antagonists known in the art. The fact that the sequestered subunit of the invention provides a longer prevention of release of the antagonist is particularly relevant, since precipitated withdrawal could occur after the time for which the therapeutic agent is released and acts. It is well known that the gastrointestinal tract transit time for individuals varies greatly within the population. Hence, the residue of the dosage form may be retained in the tract for longer than 24 hours, and in some cases for longer than 48 hours. It is further well known that opioid analgesics cause decreased bowel motility, further prolonging gastrointestinal tract transit time. Currently, sustained-release forms having an effect over a 24 hour time period have been approved by the Food and Drug Administration. In this regard, the present inventive sequestering subunit provides prevention of release of the antagonist for a time period that is greater than 24 hours when the sequestering subunit has not been tampered.

The sequestering subunit of the invention is designed to prevent substantially the release of the antagonist when intact. By "intact" is meant that a dosage form has not undergone tampering. The term "tampering" is meant to include any manipulation by mechanical, thermal and/or chemical means, which changes the physical properties of the dosage form. The tampering can be, for example, crushing, shearing, grinding, chewing, dissolution in a solvent, heating (for example, greater than about 45° C.), or any combination thereof. When the sequestering subunit of the invention has been tampered with, the antagonist is immediately released from the sequestering subunit.

By "subunit" is meant to include a composition, mixture, particle; etc., that can provide a dosage form (e.g., an oral dosage form) when combined with another subunit. The subunit can be in the form of a bead, pellet, granule, spheroid, or the like, and can be combined with additional same or different subunits, in the form of a capsule, tablet or the like, to provide a dosage form, e.g., an oral dosage form. The subunit may also be part of a larger, single unit, forming part of that unit, such as a layer. For instance, the subunit may be a core coated with an antagonist and a seal coat; this subunit may then be coated with additional compositions including a pharmaceutically active agent such as an opioid agonist.

By "antagonist of a therapeutic agent" is meant any drug or molecule, naturally-occurring or synthetic that binds to the same target molecule (e.g., a receptor) of the therapeutic agent, yet does not produce a therapeutic, intracellular, or in vivo response. In this regard, the antagonist of a therapeutic agent binds to the receptor of the therapeutic agent, thereby preventing the therapeutic agent from acting on the receptor. In the case of opioids, an antagonist may prevent the achievement of a "high" in the host.

The antagonist can be any agent that negates the effect of the therapeutic agent or produces an unpleasant or punishing stimulus or effect, which will deter or cause avoidance of tampering with the sequestering subunit or compositions comprising the same. Desirably, the antagonist does not harm a host by its administration or consumption but has properties that deter its administration or consumption, e.g., by chewing and swallowing or by crushing and snorting, for example. The antagonist can have a strong or foul taste or smell, provide a burning or tingling sensation, cause a lachrymation response, nausea, vomiting, or any other unpleasant or repugnant sensation, or color tissue, for example. Preferably, the antagonist is selected from the group consisting of an antagonist of a therapeutic agent, a bittering agent, a dye, a gelling agent, and an irritant. Exemplary antagonists include capsaicin, dye, bittering agents and emetics. The antagonist can comprise a single type of antagonist (e.g., a capsaicin), multiple forms of a single type of antagonist (e.g., a capasin and an analogue thereof), or a combination of different types of antagonists (e.g., one or more bittering agents and one or more gelling agents). Desirably, the amount of antagonist in the sequestering subunit of the invention is not toxic to the host.

In the instance when the therapeutic agent is an opioid agonist, the antagonist preferably is an opioid antagonist, such as naltrexone, naloxone, nalmefene, cyclazacine, levallorphan, derivatives or complexes thereof, pharmaceutically acceptable salts thereof, and combinations thereof. More preferably, the opioid antagonist is naloxone or naltrexone. By "opioid antagonist" is meant to include one or more opioid antagonists, either alone or in combination, and is further meant to include partial antagonists, pharmaceutically acceptable salts thereof, stereoisomers thereof, ethers thereof, esters thereof, and combinations thereof. The pharmaceutically acceptable salts include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like. In certain embodiments, the amount of the opioid antagonist can be about 10 ng to about 275 mg. In a preferred embodiment, when the antagonist is naltrexone, it is preferable that the intact dosage form releases less than 0.125 mg or less within 24 hours, with 0.25 mg or greater of naltrexone released after 1 hour when the dosage form is crushed or chewed.

In a preferred embodiment, the opioid antagonist comprises naloxone. Naloxone is an opioid antagonist, which is almost void of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously in man prevent or promptly reverse the effects of morphine-like opioid agonist. One mg of naloxone intravenously has been reported to block completely the effect of 25 mg of heroin. The effects of naloxone are seen almost immediately after intravenous administration. The drug is absorbed after oral administration, but has been reported to be metabolized into an inactive form rapidly in its first passage through the liver, such that it has been reported to have significantly lower potency than when parenterally administered. Oral dosages of more than 1 g have been reported to be almost completely metabolized in less than 24 hours. It has been reported that 25% of naloxone administered sublingually is absorbed (Weinberg et al., *Clin. Pharmacol. Ther.* 44:335-340 (1988)).

In another preferred embodiment, the opioid antagonist comprises naltrexone. In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located on the nitrogen atom of oxymorphone with a cyclopropylmethyl group. The hydrochloride salt of naltrexone is soluble in water up to about 100 mg/cc. The pharmacological and pharmacokinetic properties of naltrexone have been evaluated in multiple animal and clinical studies. See, e.g., Gonzalez et al. *Drugs* 35:192-213 (1988). Following oral administration, naltrexone is rapidly absorbed (within 1 hour) and has an oral bioavailability ranging from 5-40%. Naltrexone's protein binding is approximately 21% and the volume of distribution following single-dose administration is 16.1 L/kg.

Naltrexone is commercially available in tablet form (Revia®, DuPont (Wilmington, Del.)) for the treatment of alcohol dependence and for the blockade of exogenously administered opioids. See, e.g., Revia (naltrexone hydrochloride tablets), Physician's Desk Reference, 51$^{st}$ ed., Montvale, N.J.; and *Medical Economics* 51:957-959 (1997). A dosage of 50 mg Revia® blocks the pharmacological effects of 25 mg IV administered heroin for up to 24 hours. It is known that, when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with narcotic addicts having good prognosis, as part of a comprehensive occupational or rehabilitative program involving behavioral control or other compliance-enhancing methods. For treatment of narcotic dependence with naltrexone, it is desirable that the patient be opioid-free for at least 7-10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone also has been used for the treatment of alcoholism as an adjunct with social and psychotherapeutic methods. Other preferred opioid antagonists include, for example, cyclazocine and naltrexone, both of which have cyclopropylmethyl substitutions on the nitrogen, retain much of their efficacy by the oral route, and last longer, with durations approaching 24 hours after oral administration.

The antagonist may also be a bittering agent. The term "bittering agent" as used herein' refers to any agent that provides an unpleasant taste to the host upon inhalation and/or swallowing of a tampered dosage form comprising the sequestering subunit. With the inclusion of a bittering agent, the intake of the tampered dosage form produces a bitter taste upon inhalation or oral administration, which, in certain embodiments, spoils or hinders the pleasure of obtaining a high from the tampered dosage form, and preferably prevents the abuse of the dosage form.

Various bittering agents can be employed including, for example, and without limitation, natural, artificial and synthetic flavor oils and flavoring aromatics and/or oils, oleoresins and extracts derived from plants, leaves, flowers, fruits, and so forth, and combinations thereof. Non-limiting representative flavor oils include spearmint oil, peppermint oil, eucalyptus oil, oil of nutmeg, allspice, mace, oil of bitter almonds, menthol and the like. Also useful bittering agents are artificial, natural and synthetic fruit flavors such as citrus oils, including lemon, orange lime, and grapefruit, fruit essences, and so forth. Additional bittering agents include sucrose derivatives (e.g., sucrose octaacetate), chlorosucrose derivatives, quinine sulphate, and the like. A preferred bittering agent for use in the invention is Denatonium Benzoate NF-Anhydrous, sold under the name Bitrex™ (Macfarlan Smith Limited, Edinburgh, UK). A bittering agent can be added to the formulation in an amount of less than about 50% by weight, preferably less than about 10% by weight, more preferably less than about 5% by weight of the dosage form, and most preferably in an amount ranging from about 0.1 to 1.0 percent by weight of the dosage form, depending on the particular bittering agent(s) used.

Alternatively, the antagonist may be a dye. The term "dye" as used herein refers to any agent that causes discoloration of the tissue in contact. In this regard, if the sequestering subunit is tampered with and the contents are snorted, the dye will discolor the nasal tissues and surrounding tissues thereof. Preferred dyes are those that can bind strongly with subcutaneous tissue proteins and are well-known in the art. Dyes useful in applications ranging from, for example, food coloring to tattooing, are exemplary dyes suitable for the invention. Food coloring dyes include, but are not limited to FD&C Green #3 and FD&C Blue #1, as well as any other FD&C or D&C color. Such food dyes are commercially available through companies, such as Voigt Global Distribution (Kansas City, Mo.).

The antagonist may alternatively be an irritant. The term "irritant" as used herein includes a compound used to impart an irritating, e.g., burning or uncomfortable, sensation to an abuser administering a tampered dosage form of the invention. Use of an irritant will discourage an abuser from tampering with the dosage form and thereafter inhaling, injecting, or swallowing the tampered dosage form. Preferably, the irritant is released when the dosage form is tampered with and provides a burning or irritating effect to the abuser upon inhalation, injection, and/or swallowing the tampered dosage form. Various irritants can be employed including, for example, and without limitation, capsaicin, a capsaicin analog with similar type properties as capsaicin, and the like. Some capsaicin analogues or derivatives include, for example, and without limitation, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids. Resiniferatoxin is described, for example, in U.S. Pat. No. 5,290,816. U.S. Pat. No. 4,812,446 describes capsaicin analogs and methods for their preparation. Furthermore, U.S. Pat. No. 4,424,205 cites Newman, "Natural and Synthetic Pepper-Flavored Substances," published in 1954 as listing pungency of capsaicin-like analogs. Ton et al., *British Journal of Pharmacology* 10:175-182 (1955), discusses pharmacological actions of capsaicin and its analogs. With the inclusion of an irritant (e.g., capsaicin) in the dosage form, the irritant imparts a burning or discomforting quality to the abuser to discourage the inhalation, injection, or oral administration of the tampered dosage form, and preferably to prevent the abuse of the dosage form. Suitable capsaicin compositions include capsaicin (trans 8-methyl-N-vanillyl-6-noneamide) or analogues thereof in a concentration between about 0.00125% and 50% by weight, preferably between about 1% and about 7.5% by weight, and most preferably, between about 1% and about 5% by weight.

The antagonist may also be a gelling agent. The term "gelling agent" as used herein refers to any agent that provides a gel-like quality to the tampered dosage form, which slows the absorption of the therapeutic agent, which is formulated with the sequestering subunit, such that a host is less likely to obtain a rapid "high." In certain preferred embodiments, when the dosage form is tampered with and exposed to a small amount (e.g., less than about 10 ml) of an aqueous liquid (e.g., water), the dosage form will be unsuitable for injection and/or inhalation. Upon the addition of the aqueous liquid, the tampered dosage form preferably becomes thick and viscous, rendering it unsuitable for injection. The term "unsuitable for injection" is defined for purposes of the invention to mean that one would have substantial difficulty injecting the dosage form (e.g., due to pain upon administration or difficulty pushing the dosage form through a syringe) due to the viscosity imparted on the dosage form, thereby reducing the potential for abuse of the therapeutic agent in the dosage form. In certain embodiments, the gelling agent is present in such an amount in the dosage form that attempts at evaporation (by the application of heat) to an aqueous mixture of the dosage form in an effort to produce a higher concentration of the therapeutic agent, produces a highly viscous substance unsuitable for injection. When nasally inhaling the tampered dosage form, the gelling agent can become gel-like upon administration to the nasal passages, due to the moisture of the mucous membranes. This also makes such formulations aversive to nasal administration, as the gel will stick to the nasal passage and minimize absorption of the abusable substance. Various gelling agents may can be employed including, for example, and without limitation, sugars or sugar-derived alcohols, such as mannitol, sorbitol, and the like, starch and starch derivatives, cellulose derivatives, such as microcrystalline cellulose, sodium carboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacant, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof; etc. In certain preferred embodiments, the gelling agent is xanthan gum. In other preferred embodiments, the gelling agent of the invention is pectin. The pectin or pectic substances useful for this invention include not only purified or isolated pectates but also crude natural pectin sources, such as apple, citrus or sugar beet residues, which have been subjected, when necessary, to esterification or de-esterification, e.g., by alkali or enzymes. Preferably, the pectins used in this invention are derived from citrus fruits, such as lime, lemon, grapefruit, and orange. With the inclusion of a gelling agent in the dosage form, the gelling agent preferably imparts a gel-like quality to the dosage form upon tampering that spoils or hinders the pleasure of obtaining a rapid high from due to the gel-like consistency of the tampered dosage form in contact with the mucous membrane, and in certain embodiments, prevents the abuse of the dosage form by minimizing absorption, e.g., in the nasal passages. A gelling agent can be added to the formulation in a ratio of gelling agent to opioid agonist of from about 1:40 to about 40:1 by weight, preferably from about 1:1 to about 30:1 by weight, and more preferably from about 2:1 to about 10:1 by weight of the opioid agonist. In certain other embodiments, the dosage form forms a viscous gel having a viscosity of at least about 10 cP after the dosage form is tampered with by dissolution in an aqueous liquid (from about 0.5 to about 10 ml and preferably from 1 to about 5 ml). Most preferably, the resulting mixture will have a viscosity of at least about 60 cP.

The "blocking agent" prevents or substantially prevents the release of the antagonist in the gastrointestinal tract for a time period that is greater than 24 hours, e.g., between 24 and 25 hours, 30 hours, 35 hours, 40 hours, 45 hours, 48 hours, 50 hours, 55 hours, 60 hours, 65 hours, 70 hours, 72 hours, 75 hours, 80 hours, 85 hours, 90 hours, 95 hours, or 100 hours; etc. Preferably, the time period for which the release of the antagonist is prevented or substantially prevented in the gastrointestinal tract is at least about 48 hours. More preferably, the blocking agent prevents or substantially prevents the release for a time period of at least about 72 hours.

The blocking agent of the present inventive sequestering subunit can be a system comprising a first antagonist-impermeable material and a core. By "antagonist-impermeable material" is meant any material that is substantially impermeable to the antagonist, such that the antagonist is substantially not released from the sequestering subunit. The term "substantially impermeable" as used herein does not necessarily imply complete or 100% impermeability. Rather, there are varying degrees of impermeability of which one of ordinary skill in the art recognizes as having a potential benefit. In this regard, the antagonist-impermeable material substantially prevents or prevents the release of the antagonist to an extent that at least about 80% of the antagonist is prevented from being released from the sequestering subunit in the gastrointestinal tract for a time period that is greater than 24 hours. Preferably, the antagonist-impermeable material prevents release of at least about 90% of the antagonist from the sequestering subunit in the gastrointestinal tract for a time period that is greater than 24 hours. More preferably, the antagonist-impermeable material prevents release of at least about 95% of the antagonist from the sequestering subunit. Most preferably, the antagonist-impermeable material prevents release of at least about 99% of the antagonist from the sequestering subunit in the gastrointestinal tract for a time period that is greater than 24 hours. The antagonist-impermeable material prevents or substantially prevents the release of the antagonist in the gastrointestinal tract for a time period that is greater than 24 hours, and desirably, at least about 48 hours. More desirably, the antagonist-impermeable material prevents or substantially prevents the release of the adverse agent from the sequestering subunit for a time period of at least about 72 hours.

Preferably, the first antagonist-impermeable material comprises a hydrophobic material, such that the antagonist is not released or substantially not released during its transit through the gastrointestinal tract when administered orally as intended, without having been tampered with. Suitable hydrophobic materials for use in the invention are described herein and set forth below. The hydrophobic material is preferably a pharmaceutically acceptable hydrophobic material.

It is also preferred that the first antagonist-impermeable material comprises a polymer insoluble in the gastrointestinal tract. One of ordinary skill in the art appreciates that a polymer that is insoluble in the gastrointestinal tract will prevent the release of the antagonist upon ingestion of the sequestering subunit. The polymer may be a cellulose or an acrylic polymer. Desirably, the cellulose is selected from the group consisting of ethylcellulose, cellulose acetate, cellulose propionate, cellulose acetate propionate, cellulose acetate butyrate, cellulose acetate phthalate, cellulose triacetate, and combinations thereof. Ethylcellulose includes, for example, one that has an ethoxy content of about 44 to about 55%. Ethylcellulose can be used in the form of an aqueous dispersion, an alcoholic solution, or a solution in other suitable solvents. The cellulose can have a degree of substitution (D.S.) on the anhydroglucose unit, from greater than zero and up to 3 inclusive. By "degree of substitution" is meant the average number of hydroxyl groups on the anhydroglucose unit of the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, monocellulose alkanylate, dicellulose alkanylate, tricellulose alkanylate, monocellulose alkenylates, dicellulose alkenylates, tricellulose alkenylates, monocellulose aroylates, dicellulose aroylates, and tricellulose aroylates.

More specific celluloses include cellulose propionate having a D.S. of 1.8 and a propyl content of 39.2 to 45 and a hydroxy content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxy content of 0.5 to 4.7%; cellulose triacylate having a D.S. of 2.9 to 3, such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6, such as cellulose disuccinate, cellulose dipalmitate, cellulose dioctanoate, cellulose dipentanoate, and coesters of cellulose, such as cellulose acetate butyrate, cellulose acetate octanoate butyrate, and cellulose acetate propionate.

Additional cellulose polymers that may be used to prepare the sequestering subunit include acetaldehyde dimethyl cellulose acetate, cellulose acetate ethylcarbamate, cellulose acetate methycarbamate, and cellulose acetate dimethylaminocellulose acetate.

The acrylic polymer preferably is selected from the group consisting of methacrylic polymers, acrylic acid and methacrylic acid copolymers, methyl methacrylate copolymers, ethoxyethyl methacrylates, cyanoethyl methacrylate, poly (acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride), glycidyl methacrylate copolymers, and combinations thereof. An acrylic polymer useful for preparation of a sequestering subunit of the invention includes acrylic resins comprising copolymers synthesized from acrylic and methacrylic acid esters (e.g., the copolymer of acrylic acid lower alkyl ester and methacrylic acid lower alkyl ester) containing about 0.02 to about 0.03 mole of a tri (lower alkyl) ammonium group per mole of the acrylic and methacrylic monomer used. An example of a suitable acrylic resin is ammonio methacrylate copolymer NF21, a polymer manufactured by Rohm Pharma GmbH, Darmstadt, Germany, and sold under the Eudragit® trademark. Eudragit® is a water-insoluble copolymer of ethyl acrylate (EA), methyl methacrylate (MM) and trimethylammoniumethyl methacrylate chloride (TAM) in which the molar ratio of TAM to the remaining components (EA and MM) is 1:40. Acrylic resins, such as Eudragit®, can be used in the form of an aqueous dispersion or as a solution in suitable solvents. Preferred acrylic polymers include copolymers of acrylic and methacrylic acid esters with a low content in quaternary ammonium groups such as Eudragit® RL PO (Type A) and Eudragit® RS PO (Type B; as used herein, "Eudragit® RS") (as described the monographs Ammonia Methacrylate Copolymer Type A Ph. Eur., Ammonio Methacrylate Copolymer Type B Ph. Eur., Ammonio Methacrylate Copolymer, Type A and B USP/NF, and Aminoalkylmethacrylate Copolymer RS JPE).

In another preferred embodiment, the antagonist-impermeable material is selected from the group consisting of polylactic acid, polyglycolic acid, a co-polymer of polylactic acid and polyglycolic acid, and combinations thereof. In certain other embodiments, the hydrophobic material includes a biodegradable polymer comprising a poly(lactic/glycolic acid) ("PLGA"), a polylactide, a polyglycolide, a polyanhydride, a polyorthoester, polycaprolactones, polyphosphazenes, polysaccharides, proteinaceous polymers, polyesters, polydioxanone, polygluconate, polylactic-acid-polyethylene oxide copolymers, poly(hydroxybutyrate), polyphosphoester or combinations thereof. Preferably, the biodegradable polymer comprises a poly(lactic/glycolic acid), a copolymer of lactic and glycolic acid, having a molecular weight of about 2,000 to about 500,000 daltons. The ratio of lactic acid to glycolic acid is preferably from about 100:1 to about 25:75, with the ratio of lactic acid to glycolic acid of about 65:35 being more preferred.

Poly(lactic/glycolic acid) can be prepared by the procedures set forth in U.S. Pat. No. 4,293,539 (Ludwig et al.), which is incorporated herein by reference. In brief, Ludwig prepares the copolymer by condensation of lactic acid and glycolic acid in the presence of a readily removable polymerization catalyst (e.g., a strong ion-exchange resin such as Dowex HCR-W2-H). The amount of catalyst is not critical to the polymerization, but typically is from about 0.01 to about 20 parts by weight relative to the total weight of combined lactic acid and glycolic acid. The polymerization reaction can be conducted without solvents at a temperature from about 100° C. to about 250° C. for about 48 to about 96 hours, preferably under a reduced pressure to facilitate removal of water and by-products. Polylactic/glycolic acid) is then recovered by filtering the molten reaction mixture in an organic solvent, such as dichloromethane or acetone, and then filtering to remove the catalyst.

Suitable plasticizers for use in the sequestering subunit include, for example, acetyl triethyl citrate, acetyl tributyl citrate, triethyl citrate, diethyl phthalate, dibutyl phthalate (DBP), acetyltri-N-butyl citrate (ATBC), or dibutyl sebacate, which can be admixed with the polymer. Other additives such as coloring agents may also be used in making the present inventive sequestering subunit.

In certain embodiments, additives may be included in the compositions the improve the sequestering characteristics of the sequestering subunit. As described below, the ratio of additives or components with respect to other additives or components may be modified to enhance or delay improve sequestration of the agent contained within the subunit. Various amounts of a functional additive (i.e., a charge-neutralizing additive), may be included to vary the release of an antagonist, particularly where a water-soluble core (i.e., a sugar sphere) is utilized. For instance, it has been determined that the inclusion of a low amount of charge-neutralizing additive relative to sequestering polymer on a weight-by-weight basis may cause decreased release of the antagonist.

In certain embodiments, a surfactant may serve as a charge-neutralizing additive. Such neutralization may in certain embodiments reduce the swelling of the sequestering polymer by hydration of positively charged groups contained therein. Surfactants (ionic or non-ionic) may also be used in preparing the sequestering subunit. It is preferred that the surfactant be ionic. Suitable exemplary agents include, for example, alkylaryl sulphonates, alcohol sulphates, sulphosuccinates, sulphosuccinamates, sarcosinates or taurates and others. Additional examples include but are not limited to ethoxylated castor oil, benzalkonium chloride, polyglycolyzed glycerides, acetylated monoglycerides, sorbitan fatty acid esters, poloxamers, polyoxyethylene fatty acid esters, polyoxyethylene derivatives, monoglycerides or ethoxylated derivatives thereof, diglycerides or polyoxyethylene derivatives thereof, sodium docusate, sodium lauryl sulfate, dioctyl sodium sulphosuccinate, sodium lauryl sarcosinate and sodium methyl cocoyl taurate, magnesium lauryl sulfate, triethanolamine, cetrimide, sucrose laurate and other sucrose esters, glucose (dextrose) esters, simethicone, ocoxynol, dioctyl sodiumsulfosuceinate, polyglycolyzed glycerides, sodiumdodecylbenzene sulfonate, dialkyl sodiumsulfosuccinate, fatty alcohols such as lauryl, cetyl, and steryl, glycerylesters, cholic acid or derivatives thereof, lecithins, and phospholipids. These agents are typically characterized as ionic (i.e., anionic or cationic) or nonionic. In certain embodiments described herein, an anionic surfactant such as sodium lauryl sulfate (SLS) is preferably used (U.S. Pat. Nos. 5,725,883; 7,201,920; EP 502642A1; Shokri, et al. Pharm. Sci. 2003. *The effect of sodium lauryl sulphate on the release of diazepam from solid dispersions prepared by cogrinding technique*. Wells, et al. *Effect of Anionic Surfactants on the Release of Chlorpheniramine Maleate From an Inert, Heterogeneous Matrix*. Drug Development and Industrial Pharmacy 18(2) (1992): 175-186. Rao, et al. "Effect of Sodium Lauryl Sulfate on the Release of Rifampicin from Guar Gum Matrix." Indian Journal of Pharmaceutical Science (2000): 404-406; Knop, et al. *Influence of surfactants of different charge and concentration on drug release from pellets coated with an aqueous dispersion of quaternary acrylic polymers*. STP Pharma Sciences, Vol. 7, No. 6, (1997) 507-512). Other suitable agents are known in the art.

As shown herein, SLS is particularly useful in combination with Eudragit RS when the sequestering subunit is built upon a sugar sphere substrate. The inclusion of SLS at less than approximately 6.3% on a weight-to-weight basis relative to the sequestering polymer (i.e., Eudragit RS) may provide a charge neutralizing function (theoretically 20% and 41% neutralization, respectfully), and thereby significantly slow the release of the active agent encapsulated thereby (i.e., the antagonist naltrexone). Inclusion of more than approximately 6.3% SLS relative to the sequestering polymer appears to increase release of the antagonist from the sequestering subunit. With respect to SLS used in conjunction with Eudragit® RS, it is preferred that the SLS is present at approximately 1%, 2%, 3%, 4% or 5%, and typically less than 6% on a w/w basis relative to the sequestering polymer (i.e., Eudragit® RS). In preferred embodiments, SLS may be present at approximately 1.6% or approximately 3.3% relative to the sequestering polymer. As discussed above, many agents (i.e., surfactants) may substitute for SLS in the compositions disclosed herein.

Additionally useful agents include those that may physically block migration of the antagonist from the subunit and/or enhance the hydrophobicity of the barrier. One exemplary agent is talc, which is commonly used in pharmaceutical compositions (Pawar et al. *Agglomeration of Ibuprofen With Talc by Novel Crystallo-Co-Agglomeration Technique*. AAPS PharmSciTech. 2004; 5(4): article 55). As shown in the Examples, talc is especially useful where the sequestering subunit is built upon a sugar sphere core. Any form of talc may be used, so long as it does not detrimentally affect the function of the composition. Most talc results from the alteration of dolomite ($CaMg(CO_3)_2$ or magnesite (MgO) in the presence of excess dissolved silica ($SiO_2$) or by altering serpentine or quartzite. Talc may be include minerals such as tremolite ($CaMg_3(SiO_3)_4$), serpentine ($3MgO.2SiO_2.2H_2O$), anthophyllite ($Mg_7.(OH)_2.(Si_4O_{11})_2$), magnesite, mica, chlorite, dolomite, the calcite form of calcium carbonate ($CaCO_3$), iron oxide, carbon, quartz, and/or manganese oxide. The presence of such impurities may be acceptable in the compositions described herein provided the function of the talc is maintained. It is preferred that that talc be USP grade. As mentioned above, the function of talc as described herein is to enhance the hydrophobicity and therefore the functionality of the sequestering polymer. Many substitutes for talc may be utilized in the compositions described herein as may be determined by one of skill in the art.

It has been determined that the ratio of talc to sequestering polymer may make a dramatic difference in the functionality of the compositions described herein. For instance, the Examples described below demonstrate that the talc to sequestering polymer ratio (w/w) is important with respect to compositions designed to prevent the release of naltrexone therefrom. It is shown therein that inclusion of an approximately equivalent amount (on a weight-by-weight basis) of talc and Eudragit® RS results in a very low naltrexone release profile. In contrast, significantly lower or higher both a lower (69% w/w) and a higher (151% w/w) talc:Eudragit® RS ratios result in increased release of naltrexone release. Thus, where talc and Eudragit® RS are utilized, it is preferred that talc is present at approximately 75%, 80%, 85%, 90%, 95%, 100%, 105%, 110%, 115%, 120% or 125% w/w relative to Eudragit® RS. As described above, the most beneficial ratio for other additives or components will vary and may be determined using standard experimental procedures.

In certain embodiments, such as where a water-soluble core is utilized, it is useful to include agents that may affect the osmotic pressure of the composition (i.e., an osmotic pressure regulating agent) (see, in general, WO 2005/046561 A2 and WO 2005/046649 A2 relating to Eudramode®). This agent is preferably applied to the Eudragit® RS/talc layer described above. In a pharmaceutical unit comprising a sequestering subunit overlayed by an active agent (i.e., a controlled-release agonist preparation), the osmotic pressure regulating agent is preferably positioned immediately beneath the active agent layer. Suitable osmotic pressure regulating agents may include, for instance, hydroxypropyl-methyl cellulose (HPMC) or chloride ions (i.e., from NaCl), or a combination of HPMC and chloride ions (i.e., from NaCl). Other ions that may be useful include bromide or iodide. The combination of sodium chloride and HPMC may be prepared in water or in a mixture of ethanol and water, for instance. HPMC is commonly utilized in pharmaceutical compositions (see, for example, U.S. Pat. Nos. 7,226,620 and 7,229,982). In certain embodiments, HPMC may have a molecular weight ranging from about 10,000 to about 1,500,000, and typically from about 5000 to about 10,000 (low molecular weight HPMC). The specific gravity of HPMC is typically from about 1.19 to about 1.31, with an average specific gravity of about 1.26 and a viscosity of about 3600 to 5600. HPMC may be a water-soluble synthetic polymer. Examples of suitable, commercially available hydroxypropyl methylcellulose polymers include Methocel K100 LV and Methocel K4M (Dow). Other HPMC additives are known in the art and may be suitable in preparing the compositions described herein. As shown in the Examples, the inclusion of NaCl (with HPMC) was found to have positively affect sequestration of naltrexone by Eudragit® RS. In certain embodiments, it is preferred that the charge-neutralizing additive (i.e., NaCl) is included at less than approximately 1, 2, 3, 4, 5, 6, 7, 8, 9, or 10% on a weight-by-weight basis with respect to the sequestering polymer. In other preferred embodiments, the charge-neutralizing additive is present at approximately 4% on a weight-by-weight basis with respect to the sequestering polymer.

Thus, in one embodiment, a sequestering subunit built upon a sugar sphere substrate is provided comprising a sequestering polymer (i.e., Eudragit® RS) in combination with several optimizing agents, including sodium lauryl sulfate (SLS) as a charge-neutralizing agent to reduce swelling of the film by hydration of the positively charged groups on the polymer; talc to create a solid impermeable obstacle to naltrexone transport through the film and as a hydrophobicity-enhancing agent; and a chloride ion (i.e., as NaCl) as an osmotic pressure reducing agent. The ratio of each of the additional ingredients relative to the sequestering polymer was surprisingly found to be important to the function of the sequestering subunit. For instance, the Examples provide a sequestering subunit including a sequestering polymer and the optimizing agents SLS at less than 6%, preferably 1-4%, and even more preferably 1.6% or 3.3% on a w/w basis relative to Eudragit RS; talc in an amount approximately equal to Eudragit® RS (on a w/w basis); and, NaCl present at approximately 4% on a w/w basis relative to Eudragit® RS.

Methods of making any of the sequestering subunits of the invention are known in the art. See, for example, *Remington: The Science and Practice of Pharmacy*, Alfonso R. Genaro (ed), 20$^{th}$ edition, and Example 2 set forth below. The sequestering subunits can be prepared by any suitable method to provide, for example, beads, pellets, granules, spheroids, and the like. Spheroids or beads, coated with an active ingredient can be prepared, for example, by dissolving the active ingredient in water and then spraying the solution onto a substrate, for example, nu pariel 18/20 beads, using a Wurster insert. Optionally, additional ingredients are also added prior to coating the beads in order to assist the active ingredient in binding to the substrates, and/or to color the solution; etc. The resulting substrate-active material optionally can be over-coated with a barrier material to separate the therapeutically active agent from the next coat of material, e.g., release-retarding or sequestering material. Preferably, the barrier material is a material comprising hydroxypropyl methylcellulose. However, any film-former known in the art can be used. Preferably, the barrier material does not affect the dissolution rate of the final product.

Pellets comprising an active ingredient can be prepared, for example, by a melt pelletization technique. Typical of such techniques is when the active ingredient in finely divided form is combined with a binder (also in particulate form) and other optional inert ingredients, and thereafter the mixture is pelletized, e.g., by mechanically working the mixture in a high shear mixer to form the pellets (e.g., pellets, granules, spheres, beads; etc., collectively referred to herein as "pellets"). Thereafter, the pellets can be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

The diameter of the extruder aperture or exit port also can be adjusted to vary the thickness of the extruded strands. Furthermore, the exit part of the extruder need not be round; it can be oblong, rectangular; etc. The exiting strands can be reduced to particles using a hot wire cutter, guillotine; etc.

The melt-extruded multiparticulate system can be, for example, in the form of granules, spheroids, pellets, or the like, depending upon the extruder exit orifice. The terms "melt-extruded multiparticulate(s)" and "melt-extruded multiparticulate system(s)" and "melt-extruded particles" are used interchangeably herein and include a plurality of subunits, preferably within a range of similar size and/or shape. The melt-extruded multiparticulates are preferably in a range of from about 0.1 to about 12 mm in length and have a diameter of from about 0.1 to about 5 mm. In addition, the melt-extruded multiparticulates can be any geometrical shape within this size range. Alternatively, the extrudate can simply be cut into desired lengths and divided into unit doses of the therapeutically active agent without the need of a spheronization step.

The substrate also can be prepared via a granulation technique. Generally, melt-granulation techniques involve melting a normally solid hydrophobic material, e.g., a wax, and incorporating an active ingredient therein. To obtain a sustained-release dosage form, it can be necessary to incorporate an additional hydrophobic material.

A coating composition can be applied onto a substrate by spraying it onto the substrate using any suitable spray equipment. For example, a Wurster fluidized-bed system can be used in which an air flow from underneath, fluidizes the coated material and effects drying, while the insoluble polymer coating is sprayed on. The thickness of the coating will depend on the characteristics of the particular coating composition, and can be determined by using routine experimentation.

Any manner of preparing a subunit can be employed. By way of example, a subunit in the form of a pellet or the like can be prepared by co-extruding a material comprising the opioid agonist and a material comprising the opioid antagonist and/ or antagonist in sequestered form. Optionally, the opioid antagonist composition can cover, e.g., overcoat, the material comprising the antagonist and/or antagonist in sequestered form. A bead, for example, can be prepared by coating a substrate comprising an opioid antagonist and/or an antagonist in sequestered form with a solution comprising an opioid agonist.

The sequestering subunits of the invention are particularly well-suited for use in compositions comprising the sequestering subunit and a therapeutic agent in releasable form. In this regard, the invention also provides a composition comprising any of the sequestering subunits of the invention and a therapeutic agent in releasable form. By "releasable form" is meant to include immediate release, intermediate release, and sustained-release forms. The therapeutic agent can be formulated to provide immediate release of the therapeutic agent. In preferred embodiments, the composition provides sustained-release of the therapeutic agent.

The therapeutic agent applied upon the sequestering subunit may be any medicament. The therapeutic agent of the present inventive compositions can be any medicinal agent used for the treatment of a condition or disease, a pharmaceutically acceptable salt thereof, or an analogue of either of the foregoing. The therapeutic agent can be, for example, an analgesic (e.g., an opioid agonist, aspirin, acetaminophen, non-steroidal anti-inflammatory drugs ("NSAIDS"), N-methyl-D-aspartate ("NMDA") receptor antagonists, cyclooxygenase-II inhibitors ("COX-II inhibitors"), and glycine receptor antagonists), an antibacterial agent, an anti-viral agent, an anti-microbial agent, anti-infective agent, a chemotherapeutic, an immunosuppressant agent, an antitussive, an expectorant, a decongestant, an antihistamine drugs, a decongestant, antihistamine drugs, and the like. Preferably, the therapeutic agent is one that is addictive (physically and/or psychologically) upon repeated use and typically leads to abuse of the therapeutic agent. In this regard, the therapeutic agent can be any opioid agonist as discussed herein.

The therapeutic agent can be an opioid agonist. By "opioid" is meant to include a drug, hormone, or other chemical or biological substance, natural or synthetic, having a sedative, narcotic, or otherwise similar effect(s) to those containing opium or its natural or synthetic derivatives. By "opioid agonist," sometimes used herein interchangeably with terms "opioid" and "opioid analgesic," is meant to include one or more opioid agonists, either alone or in combination, and is further meant to include the base of the opioid, mixed or combined agonist-antagonists, partial agonists, pharmaceutically acceptable salts thereof, stereoisomers thereof, ethers thereof, esters thereof, and combinations thereof.

Opioid agonists include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydroetorphine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenazocine, phenomorphan, phenoperidine, piminodine, piritramide, propheptazine, promedol, properidine, propiram, propoxyphene, sufentanil, tramadol; tilidine, derivatives or complexes thereof, pharmaceutically acceptable salts thereof, and combinations thereof. Preferably, the opioid agonist is selected from the group consisting of hydrocodone, hydromorphone, oxycodone, dihydrocodeine, codeine, dihydromorphine, morphine, buprenorphine, derivatives or complexes thereof, pharmaceutically acceptable salts thereof, and combinations thereof. Most preferably, the opioid agonist is morphine, hydromorphone, oxycodone or hydrocodone. In a preferred embodiment, the opioid agonist comprises oxycodone or hydrocodone and is present in the dosage form in an amount of about 15 to about 45 mg, and the opioid antagonist comprises naltrexone and is present in the dosage form in an amount of about 0.5 to about 5 mg.

Equianalgesic doses of these opioids, in comparison to a 15 mg dose of hydrocodone, are set forth in Table 1 below:

TABLE I

Equianalgesic Doses of Opioids

| Opioid | Calculated Dose (mg) |
|---|---|
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

Hydrocodone is a semisynthetic narcotic analgesic and antitussive with multiple nervous system and gastrointestinal actions. Chemically, hydrocodone is 4,5-epoxy-3-methoxy-17-methylmorphinan-6-one, and is also known as dihydrocodeinone. Like other opioids, hydrocodone can be habit-forming and can produce drug dependence of the morphine type. Like other opium derivatives, excess doses of hydrocodone will depress respiration.

Oral hydrocodone is also available in Europe (e.g., Belgium, Germany, Greece, Italy, Luxembourg, Norway and Switzerland) as an antitussive agent. A parenteral formulation is also available in Germany as an antitussive agent. For use as an analgesic, hydrocodone bitartrate is commonly available in the United States only as a fixed combination with non-opiate drugs (e.g., ibuprofen, acetaminophen, aspirin; etc.) for relief of moderate to moderately severe pain.

A common dosage form of hydrocodone is in combination with acetaminophen and is commercially available, for example, as Lortab® in the United States from UCB Pharma, Inc. (Brussels, Belgium), as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen and a 7.5 mg hydrocodone bitartrate and 750 mg acetaminophen. Hydrocodone, in combination with aspirin, is given in an oral dosage form to adults generally in 1-2 tablets every 4-6 hours as needed to alleviate pain. The tablet form is 5 mg hydrocodone bitartrate and 224 mg aspirin with 32 mg caffeine; or 5 mg hydrocodone bitartrate and 500 mg aspirin. Another formulation comprises hydrocodone bitartrate and ibuprofen. Vicoprofen®, commercially available in the U.S. from Knoll Laboratories (Mount Olive, N.J.), is a tablet containing 7.5 mg hydrocodone bitartrate and 200 mg ibuprofen. The invention is contemplated to encompass all such formulations, with the inclusion of the opioid antagonist and/or antagonist in sequestered form as part of a subunit comprising an opioid agonist.

Oxycodone, chemically known as 4,5-epoxy-14-hydroxy-3-methoxy-17-methylmorphinan-6-one, is an opioid agonist whose principal therapeutic action is analgesia. Other therapeutic effects of oxycodone include anxiolysis, euphoria and feelings of relaxation. The precise mechanism of its analgesic action is not known, but specific CNS opioid receptors for endogenous compounds with opioid-like activity have been identified throughout the brain and spinal cord and play a role in the analgesic effects of this drug. Oxycodone is commercially available in the United States, e.g., as Oxycotin® from Purdue Pharma L.P. (Stamford, Conn.), as controlled-release tablets for oral administration containing 10 mg, 20 mg, 40 mg or 80 mg oxycodone hydrochloride, and as OxyIR™, also from Purdue Pharma L.P., as immediate-release capsules containing 5 mg oxycodone hydrochloride. The invention is contemplated to encompass all such formulations, with the inclusion of an opioid antagonist and/or antagonist in sequestered form as part of a subunit comprising an opioid agonist.

Oral hydromorphone is commercially available in the United States, e.g., as Dilaudid® from Abbott Laboratories (Chicago, Ill.). Oral morphine is commercially available in the United States, e.g., as Kadian® from Faulding Laboratories (Piscataway, N.J.).

Exemplary NSAIDS include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well-known. Exemplary NMDA receptor medicaments include morphinans, such as dexotromethorphan or dextrophan, ketamine, d-methadone, and pharmaceutically acceptable salts thereof, and encompass drugs that block a major intracellular consequence of NMDA-receptor activation, e.g., a ganglioside, such as (6-aminothexyl)-5-chloro-1-naphthalenesulfonamide. These drugs are stated to inhibit the development of tolerance to and/or dependence on addictive drugs, e.g., narcotic analgesics, such as morphine, codeine; etc., in U.S. Pat. Nos. 5,321,012 and 5,556,838 (both to Mayer et al.), both of which are incorporated herein by reference, and to treat chronic pain in U.S. Pat. No. 5,502,058 (Mayer et al.), incorporated herein by reference. The NMDA agonist can be included alone or in combination with a local anesthetic, such as lidocaine, as described in these patents by Mayer et al.

COX-2 inhibitors have been reported in the art, and many chemical compounds are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944 and 5,130,311, all of which are incorporated herein by reference. Certain preferred COX-2 inhibitors include celecoxib (SC-58635), DUP-697, flosulide (CGP-28238), meloxicam, 6-methoxy-2-naphthylacetic acid (6-NMA), MK-966 (also known as Vioxx), nabumetone (prodrug for 6-MNA), nimesulide, NS-398, SC-5766, SC-58215, T-614, or combinations thereof. Dosage levels of COX-2 inhibitor on the order of from about 0.005 mg to about 140 mg per kilogram of body weight per day have been shown to be therapeutically effective in combination with an opioid analgesic. Alternatively, about 0.25 mg to about 7 g per patient per day of a COX-2 inhibitor can be administered in combination with an opioid analgesic.

The treatment of chronic pain via the use of glycine receptor antagonists and the identification of such drugs is described in U.S. Pat. No. 5,514,680 (Weber et al.), which is incorporated herein by reference.

In embodiments in which the opioid agonist comprises hydrocodone, the sustained-release oral dosage forms can include analgesic doses from about 8 mg to about 50 mg of hydrocodone per dosage unit. In sustained-release oral dosage forms where hydromorphone is the therapeutically active opioid, it is included in an amount from about 2 mg to about 64 mg hydromorphone hydrochloride. In another embodiment, the opioid agonist comprises morphine, and the sustained-release oral dosage forms of the invention include from about 2.5 mg to about 800 mg morphine, by weight. In yet another embodiment, the opioid agonist comprises oxycodone and the sustained-release oral dosage forms include from about 2.5 mg to about 800 mg oxycodone. In certain preferred embodiments, the sustained-release oral dosage forms include from about 20 mg to about 30 mg oxycodone. Controlled release oxycodone formulations are known in the art. The following documents describe various controlled-release oxycodone formulations suitable for use in the invention described herein, and processes for their manufacture: U.S. Pat. Nos. 5,266,331; 5,549,912; 5,508,042; and 5,656,295, which are incorporated herein by reference. The opioid agonist can comprise tramadol and the sustained-release oral dosage forms can include from about 25 mg to 800 mg tramadol per dosage unit.

The therapeutic agent in sustained-release form is preferably a particle of therapeutic agent that is combined with a release-retarding or sequestering material. The release-retarding or sequestering material is preferably a material that permits release of the therapeutic agent at a sustained rate in an aqueous medium. The release-retarding or sequestering material can be selectively chosen so as to achieve, in combination with the other stated properties, a desired in vitro release rate.

In a preferred embodiment, the oral dosage form of the invention can be formulated to provide for an increased duration of therapeutic action allowing once-daily dosing. In general, a release-retarding or sequestering material is used to provide the increased duration of therapeutic action. Preferably, the once-daily dosing is provided by the dosage forms and methods described in U.S. patent application Ser. No. (unknown) to Boehm, entitled "Sustained-Release Opioid Formulations and Method of Use," filed on Sep. 22, 2003, and incorporated herein by reference.

Preferred release-retarding or sequestering materials include acrylic polymers, alkylcelluloses, shellac, zein, hydrogenated vegetable oil, hydrogenated castor oil, and combinations thereof. In certain preferred embodiments, the release-retarding or sequestering material is a pharmaceutically acceptable acrylic polymer, including acrylic acid and methacrylic acid copolymers, methyl methacrylate copolymers, ethoxyethyl methacrylates, cynaoethyl methacrylate, aminoalkyl methacrylate copolymer, poly(acrylic acid), poly (methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, and glycidyl methacrylate copolymers. In certain preferred embodiments, the acrylic polymer comprises one or more ammonio methacrylate copolymers. Ammonio methacrylate copolymers are well-known in the art, and are described in NF21, the $21^{st}$ edition of the National Formulary, published by the United States Pharmacopeial Convention Inc. (Rockville, Md.), as fully polymerized copolymers of acrylic and methacrylic acid esters with a low content of quaternary ammonium groups. In other preferred embodiments; the release-retarding or sequestering material is an alkyl cellulosic material, such as ethylcellulose. Those skilled in the art will appreciate that other cellulosic polymers, including other alkyl cellulosic polymers, can be substituted for part or all of the ethylcellulose.

Release-modifying agents, which affect the release properties of the release-retarding or sequestering material, also can be used. In a preferred embodiment, the release-modifying agent functions as a pore-former. The pore-former can be organic or inorganic, and include materials that can be dissolved, extracted or leached from the coating in the environment of use. The pore-former can comprise one or more hydrophilic polymers, such as hydroxypropylmethylcellulose. In certain preferred embodiments, the release-modifying agent is selected from hydroxypropylmethylcellulose, lactose, metal stearates, and combinations thereof.

The release-retarding or sequestering material can also include an erosion-promoting agent, such as starch and gums; a release-modifying agent useful for making microporous lamina in the environment of use, such as polycarbonates comprised of linear polyesters of carbonic acid in which carbonate groups reoccur in the polymer chain; and/or a semipermeable polymer.

The release-retarding or sequestering material can also include an exit means comprising at least one passageway, orifice, or the like. The passageway can be formed by such methods as those disclosed in U.S. Pat. Nos. 3,845,770; 3,916,889; 4,063,064; and 4,088,864, which are incorporated herein by reference. The passageway can have any shape, such as round, triangular, square, elliptical, irregular; etc.

In certain embodiments, the therapeutic agent in sustained-release form can include a plurality of substrates comprising the active ingredient, which substrates are coated with a sustained-release coating comprising a release-retarding or sequestering material.

The sustained-release preparations of the invention can be made in conjunction with any multiparticulate system, such as beads, ion-exchange resin beads, spheroids, microspheres, seeds, pellets, granules, and other multiparticulate systems in order to obtain a desired sustained-release of the therapeutic agent. The multiparticulate system can be presented in a capsule or in any other suitable unit dosage form.

In certain preferred embodiments, more than one multiparticulate system can be used, each exhibiting different characteristics, such as pH dependence of release, time for release in various media (e.g., acid, base, simulated intestinal fluid), release in vivo, size and composition.

To obtain a sustained-release of the therapeutic agent in a manner sufficient to provide a therapeutic effect for the sustained durations, the therapeutic agent can be coated with an amount of release-retarding or sequestering material sufficient to obtain a weight gain level from about 2 to about 30%, although the coat can be greater or lesser depending upon the physical properties of the particular therapeutic agent utilized and the desired release rate, among other things. Moreover, there can be more than one release-retarding or sequestering material used in the coat, as well as various other pharmaceutical excipients.

Solvents typically used for the release-retarding or sequestering material include pharmaceutically acceptable solvents, such as water, methanol, ethanol, methylene chloride and combinations thereof.

In certain embodiments of the invention, the release-retarding or sequestering material is in the form of a coating comprising an aqueous dispersion of a hydrophobic polymer.

The inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentrations of the plasticizer, however, can be determined by routine experimentation.

Examples of plasticizers for ethylcellulose and other celluloses include dibutyl sebacate, diethyl phthalate, triethyl citrate, tributyl citrate, and triacetin, although it is possible that other plasticizers (such as acetylated monoglycerides, phthalate esters, castor oil; etc.) can be used. A plasticizer that is not leached into the aqueous phase such as DBS is preferred.

Examples of plasticizers for the acrylic polymers include citric acid esters, such as triethyl citrate NF21, tributyl citrate, dibutyl phthalate (DBP), acetyltri-N-butyl citrate (ATBC), and possibly 1,2-propylene glycol, polyethylene glycols, propylene glycol, diethyl phthalate, castor oil, and triacetin, although it is possible that other plasticizers (such as acetylated monoglycerides, phthalate esters, castor oil; etc.) can be used.

The sustained-release profile of drug release in the formulations of the invention (either in vivo or in vitro) can be altered, for example, by using more than one release-retarding or sequestering material, varying the thickness of the release-retarding or sequestering material, changing the particular release-retarding or sequestering material used, altering the relative amounts of release-retarding or sequestering material, altering the manner in which the plasticizer is added (e.g., when the sustained-release coating is derived from an aqueous dispersion of hydrophobic polymer), by varying the amount of plasticizer relative to retardant material, by the inclusion of additional ingredients or excipients, by altering the method of manufacture; etc.

In certain other embodiments, the oral dosage form can utilize a multiparticulate sustained-release matrix. In certain embodiments, the sustained-release matrix comprises a hydrophilic and/or hydrophobic polymer, such as gums, cellulose ethers, acrylic resins and protein-derived materials. Of these polymers, the cellulose ethers, specifically hydroxyalkylcelluloses and carboxyalkylcelluloses, are preferred. The oral dosage form can contain between about 1% and about 80% (by weight) of at least one hydrophilic or hydrophobic polymer.

The hydrophobic material is preferably selected from the group consisting of alkylcellulose, acrylic and methacrylic acid polymers and copolymers, shellac, zein, hydrogenated castor oil, hydrogenated vegetable oil, or mixtures thereof. Preferably, the hydrophobic material is a pharmaceutically acceptable acrylic polymer, including acrylic acid and methacrylic acid copolymers, methyl methacrylate, methyl methacrylate copolymers, ethoxyethyl methacrylates, cyanoethyl methacrylate, aminoalkyl methacrylate copolymer, poly (acrylicacid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers. In other embodiments, the hydrophobic material can also include hydrooxyalkylcelluloses such as hydroxypropylmethylcellulose and mixtures of the foregoing.

Preferred hydrophobic materials are water-insoluble with more or less pronounced hydrophobic trends. Preferably, the hydrophobic material has a melting point from about 30° C. to about 200° C., more preferably from about 45° C. to about 90° C. The hydrophobic material can include neutral or synthetic waxes, fatty alcohols (such as lauryl, myristyl, stearyl, cetyl or preferably cetostearyl alcohol), fatty acids, including fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include beeswax, glycowax, castor wax, carnauba wax and wax-like substances, e.g., material normally solid at room temperature and having a melting point of from about 30° C. to about 100° C.

Preferably, a combination of two or more hydrophobic materials are included in the matrix formulations. If an additional hydrophobic material is included, it is preferably a natural or synthetic wax, a fatty acid, a fatty alcohol, or mixtures thereof. Examples include beeswax, carnauba wax, stearic acid and stearyl alcohol.

In other embodiments, the sustained-release matrix comprises digestible, long-chain (e.g., $C_8$-$C_{50}$, preferably $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between about 25° C. and about 90° C. are preferred. Of these long-chain hydrocarbon materials, fatty (aliphatic) alcohols are preferred. The oral dosage form can contain up to about 60% (by weight) of at least one digestible, long-chain hydrocarbon. Further, the sustained-release matrix can contain up to 60% (by weight) of at least one polyalkylene glycol.

In a preferred embodiment, the matrix comprises at least one water-soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$-$C_6$) alkyl cellulose, such as hydroxypropylcellulose, hydroxypropylmethylcellulose and, preferably, hydroxyethyl cellulose. The amount of the at least one hydroxyalkyl cellulose in the oral dosage form will be determined, amongst other things, by the precise rate of opioid release required. The amount of the at least one aliphatic alcohol in the present oral dosage form will be determined by the precise rate of opioid release required. However, it will also depend on whether the at least one polyalkylene glycol is absent from the oral dosage form.

In certain embodiments, a spheronizing agent, together with the active ingredient, can be spheronized to form spheroids. Microcrystalline cellulose and hydrous lactose impalpable are examples of such agents. Additionally (or alternatively), the spheroids can contain a water-insoluble polymer, preferably an acrylic polymer, an acrylic copolymer, such as a methacrylic acid-ethyl acrylate copolymer, or ethyl cellulose. In such embodiments, the sustained-release coating will generally include a water-insoluble material such as (a) a wax, either alone or in admixture with a fatty alcohol, or (b) shellac or zein.

The sustained-release unit can be prepared by any suitable method. For example, a plasticized aqueous dispersion of the release-retarding or sequestering material can be applied onto the subunit comprising the opioid agonist. A sufficient amount of the aqueous dispersion of release-retarding or sequestering material to obtain a predetermined sustained-release of the opioid agonist when the coated substrate is exposed to aqueous solutions, e.g., gastric fluid, is preferably applied, taking into account the physical characteristics of the opioid agonist, the manner of incorporation of the plasticizer; etc. Optionally, a further overcoat of a film-former, such as Opadry (Colorcon, West Point, Va.), can be applied after coating with the release-retarding or sequestering material.

The subunit can be cured in order to obtain a stabilized release rate of the therapeutic agent. In embodiments employing an acrylic coating, a stabilized product can be preferably obtained by subjecting the subunit to oven curing at a temperature above the glass transition temperature of the plasticized acrylic polymer for the required time period. The optimum temperature and time for the particular formulation can be determined by routine experimentation.

Once prepared, the subunit can be combined with at least one additional subunit and, optionally, other excipients or drugs to provide an oral dosage form. In addition to the above ingredients, a sustained-release matrix also can contain suitable quantities of other materials, e.g., diluents, lubricants, binders, granulating aids, colorants, flavorants and glidants that are conventional in the pharmaceutical art.

Optionally and preferably, the mechanical fragility of any of the sequestering subunits described herein is the same as the mechanical fragility of the therapeutic agent in releasable form. In this regard, tampering with the composition of the invention in a manner to obtain the therapeutic agent will result in the destruction of the sequestering subunit, such that the antagonist is released and mixed in with the therapeutic agent. Consequently, the antagonist cannot be separated from the therapeutic agent, and the therapeutic agent cannot be administered in the absence of the antagonist. Methods of assaying the mechanical fragility of the sequestering subunit and of a therapeutic agent are known in the art.

The composition of the invention can be in any suitable dosage form or formulation, (see, e.g., *Pharmaceutics and Pharmacy Practice*, J. B. Lippincott Company, Philadelphia, Pa., Banker and Chalmers, eds., pages 238-250 (1982)).

Pharmaceutically acceptable salts of the antagonist or agonist agents discussed herein include metal salts, such as sodium salt, potassium salt, cesium salt, and the like; alkaline earth metals, such as calcium salt, magnesium salt, and the like; organic amine salts, such as triethylamine salt, pyridine salt, picoline salt, ethanolamine salt, triethanolamine salt, dicyclohexylamine salt, N,N'-dibenzylethylenediamine salt, and the like; inorganic acid salts, such as hydrochloride, hydrobromide, sulfate, phosphate, and the like; organic acid salts, such as formate, acetate, trifluoroacetate, maleate, tartrate, and the like; sulfonates, such as methanesulfonate, benzenesulfonate, p-toluenesulfonate, and the like; amino acid salts, such as arginate, asparginate, glutamate, and the like. Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystallize cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

One of ordinary skill in the art will readily appreciate that the compositions of the invention can be modified in any number of ways, such that the therapeutic efficacy of the composition is increased through the modification. For instance, the therapeutic agent or sequestering subunit could be conjugated either directly or indirectly through a linker to a targeting moiety. The practice of conjugating therapeutic agents or sequestering subunits to targeting moieties is known in the art. See, for instance, Wadwa et al., *J. Drug Targeting* 3: 111 (1995), and U.S. Pat. No. 5,087,616. The term "targeting moiety" as used herein, refers to any molecule or agent that specifically recognizes and binds to a cell-surface receptor, such that the targeting moiety directs the delivery of the therapeutic agent or sequestering subunit to a population of cells on which the receptor is expressed. Targeting moieties include, but are not limited to, antibodies, or fragments thereof, peptides, hormones, growth factors, cytokines, and any other naturally- or non-naturally-existing ligands, which bind to cell-surface receptors. The term "linker" as used herein, refers to any agent or molecule that bridges the therapeutic agent or sequestering subunit to the targeting moiety. One of ordinary skill in the art recognizes that sites on the therapeutic agent or sequestering subunit, which are not necessary for the function of the agent or sequestering subunit, are ideal sites for attaching a linker and/or a targeting moiety, provided that the linker and/or targeting moiety, once attached to the agent or sequestering subunit, do(es) not interfere with the function of the therapeutic agent or sequestering subunit.

With respect to the present inventive compositions, the composition is preferably an oral dosage form. By "oral dosage form" is meant to include a unit dosage form prescribed or intended for oral administration comprising subunits. Desirably, the composition comprises the sequestering subunit coated with the therapeutic agent in releasable form, thereby forming a composite subunit comprising the sequestering subunit and the therapeutic agent. Accordingly, the invention further provides a capsule suitable for oral administration comprising a plurality of such composite subunits.

Alternatively, the oral dosage form can comprise any of the sequestering subunits of the invention in combination with a therapeutic agent subunit, wherein the therapeutic agent subunit comprises the therapeutic agent in releasable form. In this respect, the invention provides a capsule suitable for oral administration comprising a plurality of sequestering subunits of the invention and a plurality of therapeutic subunits, each of which comprises a therapeutic agent in releasable form.

The invention further provides tablets comprising a sequestering subunit of the invention and a therapeutic agent in releasable form. For instance, the invention provides a tablet suitable for oral administration comprising a first layer comprising any of the sequestering subunits of the invention and a second layer comprising therapeutic agent in releasable form, wherein the first layer is coated with the second layer. The first layer can comprise a plurality of sequestering subunits. Alternatively, the first layer can be or can consist of a single sequestering subunit. The therapeutic agent in releasable form can be in the form of a therapeutic agent subunit and the second layer can comprise a plurality of therapeutic subunits. Alternatively, the second layer can comprise a single substantially homogeneous layer comprising the therapeutic agent in releasable form.

When the blocking agent is a system comprising a first antagonist-impermeable material and a core, the sequestering subunit can be in one of several different forms. For example, the system can further comprise a second antagonist-impermeable material, in which case the sequestering unit comprises an antagonist, a first antagonist-impermeable material, a second antagonist-impermeable material, and a core. In this instance, the core is coated with the first antagonist-impermeable material, which, in turn, is coated with the antagonist, which, in turn, is coated with the second antagonist-impermeable material. The first antagonist-impermeable material and second antagonist-impermeable material substantially prevent release of the antagonist from the sequestering subunit in the gastrointestinal tract for a time period that is greater than 24 hours. In some instances, it is preferable that the first antagonist-impermeable material is the same as the second antagonist-impermeable material. In other instances, the first antagonist-impermeable material is different from the second antagonist-impermeable material. It is within the skill of the ordinary artisan to determine whether or not the first and second antagonist-impermeable materials should be the same or different. Factors that influence the decision as to whether the first and second antagonist-impermeable materials should be the same or different can include whether a layer to be placed over the antagonist-impermeable material requires certain properties to prevent dissolving part or all of the antagonist-impermeable layer when applying the next layer or properties to promote adhesion of a layer to be applied over the antagonist-impermeable layer.

Alternatively, the antagonist can be incorporated into the core, and the core is coated with the first antagonist-impermeable material. In this case, the invention provides a sequestering subunit comprising an antagonist, a core and a first antagonist-impermeable material, wherein the antagonist is incorporated into the core and the core is coated with the first antagonist-impermeable material, and wherein the first antagonist-impermeable material substantially prevents release of the antagonist from the sequestering subunit in the gastrointestinal tract for a time period that is greater than 24 hours. By "incorporate" and words stemming therefrom, as used herein is meant to include any means of incorporation, e.g., homogeneous dispersion of the antagonist throughout the core, a single layer of the antagonist coated on top of a core, or a multi-layer system of the antagonist, which comprises the core.

In another alternative embodiment, the core comprises a water-insoluble material, and the core is coated with the antagonist, which, in turn, is coated with the first antagonist-impermeable material. In this case, the invention further provides a sequestering subunit comprising an antagonist, a first antagonist-impermeable material, and a core, which comprises a water-insoluble material, wherein the core is coated with the antagonist, which, in turn, is coated with the first antagonist-impermeable material, and wherein the first antagonist-impermeable material substantially prevents release of the antagonist from the sequestering subunit in the gastrointestinal tract for a time period that is greater than 24 hours. The term "water-insoluble material" as used herein means any material that is substantially water-insoluble. The term "substantially water-insoluble" does not necessarily refer to complete or 100% water-insolubility. Rather, there are varying degrees of water insolubility of which one of ordinary skill in the art recognizes as having a potential benefit. Preferred water-insoluble materials include, for example, microcrystalline cellulose, a calcium salt, and a wax. Calcium salts include, but are not limited to, a calcium phosphate (e.g., hydroxyapatite, apatite; etc.), calcium carbonate, calcium sulfate, calcium stearate, and the like. Waxes include, for example, carnuba wax, beeswax, petroleum wax, candelilla wax, and the like.

In one embodiment, the sequestering subunit includes an antagonist and a seal coat where the seal coat forms a layer physically separating the antagonist within the sequestering subunit from the agonist which is layered upon the sequestering subunit. In one embodiment, the seal coat comprises one or more of an osmotic pressure regulating agent, a charge-neutralizing additive, a sequestering polymer hydrophobicity-enhancing additive, and a first sequestering polymer (each having been described above). In such embodiments, it is preferred that the osmotic pressure regulating agent, charge-neutralizing additive, and/or sequestering polymer hydrophobicity-enhancing additive, respectively where present, are present in proportion to the first sequestering polymer such that no more than 10% of the antagonist is released from the intact dosage form. Where an opioid antagonist is used in the sequestering subunit and the intact dosage form includes an opioid agonist, it is preferred that ratio of the osmotic pressure regulating agent, charge-neutralizing additive, and/or sequestering polymer hydrophobicity-enhancing additive, respectively where present, in relation to the first sequestering polymer is such that the physiological effect of the opioid agonist is not diminished when the composition is in its intact dosage form or during the normal course digestion in the patient. Release may be determined as described above using the USP paddle method (optionally using a buffer containing a surfactant such as Triton X-100) or measured from plasma after administration to a patient in the fed or non-fed state. In one embodiment, plasma naltrexone levels are determined; in others, plasma 6-beta naltrexol levels are determined. Standard tests may be utilized to ascertain the antagonist's effect on agonist function (i.e., reduction of pain).

The sequestering subunit of the invention can have a blocking agent that is a tether to which the antagonist is attached. The term "tether" as used herein refers to any means by which the antagonist is tethered or attached to the interior of the sequestering subunit, such that the antagonist is not released, unless the sequestering subunit is tampered with. In this instance, a tether-antagonist complex is formed. The complex is coated with a tether-impermeable material, thereby substantially preventing release of the antagonist from the subunit. The term "tether-impermeable material" as used herein refers to any material that substantially prevents or prevents the tether from permeating through the material. The tether preferably is an ion exchange resin bead.

The invention further provides a tablet suitable for oral administration comprising a single layer comprising a therapeutic agent in releasable form and a plurality of any of the sequestering subunits of the invention dispersed throughout the layer of the therapeutic agent in releasable form. The invention also provides a tablet in which the therapeutic agent in releasable form is in the form of a therapeutic agent subunit and the tablet comprises an at least substantially homogeneous mixture of a plurality of sequestering subunits and a plurality of subunits comprising the therapeutic agent.

In preferred embodiments, oral dosage forms are prepared to include an effective amount of melt-extruded subunits in the form of multiparticles within a capsule. For example, a plurality of the melt-extruded multiparticulates can be placed in a gelatin capsule in an amount sufficient to provide an effective release dose when ingested and contacted by gastric fluid.

In another preferred embodiment, the subunits, e.g., in the form of multiparticulates, can be compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Aurther Osol., editor), 1553-1593 (1980), which is incorporated herein by reference. Excipients in tablet formulation can include, for example, an inert diluent such as lactose, granulating and disintegrating agents, such as cornstarch, binding agents, such as starch, and lubricating agents, such as magnesium stearate. In yet another preferred embodiment, the subunits are added during the extrusion process and the extrudate can be shaped into tablets as set forth in U.S. Pat. No. 4,957,681 (Klimesch et al.), which is incorporated herein by reference.

Optionally, the sustained-release, melt-extruded, multiparticulate systems or tablets can be coated, or the gelatin capsule can be further coated, with a sustained-release coating, such as the sustained-release coatings described herein. Such coatings are particularly useful when the subunit comprises an opioid agonist in releasable form, but not in sustained-release form. The coatings preferably include a sufficient amount of a hydrophobic material to obtain a weight gain level form about 2 to about 30 percent, although the overcoat can be greater, depending upon the physical properties of the particular opioid analgesic utilized and the desired release rate, among other things.

The melt-extruded dosage forms can further include combinations of melt-extruded multiparticulates containing one or more of the therapeutically active agents before being encapsulated. Furthermore, the dosage forms can also include an amount of an immediate release therapeutic agent for prompt therapeutic effect. The immediate release therapeutic agent can be incorporated or coated on the surface of the subunits after preparation of the dosage forms (e.g., controlled-release coating or matrix-based). The dosage forms can also contain a combination of controlled-release beads and matrix multiparticulates to achieve a desired effect.

The sustained-release formulations preferably slowly release the therapeutic agent, e.g., when ingested and exposed to gastric fluids, and then to intestinal fluids. The sustained-release profile of the melt-extruded formulations can be altered, for example, by varying the amount of retardant, e.g., hydrophobic material, by varying the amount of plasticizer relative to hydrophobic material, by the inclusion of additional ingredients or excipients, by altering the method of manufacture; etc.

In other embodiments, the melt-extruded material is prepared without the inclusion of the subunits, which are added thereafter to the extrudate. Such formulations can have the subunits and other drugs blended together with the extruded matrix material, and then the mixture is tableted in order to provide a slow release of the therapeutic agent or other drugs. Such formulations can be particularly advantageous, for example, when the therapeutically active agent included in the formulation is sensitive to temperatures needed for softening the hydrophobic material and/or the retardant material.

In certain embodiments, the release of the antagonist of the sequestering subunit or composition is expressed in terms of a ratio of the release achieved after tampering, e.g., by crushing or chewing, relative to the amount released from the intact formulation. The ratio is, therefore, expressed as Crushed: Whole, and it is desired that this ratio have a numerical range of at least about 4:1 or greater (e.g., crushed release within 1 hour/intact release in 24 hours). In certain embodiments, the ratio of the therapeutic agent and the antagonist, present in the sequestering subunit, is about 1:1 to about 50:1 by weight, preferably about 1:1 to about 20:1 by weight or 15:1 to about 30:1 by weight. The weight ratio of the therapeutic agent to antagonist refers to the weight of the active ingredients. Thus, for example, the weight of the therapeutic agent excludes the weight of the coating, matrix, or other component that renders the antagonist sequestered, or other possible excipients associated with the antagonist particles. In certain preferred embodiments, the ratio is about 1:1 to about 10:1 by weight. Because in certain embodiments the antagonist is in a sequestered from, the amount of such antagonist within the dosage form can be varied more widely than the therapeutic agent/antagonist combination dosage forms, where both are available for release upon administration, as the formulation does not depend on differential metabolism or hepatic clearance for proper functioning. For safety reasons, the amount of the antagonist present in a substantially non-releasable form is selected as not to be harmful to humans, even if fully released under conditions of tampering.

Thus, in certain embodiments, a pharmaceutical composition comprising an antagonist in direct contact with a seal coat, an agonist in direct contact with the seal coat and a sequestering polymer but not the antagonist, wherein the antagonist and agonist are present within a single multilayer pharmaceutical unit, is provided. In others, pharmaceutical compositions comprising a pharmaceutical dosing unit consisting essentially of a multiple layer bead comprising an antagonist and an agonist that are not in direct contact with one another are provided. In yet others, pharmaceutical composition comprising a plurality of pharmaceutically active units wherein each unit comprises an antagonist, an agonist, a seal coat, and a sequestering polymer wherein the antagonist and the agonist are not in direct contact with one another. In still others, pharmaceutical compositions comprising a pharmaceutically inert support material such as a sugar sphere, an antagonist in direct contact with the support material, a seal coat in direct contact with the antagonist and an agonist, and a sequestering polymer in direct contact with the agonist are provided. In preferred embodiments, multiple layer pharmaceutical compositions comprising an agonist and an antagonist within distinct layers of the composition, wherein at least 90-95% of the antagonist is sequestered for at least 24 hours following administration to a human being are provided. In a particularly preferred embodiment, a pharmaceutical composition comprising naltrexone within a sequestering subunit and morphine in contact with the subunit but not the naltrexone, wherein administration of the composition to a human being results in the release of substantially all of the morphine from the composition but less than 5-10% of the naltrexone from the composition within 24 hours of administration, is provided. Also provided are methods for preparing pharmaceutical compositions by, for example, adhering an antagonist to a pharmaceutically inert support material, coating the antagonist with a seal coat that includes a sequestering polymer, coating the seal coat with an agonist, and coating the agonist with a release-retarding or sequestering material. In another embodiment, a method for measuring the amount of antagonist or derivative thereof in a biological sample, the antagonist or derivative having been released from a pharmaceutical composition in vivo, the method comprising the USP paddle method at 37° C., 100 rpm, but further comprising incubation in a buffer containing a surfactant such as Triton X-100, for example.

A particularly preferred embodiment comprises a multiple layer pharmaceutical is described in the Examples is multilayer naltrexone/morphine dosing unit in an abuse-resistant dosage form. Naltrexone is contained in a sequestering subunit comprising a seal coat comprising Eudragit® RS and the optimization agents SLS, talc and chloride ions that together prevent release of naltrexone upon hydration. Overlayed onto the sequestering subunit is a layer comprising morphine that is released upon hydration in pH 7.5 buffer; the naltrexone, however, remains within the sequestering subunit under these conditions. If the unit is modified by, for example, crushing the unit, the sequestering subunit is crushed as well causing the release of both morphine and naltrexone therefrom.

Thus, the compositions are particularly well-suited for use in preventing abuse of a therapeutic agent. In this regard, the invention also provides a method of preventing abuse of a therapeutic agent by a human being. The method comprises incorporating the therapeutic agent into any of the compositions of the invention. Upon administration of the composition of the invention to the person, the antagonist is substantially prevented from being released in the gastrointestinal tract for a time period that is greater than 24 hours. However, if a person tampers with the compositions, the sequestering subunit, which is mechanically fragile, will break and thereby allow the antagonist to be released. Since the mechanical fragility of the sequestering subunit is the same as the therapeutic agent in releasable form, the antagonist will be mixed with the therapeutic agent, such that separation between the two components is virtually impossible.

A better understanding of the present invention and of its many advantages will be had from the following examples, given by way of illustration.

EXAMPLES

The preparations and experiments described below were actually performed. In certain cases, however, the present tense is utilized.

Example 1

Formulation Evaluation

A. Exclusion of Charge-neutralization Additive (SLS)

| | RB 380-56 | |
|---|---|---|
| | Gram per batch | Percent |
| Seal-coated sugar spheres | | |
| Sugar spheres | 577.9 | 51.8 |
| Ethylcellulose N50 | 46.2 | 4.1 |
| Talc | 123.3 | 11.1 |
| Dibutyl Sebacate | 4.6 | 0.4 |
| Naltrexone cores | | |
| Seal-coated sugar spheres | (752.0) | (67.4) |
| Naltrexone HCl | 27.2 | 2.4 |
| Klucel LF | 5.2 | 0.5 |
| Talc | 12.8 | 1.1 |
| Ascorbic acid | 2.8 | 0.3 |
| Naltrexone pellets | | |
| Naltrexone cores | (800.0) | (71.7) |
| Eudragit RS | 150.0 | 13.5 |
| Sodium lauryl sulfate | 0.0 | 0.0 |
| Talc | 150.0 | 13.5 |
| Dibutyl Sebacate | 15.0 | 1.3 |
| Total | 1115.0 | 100.0 |

Method of Preparation:
1. Ethylcellulose and dibutyl sebacate were dissolved into ethanol and talc dispersed into the solution.
2. The dispersion from 1 was sprayed onto sugar spheres in a Wurster to form seal-coated sugar spheres.
3. Klucel LF and ascorbic acid were dissolved into a 20:80 mixture of water and ethanol. Disperse naltrexone HCl and talc into the solution.
4. The naltrexone dispersion from 3 was sprayed onto seal-coated sugar spheres from 2 in a Wurster to form naltrexone cores.
5. Eudragit RS and dibutyl debacate were dissolved into ethanol and talc dispersed into the solution.
6. The dispersion from 5 was sprayed onto the naltrexone cores from 4 in a Wurster to form naltrexone pellets.
7. Pellets were dried at 50° C. for 48 hours.
8. The resulting pellets had a Eudragit RS coat thickness of 47 μm.

Drug Release Results

Dissolution conditions: USP paddle method at 37° C. and 100 rpm, 1 hour in 500 mL of 0.1N HCl followed by 72 hours in 500 mL of 0.05M pH 7.5 phosphate buffer.

Conclusions: The results are shown in FIG. 1. The exclusion of SLS from the Naltrexone pellet (Eudragit RS) coat results in rapid release of Naltrexone, with more than 90% release in 24 hours.

B. Variable Amounts of SLS (Eudragit RS Coat Thickness of 53 μm)

|  | Batch Number | | | | | |
| --- | --- | --- | --- | --- | --- | --- |
|  | RB 358-88 | | RB 358-73 | | RB 358-83 | |
|  | Gm per batch | Percent | Gm per batch | Percent | Gm per batch | Percent |
| Seal-coated sugar spheres |  |  |  |  |  |  |
| Sugar spheres | 646.1 | 50.1 | 646.1 | 50.0 | 646.1 | 49.8 |
| Ethylcellulose N50 | 48.5 | 3.8 | 48.5 | 3.7 | 48.5 | 3.7 |
| Talc | 126.0 | 9.8 | 126.0 | 9.7 | 126.0 | 9.7 |
| Dibutyl Sebacate | 4.9 | 0.4 | 4.9 | 0.4 | 4.9 | 0.4 |
| Magnesium stearate | 19.4 | 1.5 | 19.4 | 1.5 | 19.4 | 1.5 |
| Sodium lauryl sulfate | 1.9 | 0.2 | 1.9 | 0.1 | 1.9 | 0.1 |
| Naltrexone cores |  |  |  |  |  |  |
| Seal-coated sugar spheres | (846.7) | (65.6) | (846.7) | (65.5) | (846.7) | (65.2) |
| Naltrexone HCl | 29.5 | 2.3 | 29.5 | 2.3 | 29.5 | 2.3 |
| Klucel LF | 5.9 | 0.5 | 5.9 | 0.5 | 5.9 | 0.5 |
| Talc | 17.8 | 1.4 | 17.8 | 1.4 | 17.8 | 1.4 |
| Naltrexone pellets |  |  |  |  |  |  |
| Naltrexone cores | (900.0) | (69.7) | (900.0) | (69.6) | (900.0) | (69.3) |
| Eudragit RS | 184.6 | 14.3 | 184.3 | 14.3 | 183.7 | 14.2 |
| Sodium lauryl sulfate | 3.0 | 0.23 | 6.1 | 0.47 | 12.3 | 0.95 |
| Talc | 184.6 | 14.3 | 184.3 | 14.3 | 183.7 | 14.2 |
| Dibutyl Sebacate | 18.5 | 1.4 | 18.4 | 1.4 | 18.4 | 1.4 |
| Total | 1290.7 | 100.0 | 1293.2 | 100.0 | 1298.1 | 100.0 |

Method of Preparation:
1. Ethylcellulose, sodium lauryl sulfate and dibutyl sebacate were dissolved into ethanol, and then talc and magnesium stearate were dispersed into the solution.
2. The dispersion from 1 was sprayed onto sugar spheres in a Wurster to form seal-sugar spheres.
3. Klucel LF was dissolved into a 20:80 mixture of water and ethanol. Naltrexone HCl and talc were then dispersed into the solution.
4. The naltrexone dispersion from 3 was then sprayed onto seal-coated sugar spheres from 2 in a Wurster to form naltrexone cores.
5. Eudragit RS, sodium lauryl sulfate and dibutyl debacate were dissolved into ethanol, and talc dispersed into the solution.
6. The dispersion from 5 was sprayed onto naltrexone cores from 4 in a Wurster to form naltrexone pellets.
7. The pellets were dried at 50° C. for 13-16.5 hours.
8. The resulting pellets had a Eudragit RS coat thickness of 51-53 μm.

Drug Release Results

Figure 2:
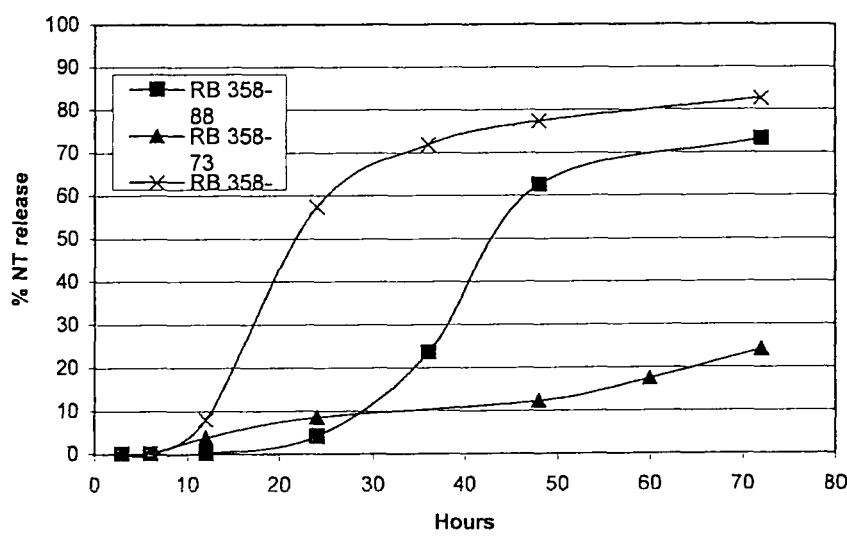
FIG. 2. Effect of SLS levels in Eudragit® RS coat on naltrexone (NT) release.

Dissolution conditions: USP paddle method at 37° C. and 100 rpm, 72 hours in 500 mL of 0.05M pH 7.5 phosphate buffer Conclusions: The results are shown in FIG. 2. Addition of a small amount of SLS (1.6% w/w of Eudragit RS) results in charge neutralization of Eudragit RS (theoretically 20% neutralization), and significantly slows down the release of naltrexone. Further addition of SLS (3.2% w/w of Eudragit RS) leads to further Eudragit RS charge neutralization (theoretically 41% neutralization), and dramatically slows down release of naltrexone. Still higher amount of SLS (6.3% w/w of Eudragit RS), however, results in higher naltrexone release, possibly due to plasticizing effect of SLS.

3. Different Levels of SLS (Eudragit RS Coat Thickness of 65 μm)

|  | Batch Number | | | | | |
| --- | --- | --- | --- | --- | --- | --- |
|  | RB 358-88A | | RB 358-73A | | RB 358-83A | |
|  | Gm per batch | Percent | Gm per batch | Percent | Gm per batch | Percent |
| Seal-coated sugar spheres |  |  |  |  |  |  |
| Sugar spheres | 646.1 | 45.5 | 646.1 | 45.4 | 646.1 | 45.1 |
| Ethylcellulose N50 | 48.5 | 3.4 | 48.5 | 3.4 | 48.5 | 3.4 |
| Talc | 126.0 | 8.9 | 126.0 | 8.8 | 126.0 | 8.8 |
| Dibutyl Sebacate | 4.9 | 0.3 | 4.9 | 0.3 | 4.9 | 0.3 |
| Magnesium stearate | 19.4 | 1.4 | 19.4 | 1.4 | 19.4 | 1.4 |
| Sodium lauryl sulfate | 1.9 | 0.1 | 1.9 | 0.1 | 1.9 | 0.1 |
| Naltrexone cores |  |  |  |  |  |  |
| Seal-coated sugar spheres | (846.7) | (59.6) | (846.7) | (59.4) | (846.7) | (59.1) |
| Naltrexone HCl | 29.5 | 2.1 | 29.5 | 2.1 | 29.5 | 2.1 |
| Klucel LF | 5.9 | 0.4 | 5.9 | 0.4 | 5.9 | 0.4 |
| Talc | 17.8 | 1.3 | 17.8 | 1.2 | 17.8 | 1.2 |

-continued

| | Batch Number | | | | | |
|---|---|---|---|---|---|---|
| | RB 358-88A | | RB 358-73A | | RB 358-83A | |
| | Gm per batch | Percent | Gm per batch | Percent | Gm per batch | Percent |
| Naltrexone pellets | | | | | | |
| Naltrexone cores | (900.0) | (63.4) | (900.0) | (63.2) | (900.0) | (62.8) |
| Eudragit RS | 245.8 | 17.3 | 245.8 | 17.3 | 245.8 | 17.2 |
| Sodium lauryl sulfate | 4.0 | 0.3 | 8.2 | 0.6 | 16.4 | 1.1 |
| Talc | 245.8 | 17.3 | 245.8 | 17.3 | 245.8 | 17.2 |
| Dibutyl Sebacate | 24.6 | 1.7 | 24.6 | 1.7 | 24.6 | 1.7 |
| Total | 1420.2 | 100.0 | 1424.4 | 100.0 | 1432.6 | 100.0 |

Method of Preparation
1. Ethylcellulose, sodium lauryl sulfate and dibutyl sebacate were dissolved into ethanol; talc and magnesium stearate were then dispersed into the solution.
2. The dispersion from 1 was sprayed onto sugar spheres in a Wurster to form seal-coated sugar spheres.
3. Klucel LF was dissolved into a 20:80 mixture of water and ethanol; naltrexone HCl and talc were then dispersed into the solution.
4. The naltrexone dispersion from 3 was then sprayed onto seal-coated sugar spheres from 2 in a Wurster to form naltrexone cores.
5. Eudragit RS, sodium lauryl sulfate and dibutyl debacate were dissolved into ethanol; talc was then dispersed into the solution.
6. The dispersion from 5 was sprayed onto naltrexone cores from 4 in a Wurster to form naltrexone pellets.
7. The pellets were dried at 50° C. for 1316.5 hours.
8. The resulting pellets had a Eudragit RS coat thickness of 63-67 μm.

Drug Release Results

Figure 3:
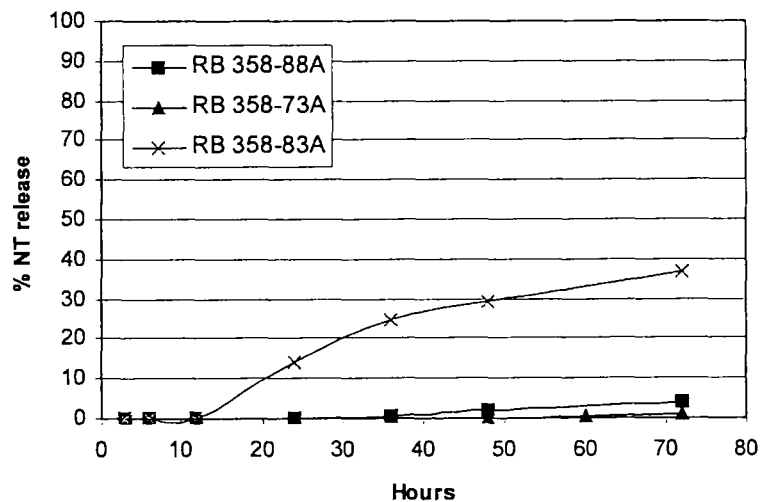
FIG. 3. Effect of SLS levels in Eudragit® RS coat on naltrexone (NT) release.

Dissolution conditions: USP paddle method at 37° C. and 100 rpm, 72 hours in 500 mL of 0.05M pH 7.5 phosphate buffer Conclusions: The results are shown in FIG. 3. As described above, there is an optimal ratio of SLS to Eudragit RS.

B. Talc Content Relative to Eudragit RS Polymer

| | Batch Number | | | | | |
|---|---|---|---|---|---|---|
| | RB 358-93 | | RB 358-73A | | RB 358-78 | |
| | Gm per batch | Percent | Gm per batch | Percent | Gm per batch | Percent |
| Seal-coated sugar spheres | | | | | | |
| Sugar spheres | 646.1 | 46.5 | 646.1 | 45.4 | 646.1 | 43.9 |
| Ethylcellulose N50 | 48.5 | 3.5 | 48.5 | 3.4 | 48.5 | 3.3 |
| Talc | 126.0 | 9.1 | 126.0 | 8.8 | 126.0 | 8.6 |
| Dibutyl Sebacate | 4.9 | 0.4 | 4.9 | 0.3 | 4.9 | 0.3 |
| Magnesium stearate | 19.4 | 1.4 | 19.4 | 1.4 | 19.4 | 1.3 |
| Sodium lauryl sulfate | 1.9 | 0.1 | 1.9 | 0.1 | 1.9 | 0.1 |
| Naltrexone cores | | | | | | |
| Seal-coated sugar spheres | (846.7) | (61.0) | (846.7) | (59.4) | (846.7) | (57.5) |
| Naltrexone HCl | 29.5 | 2.1 | 29.5 | 2.1 | 29.5 | 2.0 |
| Klucel LF | 5.9 | 0.4 | 5.9 | 0.4 | 5.9 | 0.4 |
| Talc | 17.8 | 1.3 | 17.8 | 1.2 | 17.8 | 1.2 |
| Naltrexone pellets | | | | | | |
| Naltrexone cores | (900.0) | (64.8) | (900.0) | (63.2) | (900.0) | (61.1) |
| Eudragit RS | 266.5 | 19.2 | 245.8 | 17.3 | 216.7 | 14.7 |
| Sodium lauryl sulfate | 8.8 | 0.6 | 8.2 | 0.6 | 7.2 | 0.5 |
| Talc | 186.2 | 13.4 | 245.8 | 17.3 | 326.3 | 22.2 |
| Dibutyl Sebacate | 26.6 | 1.9 | 24.6 | 1.7 | 21.7 | 1.5 |
| Total | 1388.1 | 100.0 | 1424.4 | 100.0 | 1471.9 | 100.0 |

Method of Preparation
1. Dissolve Ethylcellulose, sodium lauryl sulfate and dibutyl sebacate into ethanol, then disperse talc and magnesium stearate into the solution.
2. Spray the dispersion from 1 onto sugar spheres in a Wurster to form seal-coated sugar spheres.
3. Dissolve Klucel LF into 20:80 mixture of water and ethanol. Disperse naltrexone HCl and talc into the solution.
4. Spray the naltrexone dispersion from 3 onto seal-coated sugar spheres from 2 in a Wurster to form naltrexone cores.
5. Dissolve Eudragit RS, sodium lauryl sulfate and dibutyl debacate into ethanol. Disperse talc into the solution.
6. Spray the dispersion from 5 onto naltrexone cores from 4 in a Wurster to form naltrexone pellets.
7. Pellets are dried at 50° C. for 13-16.5 hours.
8. Resulting pellets have Eudragit RS coat thickness of 63-67 μm.

Drug Release Results

Figure 4:
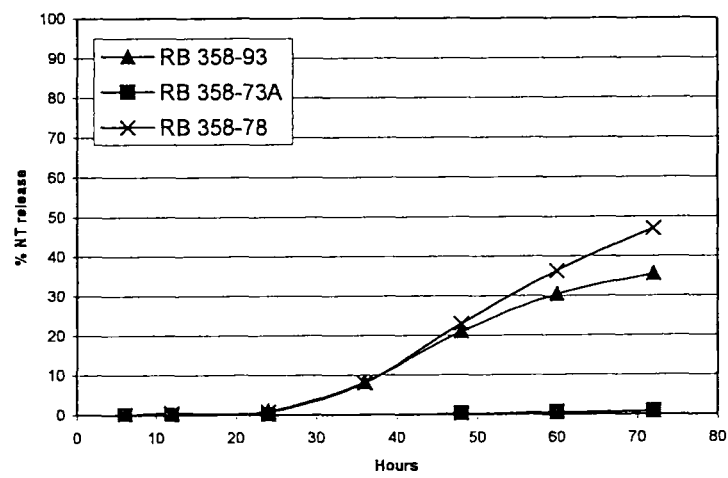
FIG. 4. Effect of talc levels in Eudragit® RS coat on naltrexone (NT) release.
Figure 5:
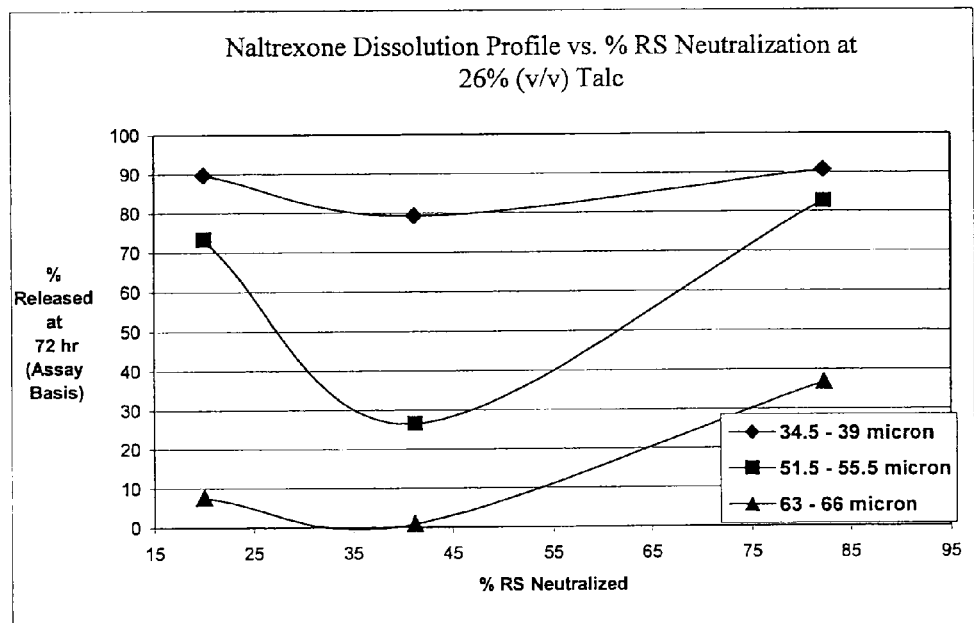
FIG. 5. Naltrexone dissolution profile vs. Eudragit® RS neutralization at 26% (v/v) talc.
Figure 6:
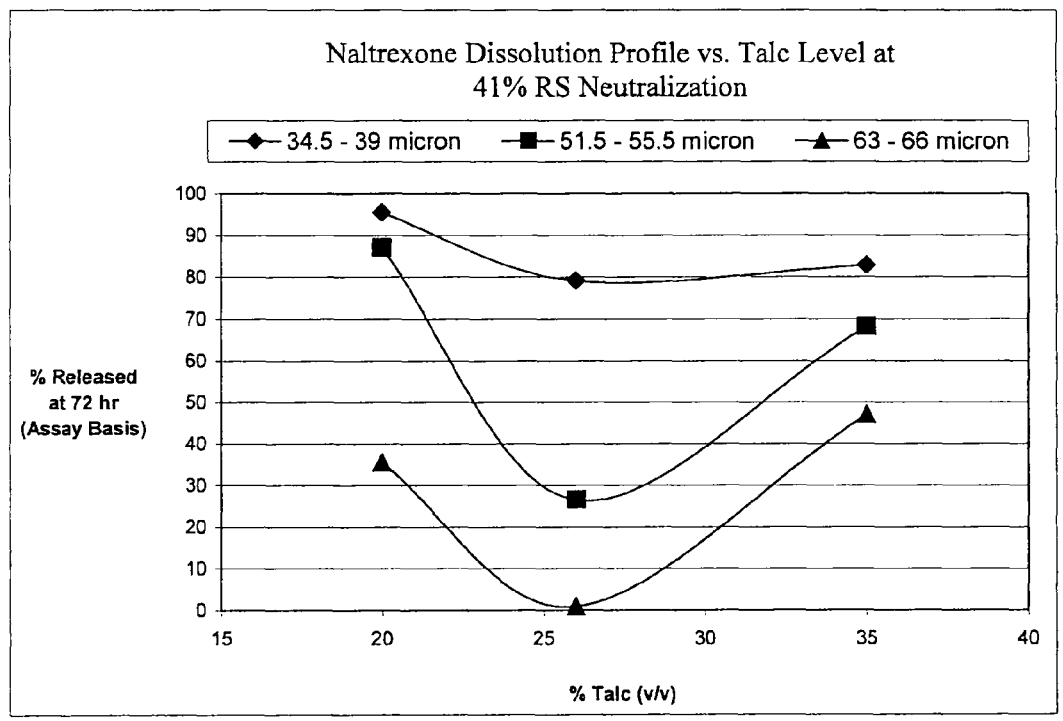
FIG. 6. Naltrexone dissolution profile vs. talc level at 41% Eudragit® RS neutralization.
Figure 7:
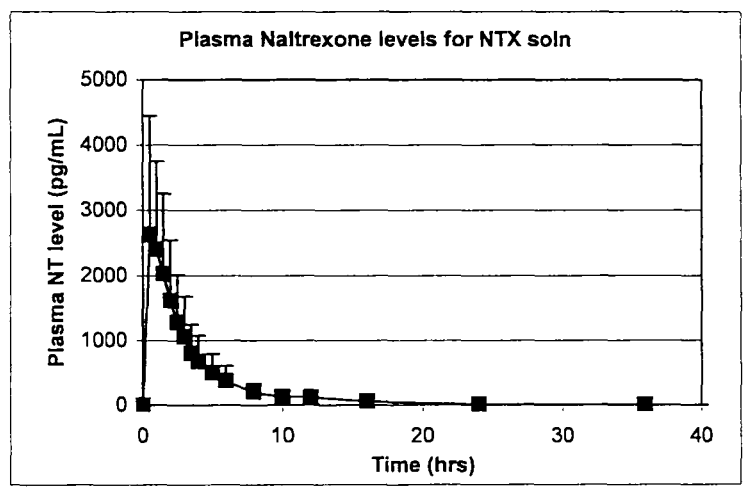
FIG. 7. Plasma naltrexone levels for naltrexone (NTX) solution.
Figure 8:
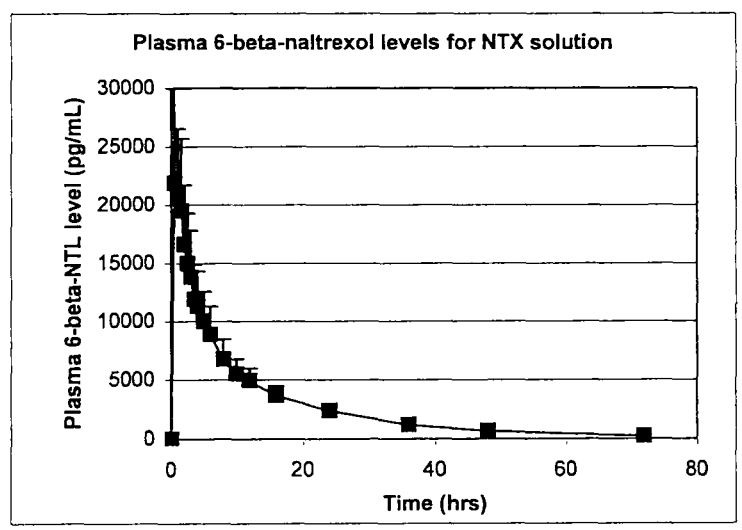
FIG. 8. Plasma 6-beta-naltrexol levels for naltrexone (NTX) solution.
Figure 9:
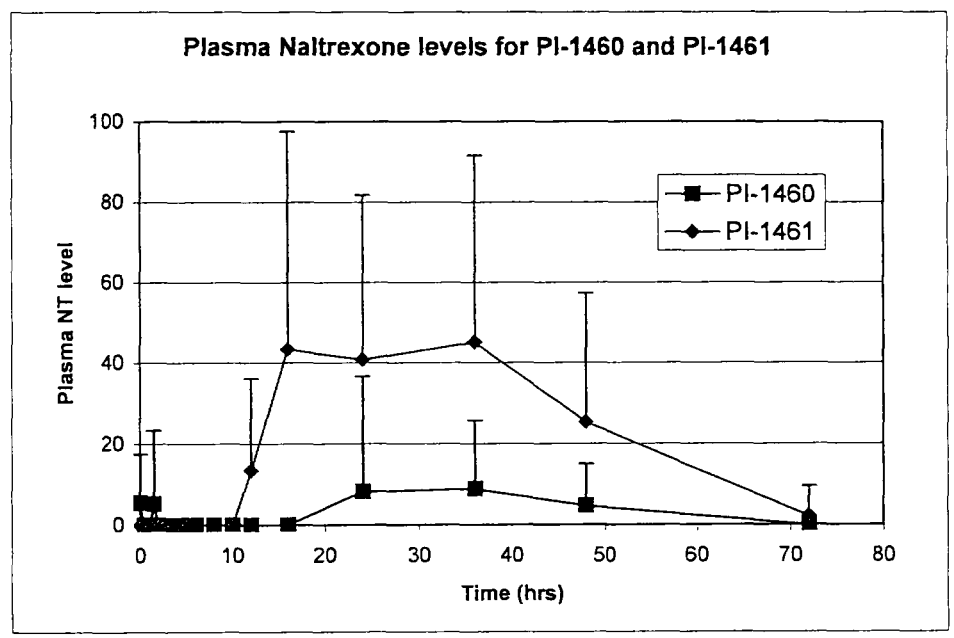
FIG. 9. Plasma naltrexone levels for PI-1460 and PI-1461.
Figure 10:
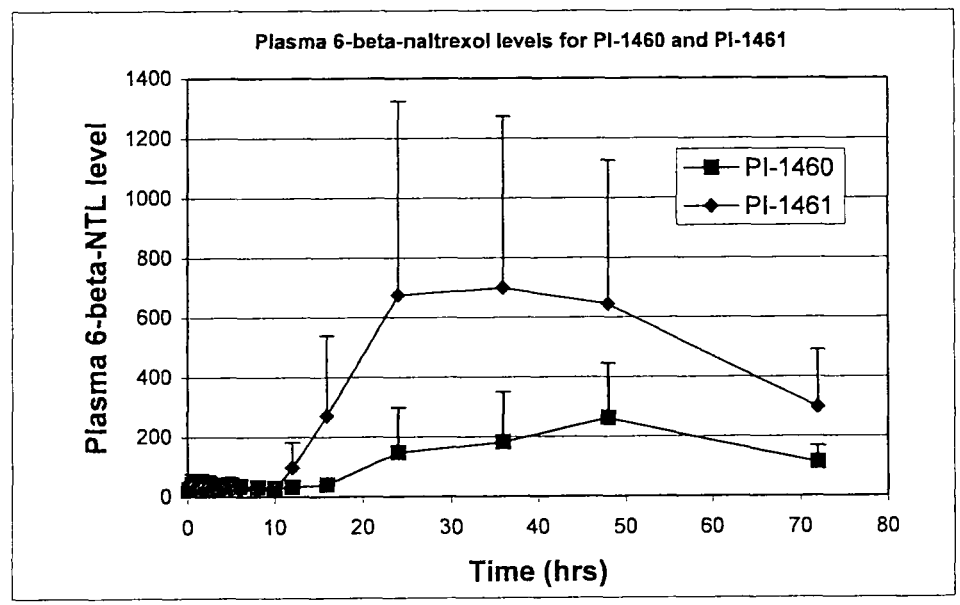
FIG. 10. Plasma 6-beta naltrexol levels for PI-1460 and PI-1461.

Dissolution conditions: USP paddle method at 37° C. and 100 rpm, 72 hours in 500 mL of 0.05M pH 7.5 phosphate buffer Conclusions: The results of this assay are shown in FIG. 4, and demonstrate that there is an optimal ratio of talc to Eudragit RS (approximately 1:1). Talc increases the hydrophobicity of the Eudragit RS coat, but also reduces film integrity at high amount. FIG. 5 demonstrates the transition point in the behavior of the film. FIG. 6 demonstrates that there is a distinct optimum in the relationship between film permeability and talc content when using a sugar sphere core.

C. Effects of Osmotic Pressure Reducing Agents on Top of Eudragit RS Coat

|  | Percent Batch Number | | | |
|---|---|---|---|---|
|  | RB 362-28 | RB 362-48 | RB 362-67 | RB 362-65 |
| Naltrexone cores | | | | |
| Naltrexone HCl | 1.10 | 0.93 | 0.89 | 1.00 |
| Sugar (#20-25 mesh) | 24.48 | 20.59 | 19.80 | 22.15 |
| HPC (Klucel LF) | 0.22 | 0.19 | | |
| HPMC, 3 cps | | | 0.18 | 0.20 |
| Citric acid | | | 0.004 | 0.004 |
| Ascorbic acid | | | 0.004 | 0.004 |
| BHA | | | 0.004 | 0.004 |
| Talc | 0.66 | 0.56 | 0.54 | 0.60 |
| Naltrexone pellets | | | | |
| Naltrexone cores | (26.47) | (22.26) | (21.41) | (23.95) |
| Eudragit RS PO | 10.64 | 8.95 | 8.62 | 9.64 |
| SLS | 0.36 | 0.30 | 0.29 | 0.33 |
| DBS | 1.06 | 0.89 | 0.85 | 0.95 |
| Talc | 10.89 | 9.16 | 8.62 | 9.64 |
| Naltrexone-morphine cores | | | | |
| Naltrexone pellets | (49.41) | (41.55) | (39.78) | (44.50) |
| Morphine sulfate | 26.05 | 21.70 | 21.70 | 24.76 |
| Confectioner's sugar | | 13.66 | 9.32 | |
| Sodium chloride | | | 6.43 | 7.01 |
| HPMC, 3 cps | 2.32 | 3.46 | 3.13 | 4.10 |
| Naltrexone-morphine pellets | | | | |
| Naltrexone-morphine cores | (77.78) | (80.37) | (80.37) | (80.37) |
| Ethylcellulose N50 | 7.48 | 7.07 | 7.07 | 7.07 |
| PEG 6000 | 3.59 | 2.88 | 2.81 | 2.62 |
| Eudragit L100-55 | 2.10 | 1.70 | 1.77 | 1.96 |
| DEP | 1.65 | 1.44 | 1.44 | 1.44 |
| Talc | 7.41 | 6.54 | 6.54 | 6.54 |
| Total | 100.00 | 100.00 | 100.00 | 100.00 |

Method of Preparation:
1. Klucel LF or HPMC (with or without citric acid, ascorbic acid and butylated hydroxyanisole) was dissolved into 20:80 mixture of water and ethanol; naltrexone HCl and talc were dispersed into the solution.
2. The naltrexone dispersion from 1 was sprayed onto sugar spheres in a Wurster to form naltrexone cores.
3. Eudragit RS, sodium lauryl sulfate and dibutyl debacate were dissolved into ethanol; talc was then dispersed into the solution.
4. The dispersion from 3 was sprayed onto naltrexone cores from 2 in a Wurster to form naltrexone pellets.
5. The Naltrexone pellets were dried at 50° C. for either 12 hours (RB 362-28 and RB 362-48) or 65 hours (RB 362-67 and RB 362-65).
6. The resulting pellets had a Eudragit RS coat thickness of 85-90 μm.
7. Sodium chloride and hypromellose were then dissolved into water.
8. HPMC was dissolved into either water or mixture of ethanol and water.
9. Sodium chloride was dissolved into the HPMC solution from 8.
10. Confectioner's sugar was dispersed into the HPMC solution from 8.
11. Morphine sulfate was dispersed into the HPMC solution from 8.
12.
   a. For RB 362-28, spray onto naltrexone pellets in 5 in a rotor the solution from 8, followed by the dispersion from 11, to form naltrexone-morphine cores.
   b. For RB 362-48, spray onto naltrexone pellets in 5 in a rotor the solution from 8, followed by the dispersion from 10, followed by the solution from 8, and followed by the dispersion from 11, to form naltrexone-morphine cores.
   c. For RB 362-67, spray onto naltrexone pellets in 5 in a rotor the solution from 9, followed by the dispersion from 10, followed by the solution from 8, and followed by the dispersion from 11, to form naltrexone-morphine cores.
   d. For RB 362-65, spray onto naltrexone pellets in 5 in a rotor the solution from 9; followed by the solution from 8, and followed by the dispersion from 11, to form naltrexone-morphine cores.
13. Ethylcellulose, PEG 6000, Eudragit L100-55 and diethyl phthalate were dissolved into ethanol and talc was dispersed into the solution.
14. The dispersion from 13 was sprayed onto naltrexone-morphine cores in 12 to form naltrexone-morphine pellets.

Drug Release Results:
Dissolution conditions: USP paddle method at 37° C. and 100 rpm, 72 hours in 500 mL of 0.05M pH 7.5 phosphate buffer; or, USP paddle method at 37° C. and 100 rpm, 1 hour in 0.1N HCl, followed by 72 hours in 0.05M pH 7.5 phosphate buffer Results:

| Batch Number | | % NT release at the end of dissolution |
|---|---|---|
| RB 362-28 | Naltrexone pellet | 2 |
|  | Naltrexone-morphine pellet | 7.9 |
| RB 362-48 | Naltrexone pellet | 2 |
|  | Naltrexone-morphine pellet | 68.5 |
| RB 362-67 | Naltrexone pellet | 0 |
|  | Naltrexone-morphine pellet | 25 |
| RB 362-65 | Naltrexone pellet | 0.2 |
|  | Naltrexone-morphine pellet | 1.4 |

Conclusions: Sugar has a detrimental effect on NT release. The use of NaCl/HPMC provides the desired NT release profile.

II. Proof of Concept Study, 16 mg Naltrexone HCl (20-727-1N)

|  | PI-1460 | | PI-1461 | |
|---|---|---|---|---|
|  | mg/unit | Percent | mg/unit | Percent |
| Naltrexone HCl | 8 | 2.23 | 8 | 2.07 |
| Sugar sphere (#20-25 mesh) | 177.9 | 49.6 | | |
| Cellets (#20-25 mesh) | | | 228.3 | 59.1 |
| HPC (Klucel LF) | 1.6 | 0.4 | 1.6 | 0.4 |
| Talc | 4.8 | 1.3 | 4.8 | 1.2 |
| Eudragit RS PO | 77.3 | 21.5 | 66.2 | 17.2 |
| SLS | 2.6 | 0.7 | 2.3 | 0.6 |
| DBS | 7.7 | 2.1 | 6.6 | 1.7 |
| Talc | 79.1 | 22.0 | 68.2 | 17.7 |
| Total | 359 | 100.0 | 386 | 100.0 |

A. Method of Preparation—
1. Dissolve Klucel LF into 20:80 mixture of water and ethanol. Disperse naltrexone HCl and talc into the solution.

2. Spray the naltrexone dispersion from 1 onto sugar spheres (for PI-1460) or Cellets (for PI-1461) in a Wurster to form naltrexone cores.
3. Dissolve Eudragit RS, sodium lauryl sulfate and dibutyl sebacate into ethanol. Disperse talc into the solution.
4. Spray the dispersion from 3 onto naltrexone cores from 2 in a Wurster to form naltrexone pellets.
5. The naltrexone pellets are dried in an oven at 50° C. for 12 hours.
6. Resulting pellets have Eudragit RS coat thickness of 90 μm (for PI-1460) and 60 μm (for PI-1461).
7. The pellets are filled into capsules.

B. In-vitro Drug Release—
Method—USP paddle method at 37° C. and 100 rpm; 1 hour in 0.1N HCl, then 72 hours in 0.05M pH 7.5 phosphate buffer
Results—Percent of NT released at 73 hours for PI-1460=2%
Percent of NT released at 73 hours for PI-1461=0%

C. In-vivo Biostudy—
Single-dose, open-label, two-period pilot study in 26 healthy subjects under fasting conditions:
Period 1: Oral liquid containing 16 mg naltrexone (N=26)
Period 2: 2 capsules of PI-1460 (N=13) or PI-1461 (N=13)
Blood samples were withdrawn from prior to dosing and from 0.5 to 72 hours after dosing, and analyzed for plasma naltrexone and 6-beta-Naltrexol levels. Limit of quantitation was 20.0 pg/mL for naltrexone and 0.250 pg/mL for 6-beta-Naltrexol. The data is shown in FIGS. 7-10.
Summary of Pharmacokinetic Results—

III. Optimization Study #1, Morphine Sulfate and Naltrexone 60 mg/2.4 mg (ALPH-KNT-002)

|  | PI-1462 | | PI-1463 | |
|---|---|---|---|---|
|  | mg/unit | Percent | mg/unit | Percent |
| Naltrexone cores | | | | |
| Naltrexone HCl | 2.4 | 0.96 | 2.4 | 0.94 |
| Cellets (#20-25 mesh) | 67.1 | 26.8 | 59.8 | 23.4 |
| HPC (Klucel LF) | 0.5 | 0.2 | 0.5 | 0.2 |
| Citric acid | 0.01 | 0.0040 | 0.01 | 0.004 |
| Ascorbic acid | 0.01 | 0.0040 | 0.01 | 0.004 |
| BHA | 0.01 | 0.0040 | 0.01 | 0.004 |
| Talc | 1.38 | 0.6 | 1.57 | 0.6 |
| Subtotal | 71.4 | 28.5 | 64.3 | 25.1 |
| Naltrexone pellets | | | | |
| Naltrexone cores | (71.4) | (28.5) | (64.3) | (25.1) |
| Eudragit RS PO | 19.5 | 7.8 | 26 | 10.2 |
| SLS | 0.7 | 0.3 | 0.9 | 0.4 |
| DBS | 2 | 0.8 | 2.6 | 1.0 |
| Talc | 20 | 8.0 | 26.6 | 10.4 |
| Subtotal | 113.6 | 45.4 | 120.4 | 47.1 |
| Naltrexone-morphine cores | | | | |
| Naltrexone pellets | (113.6) | (45.4) | (120.4) | (47.1) |
| Morphine sulfate | 58.7 | 23.5 | 56.3 | 22.0 |
| Sodium chloride | 16.6 | 6.6 | 16.6 | 6.5 |
| HPMC, 3 cps | 13.6 | 5.4 | 13.5 | 5.3 |
| Subtotal | 202.5 | 80.9 | 206.8 | 80.8 |
| Naltrexone-morphine pellets | | | | |
| Naltrexone-morphine cores | (202.5) | (80.9) | (206.8) | (80.8) |
| Ethylcellulose N50 | 16 | 6.4 | 16.4 | 6.4 |

|  | 6-beta-Naltrexol | | | Naltrexone | | |
|---|---|---|---|---|---|---|
|  | николай NTX Solution | 2 capsules of PI-1460 | 2 capsules of PI-1461 | NTX Solution | 2 capsules of PI-1460 | 2 capsules of PI-1461 |
| Tmax (hr) | 0.75 | 43.02 | 32.01 | 0.75 | 24.38 (N = 4) | 23.21 (N = 10) |
| Cmax (pg/mL) | 24600 | 298 | 834 | 2950 | 22.4 (N = 11) | 60.7 |
| AUC$_{last}$ (pg * h/mL) | 205800 | 10460 | 32530 | 8925 | 200.2 (N = 11) | 1258 |
| AUC$_{linf}$ (pg * h/mL) | 212700 | | | 9569 (N = 23) | | |
| Relative Bioavailability to an oral solution: | | | | | | |
| Cmax Ratio (Capsule/Solution) | | 1.21% | 3.39% | | 0.76% | 2.06% |
| AUC$_{last}$ Ratio (Capsule/Solution) | | 5.08% | 15.80% | | 2.24% | 14.08% |

N = 26 for Solution, unless specified otherwise
N = 12 for PI-1460 or PI-1461, unless specified otherwise D. Conclusion—
1. Plasma 6-beta-naltrexol levels provide a more accurate indicator of bioavailability than plasma NT levels, due to its higher plasma levels and higher analytical sensitivity.
2. Using 6-beta-naltrexol AUC$_{last}$ ratio of capsules to solution as indicator of cumulative in vivo NT release, significant sequestering of naltrexone is observed to 72 hours under fasting condition. Using Cellets as seed cores resulted in three times higher observed in vivo NT release than sugar. However, NT pellets using Cellet have lower RS coat thickness than Sugar (60 μm versus 90 μm), because at 60 μm, Cellet NT pellets have slightly better in vitro dissolution performance than Sugar NT pellets at 90 μm.

-continued

|  | PI-1462 | | PI-1463 | |
|---|---|---|---|---|
|  | mg/unit | Percent | mg/unit | Percent |
| PEG 6000 | 7.4 | 3.0 | 7.6 | 3.0 |
| Eudragit L100-55 | 3.5 | 1.4 | 3.6 | 1.4 |
| DEP | 3.3 | 1.3 | 3.4 | 1.3 |
| Talc | 17.5 | 7.0 | 18 | 7.0 |
| Total | 250.2 | 100.0 | 255.8 | 100.0 |

A. Method of Preparation—
1. Dissolve Klucel LF, citric acid, ascorbic acid and butylated hydroxyanisole into 20:80 mixture of water and ethanol. Disperse naltrexone HCl and talc into the solution.

2. Spray the naltrexone dispersion from 1 onto Cellets in a Wurster to form naltrexone cores.
3. Dissolve Eudragit RS, sodium lauryl sulfate and dibutyl debacate into ethanol. Disperse talc into the solution.
4. Spray the dispersion from 3 onto naltrexone cores from 2 in a Wurster to form naltrexone pellets.
5. The Naltrexone pellets are dried at 50° C. for 48 hours.
6. Resulting pellets have a Eudragit RS coat thickness of 60 µm for PI-1462 and 90 µm for PI-1463.
7. Dissolve sodium chloride and hypromellose into water.
8. Dissolve hypromellose into 10:90 mixture of water and ethanol. Disperse morphine sulfate into the solution.
9. Spray the solution from 7 followed by the dispersion from 8 onto naltrexone pellets in 5 in a rotor to form naltrexone-morphine cores.
10. Dissolve ethylcellulose, PEG 6000, Eudragit L100-55 and diethyl phthalate into ethanol. Disperse talc into the solution.
11. Spray the dispersion from 10 onto naltrexone-morphine cores in 9 to form naltrexone-morphine pellets.
12. The pellets are filled into capsules.

B. In-vitro Drug Release—
Method—USP paddle method at 37° C. and 100 rpm
1 hour in 0.1N HCl, then 72 hours in 0.05M pH 7.5 phosphate buffer
Results—Percent of NT released at 73 hours for PI-1462=0%
Percent of NT released at 73 hours for PI-1463=0%

Figure 11:
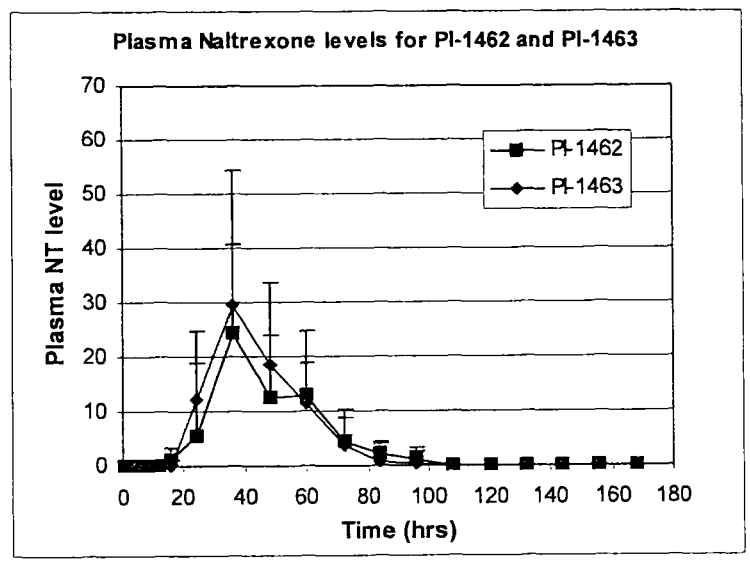
FIG. 11. Plasma naltrexone levels for PI-1462 and PI-1463.
Figure 12:
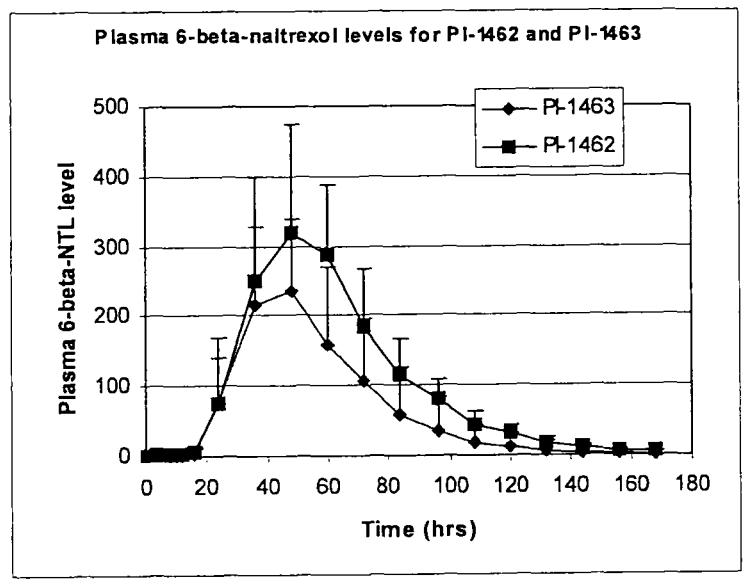
FIG. 12. Plasma 6-beta-naltrexol levels for PI-1462 and PI-1463.

C. In-civo Study
This is a single-dose, open-label, single-period study in which two groups of eight subjects received one dose of either PI-1462 or PI-1463 under fasting condition. Blood samples were drawn prior to dose administration and at 0.5 to 168 hours post-dose. Limits of quantitation are 4.00 pg/mL for naltrexone and 0.250 pg/mL for 6-beta-naltrexol. The data is shown in FIGS. 11-12.

2. Summary of Pharmacokinetics Parameters

|  | 6-beta-Naltrexol | | Naltrexone | |
| --- | --- | --- | --- | --- |
|  | PI-1462 | PI-1463 | PI-1462 | PI-1463 |
| Tmax (hr) | 49.52 | 40.53 | 42.03 | 37.75 (N = 3) |
| Cmax (pg/mL) | 349 | 285 | 25.3 | 35.5 |
| AUC$_{last}$ (pg * h/mL) | 16850 | 11130 | 705.1 | 835.0 |
| AUC∞ (pg * h/mL) | 17040 | 11170 | 1057 (N = 4) | 1711 (N = 3) |
| T½ (hr) | 18.18 | 14.49 | 14.15 (N = 4) | 8.89 (N = 3) |
| Relative Bioavailability to an oral solution (Dose-adjusted) | | | | |
| Cmax Ratio (Test/Solution) | 9.46% | 7.72% | 5.71% | 8.02% |
| AUC$_{last}$ Ratio (Test/Solution) | 54.58% | 36.05% | 52.67% | 62.37% |
| AUC∞ Ratio (Test/Solution) | 53.41% | 35.01% | 78.95% | 119.2% |

N = 8, unless specified otherwise

3. Conclusion
a. Plasma 6-beta-naltrexol levels provide more consistent indication of bioavailability than Naltrexone.
b. There is significant release in-vivo in both formulations, as indicated by relative bioavailability based on AUC∞ ratios. 90 µm coat thickness results in less release than 60 µm. Comparing PI-1463 (Opt #1) with PI-1461 (POC), the coating of morphine/NaCl/Kadian ER coat on top of Naltrexone pellet causes more than three-fold increase in NT release.
c. 7-day duration of study allows 6-beta-naltrexol to return to baseline.
d. There is clearly no in vitro/in vivo correlation regarding NT release, using conventional buffer system. In vitro dissolution shows 0% NT release at the end of 72 hours, but in vivo data reveals significant NT release.

IV. Optimization Studies #2 and #3, Morphine Sulfate and Naltrexone HCl 60 mg/2.4 mg (20-778-1N and 20-779-1N)

|  | PI-1465 | | PI-1466 | |
| --- | --- | --- | --- | --- |
|  | mg/unit | Percent | mg/unit | Percent |
| Sealed-coated sugar spheres | | | | |
| Sugar spheres (#20-25 mesh) | 52.1 | 16.0 | 53.1 | 14.6 |
| Ethylcellulose N50 | 3.9 | 1.2 | 3.98 | 1.1 |
| Mag Stearate | 1.6 | 0.5 | 1.6 | 0.4 |
| Dibutyl Sebecate | 0.4 | 0.1 | 0.4 | 0.1 |
| Talc | 10 | 3.1 | 10.27 | 2.8 |
| Subtotal | 68.0 | 20.9 | 69.4 | 19.0 |
| Naltrexone cores | | | | |
| Sealed sugar spheres | (68.0) | (20.9) | (69.4) | (19.0) |
| Naltrexone HCl | 2.4 | 0.74 | 2.4 | 0.66 |
| HPC (Klucel LF) | 0.5 | 0.2 | 0.5 | 0.1 |
| Citric acid | 0.01 | 0.0031 | 0.01 | 0.0027 |
| Ascorbic acid | 0.01 | 0.0031 | 0.01 | 0.0027 |
| Butylated Hydroxyanisole | 0.01 | 0.0031 | 0.01 | 0.0027 |
| Talc | 1.4 | 0.4 | 1.43 | 0.4 |
| Subtotal | 72.3 | 22.3 | 73.7 | 20.2 |
| Naltrexone pellets | | | | |
| Naltrexone cores | (144.7) | (44.5) | (147.4) | (40.4) |
| Eudragit RS PO | 25.4 | 7.8 | 38.7 | 10.6 |
| Sodium lauryl sulfate | 0.9 | 0.3 | 1.31 | 0.4 |
| Dibutyl Sebecate | 2.53 | 0.8 | 3.87 | 1.1 |
| Talc | 26 | 8.0 | 38.7 | 10.6 |
| Subtotal | 199.5 | 61.4 | 230.0 | 63.1 |

-continued

|  | PI-1465 | | PI-1466 | |
| --- | --- | --- | --- | --- |
|  | mg/unit | Percent | mg/unit | Percent |
| Naltrexone-morphine cores | | | | |
| Naltrexone pellets | (199.5) | (61.4) | (230.0) | (63.1) |
| Morphine sulfate | 59.3 | 18.2 | 59.5 | 16.3 |
| Sodium chloride | 17.5 | 5.4 | 20.1 | 5.5 |
| Hypromellose 2910, 3 cps | 14.2 | 4.4 | 15.1 | 4.1 |
| Subtotal | 290.5 | 89.4 | 324.7 | 89.0 |

|  | PI-1465 | | PI-1466 | |
| --- | --- | --- | --- | --- |
|  | mg/unit | Percent | mg/unit | Percent |
| Naltrexone-morphine pellets | | | | |
| Naltrexone-morphine cores | (290.5) | (89.4) | (324.7) | (89.0) |
| Ethylcellulose N50 | 11.51 | 3.5 | 13.1 | 3.6 |
| Polyethylene glycol 6000 | 5.3 | 1.6 | 6.1 | 1.7 |
| Eudragit L100-55 | 2.1 | 0.6 | 2.85 | 0.8 |
| Diethyl Phthalate | 2.4 | 0.7 | 2.8 | 0.8 |
| Talc | 13.23 | 4.1 | 15.2 | 4.2 |
| Total | 325.0 | 100.0 | 364.8 | 100.0 |

A. Method of Preparation—

1. Dissolve Ethylcellulose and dibutyl sebacate into ethanol, then disperse talc and magnesium stearate into the solution.
2. Spray the dispersion from 1 onto sugar spheres in a Wurster to form seal-coated sugar spheres (25 μm seal coat thickness).
3. Dissolve Klucel LF, citric acid, ascorbic acid and butylated hydroxyanisole into 20:80 mixture of water and ethanol. Disperse naltrexone HCl and talc into the solution.
4. Spray the naltrexone dispersion from 3 onto seal-coated sugar spheres from 2 in a Wurster to form naltrexone cores.
5. Dissolve Eudragit RS, sodium lauryl sulfate and dibutyl debacate into ethanol. Disperse talc into the solution.
6. Spray the dispersion from 5 onto naltrexone cores from 4 in a Wurster to form naltrexone pellets.
7. The Naltrexone pellets are dried at 50° C. for 48 hours.
8. Resulting pellets have a Eudragit RS coat thickness of 90 μm for PI-1465 and 120 μm for PI-1466.
9. Dissolve sodium chloride and hypromellose into water.
10. Dissolve hypromellose into 10:90 mixture of water and ethanol. Disperse morphine sulfate into the solution.
11. Spray the solution from 9 followed by the dispersion from 10 onto naltrexone pellets in 7 in a rotor to form naltrexone-morphine cores.
12. Dissolve ethylcellulose, PEG 6000, Eudragit L100-55 and diethyl phthalate into ethanol. Disperse talc into the solution.
13. Spray the dispersion from 12 onto naltrexone-morphine cores in 11 to form naltrexone-morphine pellets.
14. The pellets are filled into capsules.

B. In-vitro Drug Release—

Figure 13:
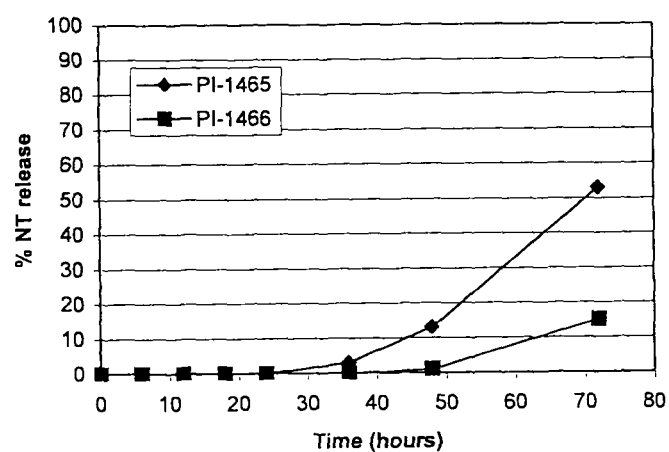
FIG. 13. Percent naltrexone (NT) release for PI-1465 and PI-1466.

1. Method—USP paddle method at 37° C. and 100 rpm
   1 hour in 0.1N HCl, then 72 hours in 0.05 M pH 7.5 phosphate buffer
   Results—Percent of NT released at 73 hours for PI-1465=1%
   Percent of NT released at 73 hours for PI-1466=0%
2. Method—USP paddle method at 37° C. and 100 rpm
   72 hrs in 0.2% Triton X-100/0.2% sodium acetate/ 0.002N HCl, pH 5.5
   The data is shown in FIG. 13.

C. In-vivo Study #1

Figure 14:
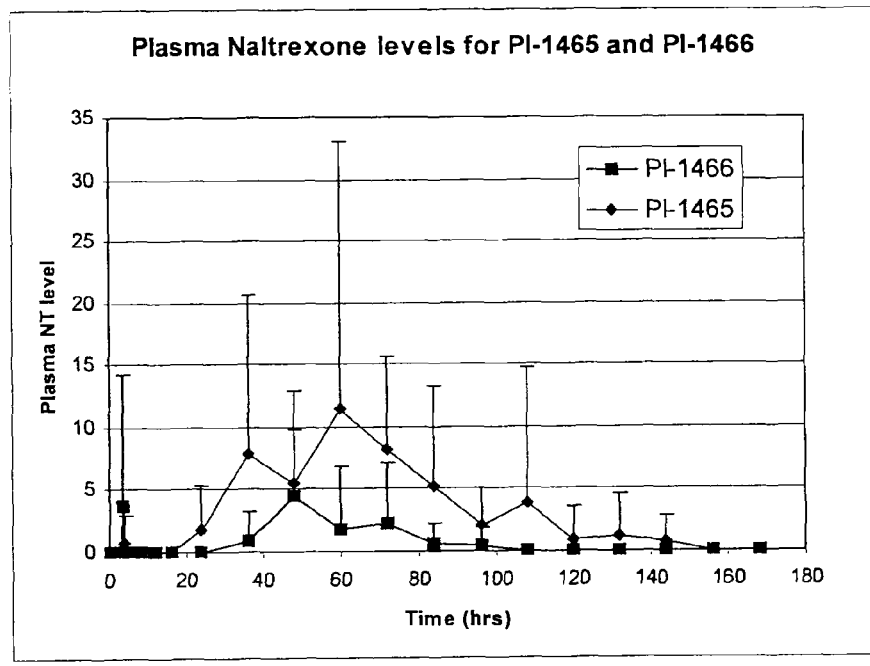
FIG. 14. Plasma naltrexone levels for PI-1465 and PI-1466.
Figure 15:
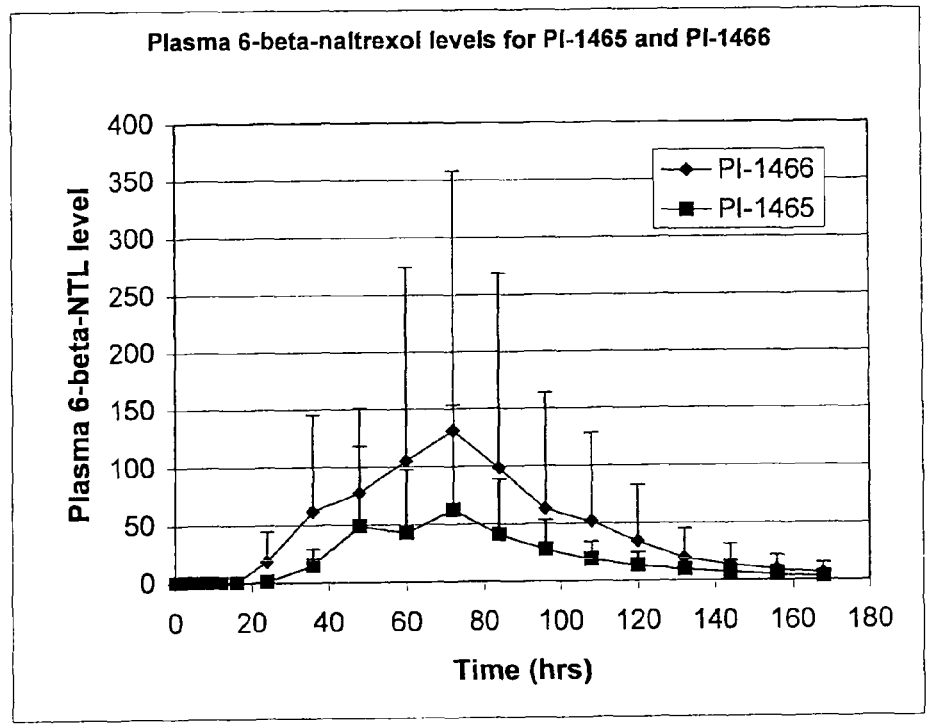
FIG. 15. Plasma 6-beta-naltrexol levels for PI-1465 and PI-1466.

This is a single-dose, open-label, single-period study in which two groups of eight subjects received one dose of either PI-1465 or PI-1466 under fasting condition. Blood samples were drawn prior to dose administration and at 0.5 to 168 hours post-dose. Limits of quantitation are 4.00 pg/mL for naltrexone and 0.250 pg/mL for 6-beta-naltrexol. The data is shown in FIGS. 14-15.

2. Summary of Pharmacokinetics Parameters

|  | 6-beta-Naltrexol | | Naltrexone | |
| --- | --- | --- | --- | --- |
|  | PI-1465 | PI-1466 | PI-1465 | PI-1466 |
| Tmax (hr) | 58.51 | 79.50 | 50.30 (N = 7) | 45.17 (N = 3) |
| Cmax (pg/mL) | 1060 | 72.6 | 139.3 | 46.2 |
| $AUC_{last}$ (pg * h/mL) | 54693 | 23473 | 3713 | 744 |
| AUC∞ (pg * h/mL) | 56260 | 23940 | 7213 (N = 4) | 5943 (N = 2) |
| T½ (hr) | 20.90 | 15.09 | 16.47 (N = 4) | 34.10 (N = 2) |
| Relative Bioavailability to an oral solution (Dose-adjusted) | | | | |
| Cmax Ratio (Test/Solution) | 4.31% | 1.97% | 4.72% | 1.57% |
| $AUC_{last}$ Ratio (Test/Solution) | 26.58% | 11.41% | 41.60% | 8.34% |
| AUC∞ Ratio (Test/Solution) | 26.45% | 11.26% | 75.38% | 62.11% |

N = 8, unless specified otherwise

3. Conclusions a. Presence of surfactant in the dissolution medium (second in-vitro drug release method) provides better in-vitro-in-vivo-correlation than buffer alone (first in-vitro drug release method).

b. Kadian NT pellets (additional layering of NaCl/morphine/Kadian ER coat on top of naltrexone pellets) had a higher release of naltrexone in vivo than Naltrexone pellets alone. PI-1465 containing the seal coat and the same naltrexone pellet coat thickness as PI-1460 from POC without seal coat (90 μm), had more than 5 times more release of naltrexone. Even an increase in Naltrexone pellet coat thickness to 120 μm (PI-1466) still gave twice the release of naltrexone.

D. In-vivo Study #2

Figure 16:
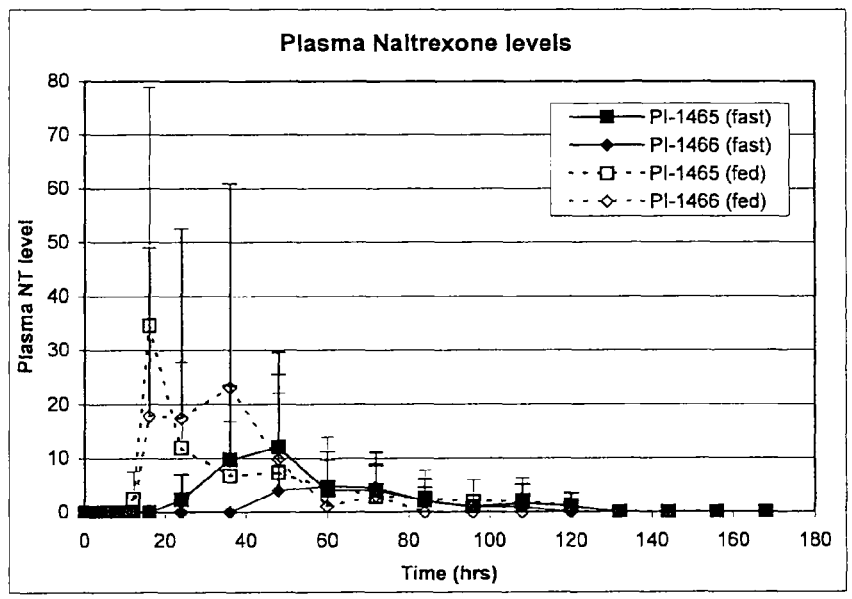
FIG. 16. Plasma naltrexone levels for PI-1465 and PI-1466 (fast and fed).
Figure 17:
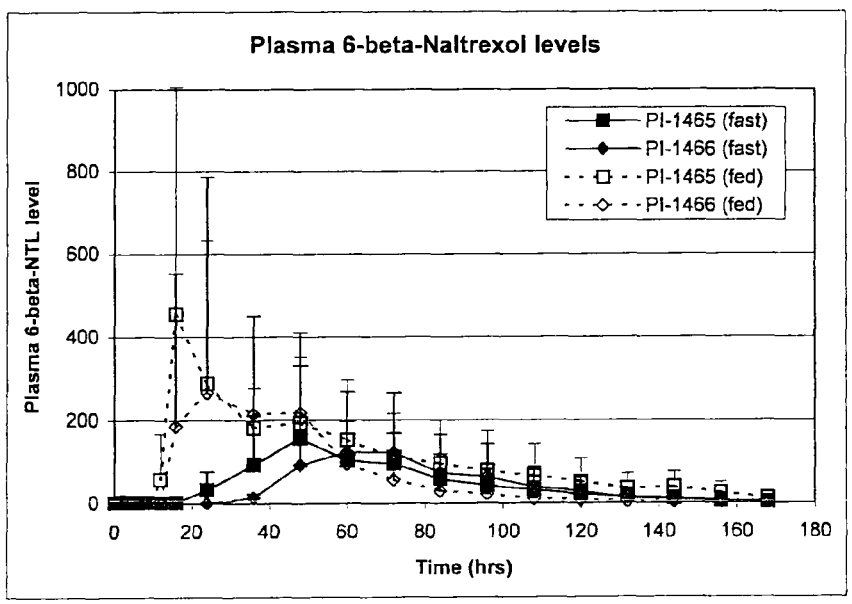
FIG. 17. Plasma 6-beta-naltrexol levels for PI-1465 and PI-1466 (fast and fed).

This is a single-dose, open-label, single-period study in which four groups of four healthy subjects received a single dose of either PI-1465 or PI-1466 under either fasting or fed conditions. Blood samples were drawn prior to dose administration and at 0.5 to 168 hours post-dose. Limits of quantitation are 4.00 pg/mL for naltrexone and 0.250 pg/mL for 6-beta-naltrexol. The data is shown in FIGS. 16-17.

1. Summary of Pharmacokinetic Parameters
a. Naltrexone

|  | PI-1465 | | PI-1466 | |
| --- | --- | --- | --- | --- |
|  | Fast | Fed | Fast | Fed |
| Tmax (hr) | 72.00 | 26.67 (N = 3) | 60.00 (N = 2) | 32.00 (N = 3) |
| Cmax (pg/mL) | 107.3 | 279.3 | 35.73 | 262 |
| $AUC_{last}$ (pg * h/mL) | 2825 | 4135 | 1319 | 4611 |
| AUC∞ (pg * h/mL) | 3593 (N = 1) | 6787 (N = 2) | 3651 (N = 2) | — |
| T½ (hr) | 15.26 (N = 1) | 20.98 (N = 2) | 24.75 (N = 2) | — |
| Relative Bioavailability to an oral solution(Dose-adjusted) | | | | |
| Cmax Ratio (Test/Solution) | 3.64% | 9.47% | 1.21% | 8.89% |
| $AUC_{last}$ Ratio (Test/Solution) | 31.65% | 46.33% | 14.78% | 51.66% |
| AUC∞ Ratio (Test/Solution) | 37.55% | 70.93% | 38.15% | — |

N = 4, unless specified otherwise b. 6-beta-Naltrexol Levels

|  | PI-1465 | | PI-1466 | |
| --- | --- | --- | --- | --- |
|  | Fast | Fed | Fast | Fed |
| Tmax (hr) | 69.00 | 29.00 | 69.00 | 36.00 |
| Cmax (pg/mL) | 1280 | 3787 | 873 | 2680 |
| $AUC_{last}$ (pg * h/mL) | 53307 | 120400 | 47140 | 78533 |
| AUC∞ (pg * h/mL) | 53547 | 122533 | 47920 | 78867 |
| T½ (hr) | 19.21 | 18.17 | 20.69 | 20.19 |
| Relative Bioavailability to an oral solution | | | | |
| Cmax Ratio (Test/Solution) | 5.20% | 15.39% | 3.55% | 10.89% |
| $AUC_{last}$ Ratio (Test/Solution) | 25.90% | 58.50% | 22.91% | 38.16% |
| AUC∞ Ratio (Test/Solution) | 25.17% | 57.61% | 22.53% | 37.08% |

N = 4, unless specified otherwise

2. Conclusion a. There is significant food effect, where the lag time was reduced and NT release was increased in the presence of food. There is a two-fold increase in NT release for PI-1465 and 1.5-fold increase for PI-1466 in the presence of food.

b. There is some subject group variability. Comparing PI-1466 in both in-vivo study #1 and #2, although the same product was used, for fasting condition, there was a two-fold difference in AUC. For PI-1465, the AUC was similar between the two studies.

V. Optimization Study #4, Morphine Sulfate and Naltrexone HCl 60 mg/4.8 mg (20-780-1N)

|  | PI-1495 | | PI-1496 | |
| --- | --- | --- | --- | --- |
|  | mg/unit | Percent | mg/unit | Percent |
| Sealed-coated sugar spheres | | | | |
| Sugar spheres (#25-30 mesh) | 37.2 | 11.7 | 37.1 | 11.9 |
| Ethylcellulose N50 | 6.2 | 1.9 | 6.2 | 2.0 |
| Mag Stearate | 2.5 | 0.8 | 2.5 | 0.8 |
| DBS | 0.6 | 0.2 | 0.6 | 0.2 |
| Talc | 15.5 | 4.9 | 15.5 | 5.0 |
| Subtotal | 62.0 | 19.4 | 61.9 | 19.9 |
| Naltrexone cores | | | | |
| Sealed sugar spheres | (62.0) | (19.4) | (61.9) | (19.9) |
| Naltrexone HCl | 4.8 | 1.50 | 4.8 | 1.54 |
| HPC (Klucel LF) | 0.9 | 0.3 | 0.9 | 0.3 |
| Ascorbic acid | 0.5 | 0.2 | 0.5 | 0.2 |
| Talc | 2.27 | 0.7 | 2.24 | 0.7 |
| Subtotal | 70.5 | 22.1 | 70.3 | 22.6 |

|  | PI-1495 | | PI-1496 | |
| --- | --- | --- | --- | --- |
|  | mg/unit | Percent | mg/unit | Percent |
| Naltrexone pellets | | | | |
| Naltrexone cores | (70.5) | (22.1) | (70.3) | (22.6) |
| Eudragit RS PO | 53.3 | 16.7 | 53.3 | 17.1 |
| SLS | 1.8 | 0.6 | 1.8 | 0.6 |
| DBS | 5.36 | 1.7 | 5.36 | 1.7 |
| Talc | 52.1 | 16.3 | 52.1 | 16.8 |
| Subtotal | 183.0 | 57.4 | 182.9 | 58.8 |
| Naltrexone-morphine cores | | | | |
| Naltrexone pellets | (183.0) | (57.4) | (182.9) | (58.8) |
| Morphine sulfate | 59.9 | 18.8 | 59.7 | 19.2 |
| Sodium chloride | 11.2 | 3.5 |  |  |
| HPC (Klucel LF) | 7.3 | 2.3 | 4.76 | 1.5 |
| HPMC, 3 cps |  |  | 7.6 | 2.4 |
| Subtotal | 261.4 | 82.0 | 255.0 | 82.0 |
| Naltrexone-morphine pellets | | | | |
| Naltrexone-morphine cores | (261.4) | (82.0) | (255.0) | (82.0) |
| Ethylcellulose N50 | 19.81 | 6.2 | 19.31 | 6.2 |
| PEG 6000 | 9.16 | 2.9 | 8.9 | 2.9 |
| Eudragit L100-55 | 4.3 | 1.3 | 4.2 | 1.4 |
| DEP | 4.12 | 1.3 | 4 | 1.3 |
| Talc | 20.13 | 6.3 | 19.62 | 6.3 |
| Total | 319.0 | 100.0 | 311.0 | 100.0 |

A. Method of Preparation—
 1. Dissolve Ethylcellulose and dibutyl sebacate into ethanol, then disperse talc and magnesium stearate into the solution.
 2. Spray the dispersion from 1 onto sugar spheres in a Wurster to form seal-coated sugar spheres (50 μm seal coat).
 3. Dissolve Klucel LF and ascorbic acid into 20:80 mixture of water and ethanol. Disperse naltrexone HCl and talc into the solution.
 4. Spray the naltrexone dispersion from 3 onto seal-coated sugar spheres from 2 in a Wurster to form naltrexone cores.
 5. Dissolve Eudragit RS, sodium lauryl sulfate and dibutyl debacate into ethanol. Disperse talc into the solution.
 6. Spray the dispersion from 5 onto naltrexone cores from 4 in a Wurster to form naltrexone pellets.
 7. The Naltrexone pellets are dried at 50° C. for 48 hours.
 8. Resulting pellets have a Eudragit RS coat thickness of 150 μm for both PI-1495 PI-1496.
 9. (Only for PI-1495) Dissolve sodium chloride and hypromellose into water.
 10. Dissolve hypromellose into 10:90 mixture of water and ethanol. Disperse morphine sulfate into the solution.
 11. (Only for PI-1495) Spray the solution from 9 followed by the dispersion from 10 onto naltrexone pellets in 7 in a rotor to form naltrexone-morphine cores.
 12. (Only for PI-1496) Spray the dispersion from 10 onto naltrexone pellets in 7 in a rotor to form naltrexone-morphine cores.
 13. Dissolve ethylcellulose, PEG 6000, Eudragit L100-55 and diethyl phthalate into ethanol. Disperse talc into the solution.
 14. Spray the dispersion from 12 onto naltrexone-morphine cores in 11 or 12 to form naltrexone-morphine pellets.
 15. The pellets are filled into capsules.

B. In-vitro Drug Release—
 1. Method—USP paddle method at 37° C. and 100 rpm
  1 hour in 0.1N HCl, then 72 hours in 0.05M pH 7.5 phosphate buffer
  Results—Percent of NT released at 73 hours for PI-1495=0%
  Percent of NT released at 73 hours for PI-1496=0%
 2. Method—USP paddle method at 37° C. and 100 rpm
  72 hrs in 0.2% Triton X-100/0.2% sodium acetate/0.002N HCl, pH 5.5
  Results—Percent of NT released at 73 hours for PI-1495=0%
  Percent of NT released at 73 hours for PI-1496=0%

C. In-vivo Study

Figure 18:
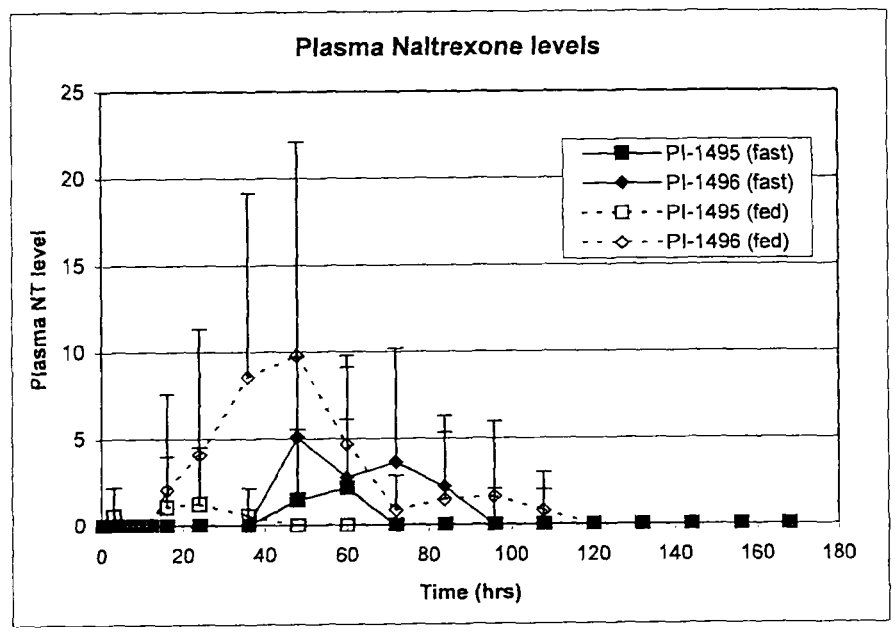
FIG. 18. Plasma naltrexone levels for PI-1495 and PI-1496 (fast and fed).
Figure 19:
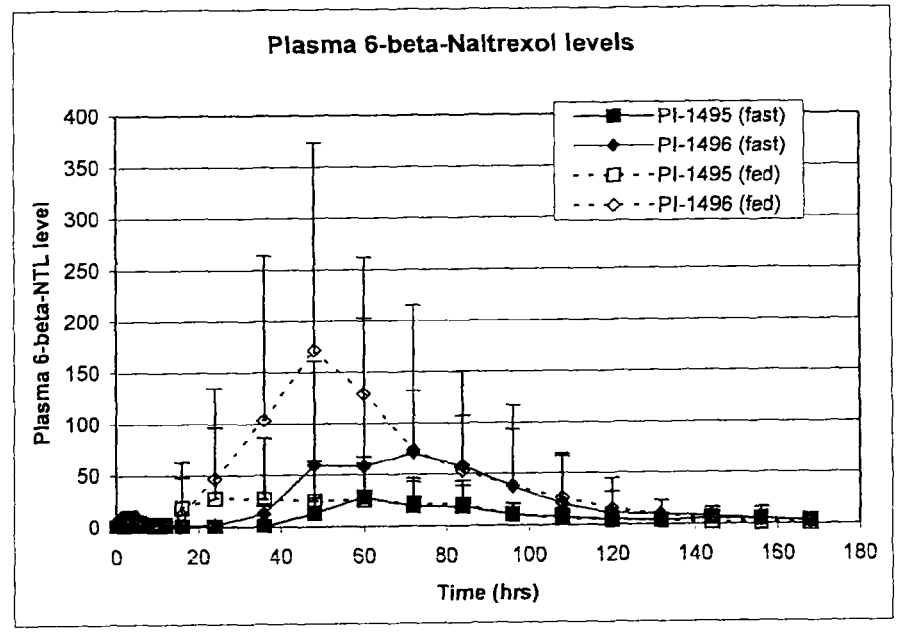
FIG. 19. Plasma 6-beta-naltrexol levels for PI-1495 and PI-1496 (fast and fed).

This is a single-dose, open-label, two period study in which two groups of eight subjects received one dose of either PI-1495 or PI-1496. Each subject received an assigned treatment sequence based on a randomization schedule under fasting and non-fasting conditions. Blood samples were drawn prior to dose administration and at 0.5 to 168 hours post-dose. Limits of quantitation are 4.00 pg/mL for naltrexone and 0.250 pg/mL for 6-beta-naltrexol. The data is shown in FIGS. 18-19.
 2. Summary of Pharmacokinetic Parameters
  a. Naltrexone

|  | PI-1495 | | PI-1496 | |
| --- | --- | --- | --- | --- |
|  | Fast | Fed | Fast | Fed |
| Tmax (hr) | 54.00 (N = 2) | 14.34 (N = 3) | 55.20 (N = 5) | 41.60 (N = 5) |
| Cmax (pg/mL) | 8.53 | 6.32 (N = 7) | 24.23 (N = 7) | 45.67 (N = 7) |
| AUC$_{last}$ (pg * h/mL) | 100.8 | 75.9 (N = 7) | 500.6 (N = 7) | 1265 (N = 7) |
| AUC∞ (pg * h/mL) | — | — | 2105.3 (N = 2) | 3737 (N = 2) |
| T½ (hr) | — | — | 44.56 (N = 2) | 33.17 (N = 2) |
| Relative Bioavailability to an oral solution (Dose-adjusted) | | | | |
| Cmax Ratio (Test/Solution) | 0.29% | 0.21% | 0.82% | 1.55% |
| AUC$_{last}$ Ratio (Test/Solution) | 1.13% | 0.85% | 5.61% | 14.17% |
| AUC∞ Ratio (Test/Solution) | — | — | 22.0% | 39.1% |

N = 8, unless specified otherwise b. 6-beta-Naltrexol Levels

|  | PI-1495 | | PI-1496 | |
| --- | --- | --- | --- | --- |
|  | Fast | Fed | Fast | Fed |
| Tmax (hr) | 69.00 | 41.44 (N = 7) | 70.51 | 67.63 |
| Cmax (pg/mL) | 116.3 | 151.7 (N = 7) | 303.3 | 656.7 |
| $AUC_{last}$ (pg * h/mL) | 5043 | 7332 (N – 7) | 14653 | 27503 |
| $AUC\infty$ (pg * h/mL) | 5607 | 8449 (N = 6) | 14930 | 27827 |
| $T^{1/2}$ (hr) | 20.97 | 16.69 (N = 7) | 16.29 | 22.59 |
| Relative Bioavailability to an oral solution (Dose-adjusted) | | | | |
| Cmax Ratio (Test/Solution) | 0.47% | 0.62% | 1.23% | 2.67% |
| $AUC_{last}$ Ratio (Test/Solution) | 2.45% | 3.45% | 7.12% | 13.36% |
| $AUC\infty$ Ratio (Test/Solution) | 2.64% | 3.97% | 7.02% | 13.08% |

N = 8, unless specified otherwise

3. Conclusion
   a. Kadian NT pellets with naltrexone pellet coat thickness of 150 μm had comparable naltrexone release as NT pellets with 90 μm coat thickness. This comparable NT release may also be attributed from the presence of 50 μm seal coat on the sugar spheres used in Kadian NT pellets.
   b. Significant NT sequestering was observed, both at fasting (>97%) and fed states (>96%).
   c. Kadian NT pellets containing sodium chloride immediately above the naltrexone pellet coat (PI-1495) had half the release of naltrexone compared to Kadian NT pellet without sodium chloride (PI-1496), consistent with in vitro results.
   d. There is again food effect observed. Lag time was significantly reduced.

VI. Optimization Study #5, Morphine Sulfate and Naltrexone HCl 60 mg/2.4 mg (20-903-AU)

|  | PI-1510 | |
| --- | --- | --- |
|  | mg/unit | Percent |
| Sealed sugar spheres | | |
| Sugar spheres (#25-30 mesh) | 39.9 | 12.2 |
| Ethylcellulose N50 | 6.5 | 2.0 |
| Mag Stearate | 2.6 | 0.8 |
| DBS | 0.7 | 0.2 |
| Talc | 16.7 | 5.1 |
| Subtotal | 66.4 | 20.3 |
| Naltrexone cores | | |
| Sealed sugar spheres | (66.4) | (20.3) |
| Naltrexone HCl | 2.4 | 0.73 |
| HPC (Klucel LF) | 0.5 | 0.1 |
| Ascorbic acid | 0.2 | 0.1 |
| Talc | 1.1 | 0.4 |
| Subtotal | 70.6 | 21.6 |
| Naltrexone pellets | | |
| Naltrexone cores | (70.6) | (21.6) |
| Eudragit RS PO | 53.0 | 16.2 |
| SLS | 1.8 | 0.6 |
| DBS | 5.3 | 1.6 |
| Talc | 53.0 | 16.2 |
| Subtotal | 183.7 | 56.2 |
| Naltrexone-morphine cores | | |
| Naltrexone pellets | (183.7) | (56.2) |
| Morphine sulfate | 60.1 | 18.4 |
| Sodium chloride | 12.5 | 3.8 |
| HPC (Klucel LF) | 6.2 | 1.9 |
| Subtotal | 262.4 | 80.2 |
| Naltrexone-morphine pellets | | |
| Naltrexone-morphine cores | (262.4) | (80.2) |
| Ethylcellulose N50 | 22.9 | 7.0 |
| PEG 6000 | 10.6 | 3.2 |
| Eudragit L100-55 | 5.0 | 1.5 |
| DEP | 4.7 | 1.5 |
| Talc | 21.5 | 6.6 |
| Total | 327.1 | 100.0 |

B. Method of Preparation—
   1. Dissolve Ethylcellulose and dibutyl sebacate into ethanol, then disperse talc and magnesium stearate into the solution.
   2. Spray the dispersion from 1 onto sugar spheres in a Wurster to form seal-coated sugar spheres (50 μm seal coat).
   3. Dissolve Klucel LF and ascorbic acid into 20:80 mixture of water and ethanol. Disperse naltrexone HCl and talc into the solution.
   4. Spray the naltrexone dispersion from 3 onto seal-coated sugar spheres from 2 in a Wurster to form naltrexone cores.
   5. Dissolve Eudragit RS, sodium lauryl sulfate and dibutyl sebacate into ethanol. Disperse talc into the solution.
   6. Spray the dispersion from 5 onto naltrexone cores from 4 in a Wurster to form naltrexone pellets.
   7. The Naltrexone pellets are dried at 50° C. for 48 hours.
   8. Resulting pellets have a Eudragit RS coat thickness of 150 μm.
   9. Dissolve sodium chloride and hypromellose into water.
   10. Dissolve hypromellose into 10:90 mixture of water and ethanol. Disperse morphine sulfate into the solution.
   11. Spray the solution from 9 followed by the dispersion from 10 onto naltrexone pellets in 7 in a rotor to form naltrexone-morphine cores.
   12. Dissolve ethylcellulose, PEG 6000, Eudragit L100-55 and diethyl phthalate into ethanol. Disperse talc into the solution.

13. Spray the dispersion from 12 onto naltrexone-morphine cores in 11 or 12 to form naltrexone-morphine pellets.
14. The pellets are filled into capsules.

B. In-vitro Drug Release—
  1. Method—USP paddle method at 37° C. and 100 rpm 1 hour in 0.1N HCl, then 72 hours in 0.05M pH 7.5 phosphate buffer
  Results—Percent of NT released at 73 hours for =0%
  2. Method—USP paddle method at 37° C. and 100 rpm 72 hrs in 0.2% Triton X-100/0.2% sodium acetate/ 0.002N HCl, pH 5.5
  Results—Percent of NT released at 73 hours=0%

C. In-vivo Study

Figure 20:
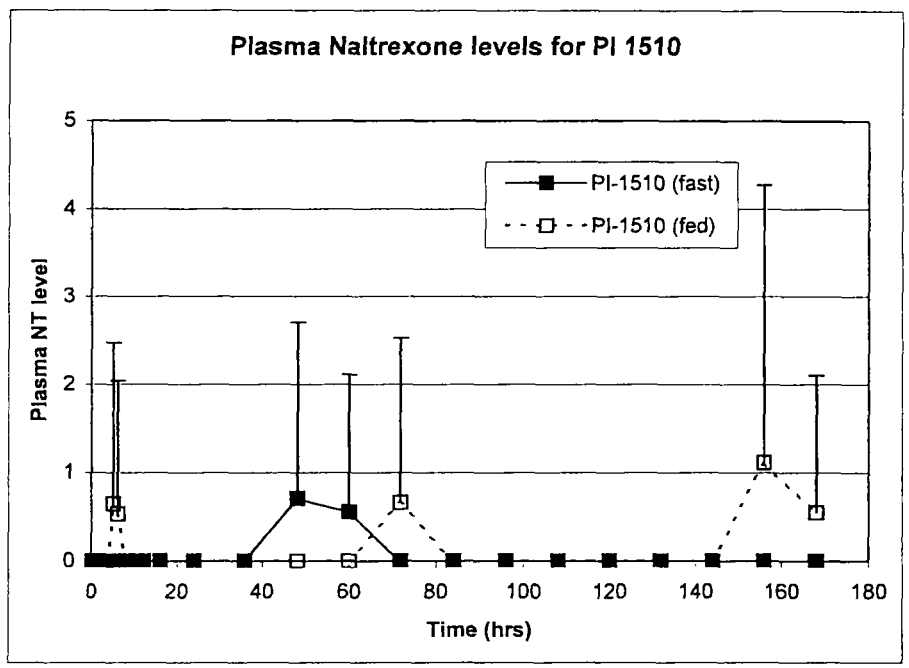
FIG. 20. Plasma naltrexone levels for PI-1510 (fast and fed).
Figure 21:
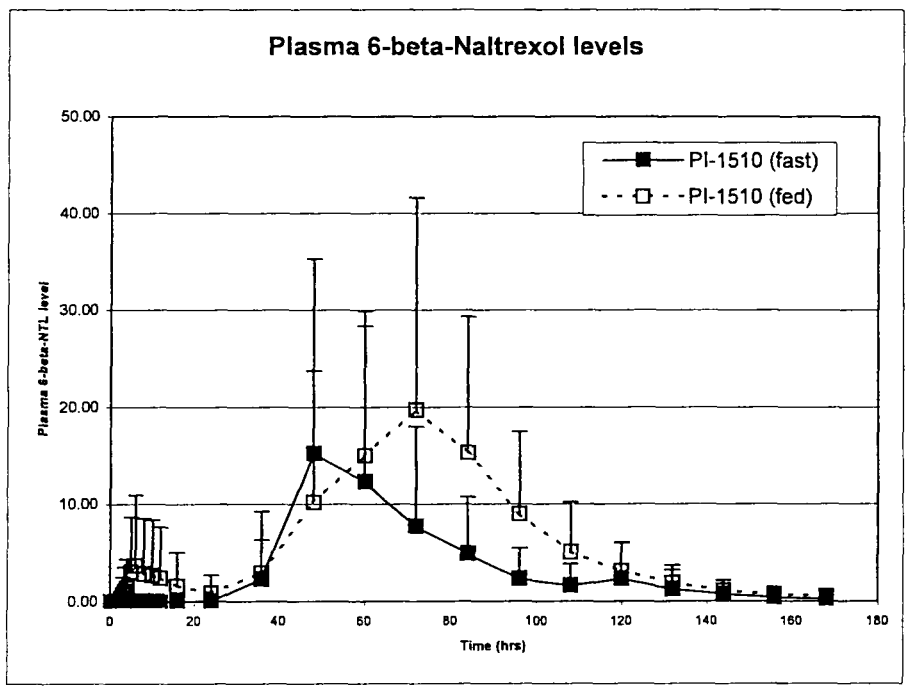
FIG. 21. Plasma 6-beta-naltrexol levels for PI-1510 (fast and fed).

This is a single-dose, open-label, two period study in which eight subjects were randomized to receive one dose of PI-1510 under either fasted or fed state during Study Period 1 and alternate fasted or fed state for Study Period 2. Blood samples were drawn prior to dose administration and at 0.5 to 168 hours post-dose. Limits of quantitation are 4.00 pg/mL for naltrexone and 0.250 pg/mL for 6-beta-naltrexol. The data is shown in FIGS. 20 and 21.

2. Summary of Pharmacokinetic Parameters
    a. 6-beta-Naltrexol Levels

|  | PI-1510 | |
| --- | --- | --- |
|  | Fast | Fed |
| Tmax (hr) | 45.00 (N = 6) | 57.29 (N = 7) |
| Cmax (pg/mL) | 16.1 | 25.0 |
| $AUC_{last}$ (pg * h/mL) | 609.2 | 1057 |
| AUC∞ (pg * h/mL) | 1233 | 1431 (N = 6) |
| T½ (hr) | 17.36 | 17.48 (N = 6) |
| Relative Bioavailability to an oral solution (Dose-adjusted) | | |
| Cmax Ratio (Test/Solution) | 0.44% | 0.68% |
| $AUC_{last}$ Ratio (Test/Solution) | 1.97% | 3.42% |
| AUC∞ Ratio (Test/Solution) | 3.86% | 4.49% |

N = 8, unless specified otherwise

3. Conclusion
    a. PI-1510 and PI-1495 are comparable. The reduction in naltrexone loading in the pellets (from 1.5% in PI-1495 to 0.7% in PI-1510) does not seem to affect NT release.
    b. Significant NT sequestering was observed, both at fasting (>96%) and fed states (>95%).
    c. The food effect observed was modest in terms of total NT release. However, the lag time was significantly reduced in the presence of food. There were subjects with multiple peaks of release.

VII. Summary of NT Release from All in-vivo Studies

BA (Cmax)=Relative bioavailability based on Cmax=Dose-adjusted ratio of Cmax (NT/KNT pellet) to Cmax(NT soln)
BA (AUC last)=Relative bioavailability based on AUC last=Dose-adjusted ratio of AUC last (NT/KNT pellet) to AU
BA (AUC inf)=Relative bioavailability based on AUC inf=Dose-adjusted ratio of AUC inf (NT/KNT pellet)
Total in-vivo cumulative NT release can be extrapolated from BA (AUC inf) calculations from 6-beta-Naltrexol plasma levels

|  | BA (Cmax) (%) | BA (AUC last) (%) | BA (AUC inf) (%) |
| --- | --- | --- | --- |
| POC | | | |
| PI-1460 Fast | | | |
| Avg ± SD | 1.2 ± 0.9 | 5.1 ± 3.1 | |
| Range | 0.32-2.99 | 1.92-10.65 | |
| PI-1461 Fast | | | |
| Avg ± SD | 3.1 ± 2.4 | 15.8 ± 11.9 | |
| Range | 0.7-10.3 | 2.8-49.2 | |
| OPTIM. #1 | | | |
| PI-1462 Fast | | | |
| Avg ± SD | 9.5 ± 2.8 | 54.6 ± 21.0 | 53.4 ± 20.6 |
| Range | 5.7-13.0 | 26.3-86.3 | 25.6-84.4 |
| PI-1463 Fast | | | |
| Avg ± SD | 7.7 ± 3.7 | 36.1 ± 18.2 | 35.0 ± 17.7 |
| Range | 0.8-12.4 | 3.9-59.2 | 3.8-57.3 |
| OPTIM. #2 and #3 | | | |
| PI-1465 Fast 1 | | | |
| Avg ± SD | 4.3 ± 6.2 | 26.6 ± 35.4 | 26.4 ± 35.0 |
| Range | 0.1-18.6 | 0.1-111.6 | 0.1-110.5 |
| Fast 2 | | | |
| Avg ± SD | 5.2 ± 3.9 | 25.9 ± 15.7 | 25.2 ± 15.2 |
| Range | 1.8-10.5 | 9.6-41.5 | 9.4-40.2 |
| Fed | | | |
| Avg ± SD | 15.4 ± 12.5 | 58.5 ± 34.6 | 57.6 ± 34.4 |
| Range | 1.4-31.2 | 11.9-90.6 | 11.5-90.6 |
| PI-1466 Fast 1 | | | |
| Avg ± SD | 2.0 ± 2.3 | 11.4 ± 11.8 | 11.3 ± 11.4 |
| Range | 0.2-5.9 | 1.1-30.0 | 11.1-29.1 |
| Fast 2 | | | |
| Avg ± SD | 3.6 ± 3.9 | 22.9 ± 25.6 | 22.5 ± 24.9 |
| Range | 0.5-8.6 | 1.8-57.4 | 1.8-56.1 |
| Fed | | | |
| Avg ± SD | 10.9 ± 12.7 | 38.2 ± 40.0 | 37.1 ± 38.9 |
| Range | 0.3-28.5 | 1.7-90.3 | 1.6-87.7 |
| OPTIM. #4 | | | |
| PI-1495 Fast | | | |
| Avg ± SD | 0.5 ± 0.5 | 2.5 ± 2.3 | 2.6 ± 2.4 |
| Range | 0.1-1.4 | 5.9-0.3 | 0.3-5.7 |
| Fed | | | |
| Avg ± SD | 3.0 ± 6.7 | 10.2 ± 19.4 | 11.3 ± 20.0 |
| Range | 0.1-19.4 | 0.2-57.0 | 0.2-55.4 |
| Fed (-Subject 1) | | | |
| Avg ± SD | 0.6 ± 0.9 | 3.6 ± 4.9 | 4.0 ± 5.0 |
| Range | 0.1-2.5 | 0.2-13.8 | 0.2-13.4 |
| PI-1496 Fast | | | |
| Avg ± SD | 1.2 ± 0.9 | 7.1 ± 4.6 | 7.0 ± 4.6 |
| Range | 0.1-2.7 | 0.6-14.2 | 0.6-14.5 |
| Fed | | | |
| Avg ± SD | 2.7 ± 2.9 | 13.4 ± 12.6 | 13.1 ± 12.3 |
| Range | 0.1-7.6 | 0.1-31.6 | 0.4-30.7 |
| OPTIM. #5 | | | |
| PI-1510 Fast | | | |
| Avg | 0.4 | 2.0 | 3.9 |
| Fed | | | |
| Avg | 0.7 | 3.4 | 4.5 |

While the present invention has been described in terms of the preferred embodiments, it is understood that variations and modifications will occur to those skilled in the art. Therefore, it is intended that the appended claims cover all such equivalent variations that come within the scope of the invention as claimed.

The invention claimed is:

1. A composition comprising a plurality of multi-layer pellets comprising:
   a. a water-soluble core;
   b. an opioid antagonist comprising layer coating the core, wherein the opioid antagonist is selected from the group consisting of naltrexone, naloxone, nalmefene, cyclazacine, levallorphan, salts of these molecules, and combinations thereof;
   c. a sequestering polymer layer coating the opioid antagonist comprising layer;
   d. an osmotic pressure regulating agent comprising layer coating the sequestering polymer layer, wherein the osmotic pressure regulating agent is selected from the group consisting of sodium chloride, sodium bromide, sodium iodide, hydroxypropyl methyl cellulose, and combinations thereof;
   wherein the sequestering polymer layer comprises
   copolymers of acrylic and methacrylic acid esters with quaternary ammonium groups,
   a surfactant in an amount from 1.6% to 6.3% of the copolymers of acrylic and methacrylic acid esters with quaternary ammonium groups on a weight-to-weight basis, and
   talc in an amount of from 75% to 125% of the copolymers of acrylic and methacrylic acid esters with quaternary ammonium groups on a weight-to-weight basis; and
   wherein the surfactant is selected from the group consisting of sodium lauryl sulfate, sodium docusate, dioctyl sodium sulphosuccinate, sodium lauryl sarcosinate, sodium methyl cocyl taurate, magnesium lauryl sulfate, dioctyl sodiumsulfosuceinate, sodiumdodecylbenzene sulfonate, and combinations thereof.

2. The composition of claim 1, wherein the surfactant is not comprised in the following:
   the water-soluble core,
   the opioid antagonist comprising layer,
   the osmotic pressure regulating agent comprising layer,
   the opioid agonist comprising layer, and
   the controlled release layer.

3. The composition of claim 1, wherein when tested by a testing method, the composition sequesters at least 80% of the opioid antagonist as determined at 73 hours from the start of the testing method,
   wherein the testing method consists of first placing the composition in 500 mL of a 0.1 N HCl solution for 1 hour at 37° C. using USP paddle method, 100 rotations per minute, and then placing the composition in 500 mL of a pH 7.5, 0.05 M phosphate buffer, for 72 hours at 37° C. using USP paddle method, 100 rotations per minute, and then determining the amount of the opioid antagonist sequestered.

4. The composition of claim 1, wherein the surfactant is not comprised in the following:
   the water-soluble core,
   the opioid antagonist comprising layer,
   the osmotic pressure regulating agent comprising layer, and
   wherein when tested by a testing method, the composition sequesters at least 80% of the opioid antagonist as determined at 73 hours from the start of the testing method,
   wherein the testing method consists of first placing the composition in 500 mL of a 0.1 N HCl solution for 1 hour at 37° C. using USP paddle method, 100 rotations per minute, and then placing the composition in 500 mL of a pH 7.5, 0.05 M phosphate buffer, for 72 hours at 37° C. using USP paddle method, 100 rotations per minute, and then determining the amount of the opioid antagonist sequestered.

5. The composition of claim 1,
   wherein the osmotic pressure regulating agent comprises sodium chloride;
   wherein the surfactant is sodium lauryl sulfate; and
   wherein when tested by a testing method, the composition sequesters at least 80% of the salt of the opioid antagonist as determined at 73 hours from the start of the testing method,
   wherein the testing method consists of first placing the composition in 500 mL of a 0.1 N HCl solution for 1 hour at 37° C. using USP paddle method, 100 rotations per minute, and then placing the composition in 500 mL of a pH 7.5, 0.05 M phosphate buffer, for 72 hours at 37° C. using USP paddle method, 100 rotations per minute, and then determining the amount of the opioid antagonist sequestered.

6. The composition of claim 1,
   wherein the opioid antagonist is the salt of naltrexone;
   wherein the osmotic pressure regulating agent comprises sodium chloride;
   wherein the surfactant is sodium lauryl sulfate;
   wherein the opioid agonist comprising layer comprises morphine sulfate and further comprises hydroxypropyl cellulose; and
   wherein when tested by a testing method, the composition sequesters at least 80% of the salt of naltrexone as determined at 73 hours from the start of the testing method,
   wherein the testing method consists of first placing the composition in 500 mL of a 0.1 N HCl solution for 1 hour at 37° C. using USP paddle method, 100 rotations per minute, and then placing the composition in 500 mL of a pH 7.5, 0.05 M phosphate buffer, for 72 hours at 37° C. using USP paddle method, 100 rotations per minute, and then determining the amount of the salt of naltrexone sequestered.

7. The composition of claim 1,
   wherein the opioid antagonist is naltrexone HCl;
   wherein the osmotic pressure regulating agent comprises sodium chloride;
   wherein the surfactant is sodium lauryl sulfate; and
   wherein when tested by a testing method, the composition sequesters at least 80% of the naltrexone HCl as determined at 73 hours from the start of the testing method,
   wherein the testing method consists of first placing the composition in 500 mL of a 0.1 N HCl solution for 1 hour at 37° C. using USP paddle method, 100 rotations per minute, and then placing the composition in 500 mL of a pH 7.5, 0.05 M phosphate buffer, for 72 hours at 37° C. using USP paddle method, 100 rotations per minute, and then determining the amount of the naltrexone HCl sequestered.

8. The composition of claim 1,
   wherein the opioid antagonist is naltrexone HCl; and
   wherein the surfactant is sodium lauryl sulfate.

9. The composition of claim 1,
   wherein the opioid antagonist is naltrexone HCl;
   wherein the surfactant is sodium lauryl sulfate. and
   wherein the osmotic pressure regulating agent comprises sodium bromide.

10. The composition of claim 1,
wherein the opioid antagonist is naltrexone HCl;
wherein the surfactant is sodium lauryl sulfate; and
wherein the osmotic pressure regulating agent comprises sodium iodide.

11. The composition of claim 1,
wherein the opioid antagonist is naltrexone HCl;
wherein the surfactant is sodium lauryl sulfate; and
wherein the osmotic pressure regulating agent comprises hydroxypropyl methyl cellulose.

12. The composition of claim 1, wherein the composition does not comprise a bittering agent, a gelling agent, an irritant, or an emetic.

13. The composition of claim 1, wherein opioid antagonist is not comprised in the following:
the water-soluble core,
the sequestering polymer layer, and
the osmotic pressure regulating agent comprising layer.

14. A composition comprising a plurality of multi-layer pellets comprising:
a. a water-soluble core;
b. an opioid antagonist comprising layer coating the core, wherein the opioid antagonist is selected from the group consisting of naltrexone, naloxone, nalmefene, cyclazacine, levallorphan, salts of these molecules, and combinations thereof;
c. a sequestering polymer layer coating the opioid antagonist comprising layer;
d. an osmotic pressure regulating agent comprising layer coating the sequestering polymer layer, wherein the osmotic pressure regulating agent is selected from the group consisting of sodium chloride, sodium bromide, sodium iodide, hydroxypropyl methyl cellulose, and combinations thereof;
e. an opioid agonist comprising layer coating the osmotic pressure regulating agent comprising layer, wherein the opioid agonist is selected from the group consisting of oxycodone, a salt of oxycodone, and combinations thereof; and
f. a controlled release layer coating the opioid agonist comprising layer;
wherein the sequestering polymer layer comprises
copolymers of acrylic and methacrylic acid esters with quaternary ammonium groups,
a surfactant in an amount from 1.6% to 6.3% of the copolymers of acrylic and methacrylic acid esters with quaternary ammonium groups on a weight-to-weight basis, and
talc in an amount of from 75% to 125% of the copolymers of acrylic and methacrylic acid esters with quaternary ammonium groups on a weight-to-weight basis; and
wherein the surfactant is selected from the group consisting of sodium lauryl sulfate, sodium docusate, dioctyl sodium sulphosuccinate, sodium lauryl sarcosinate, sodium methyl cocyl taurate, magnesium lauryl sulfate, dioctyl sodiumsulfosuceinate, sodiumdodecylbenzene sulfonate, and combinations thereof.

15. The composition according to any of claim 1, 2, 3, 4, 5, 6, 7, 8, 9, 10, 11, 12, 13, or 14 which further comprises an opioid agonist selected from the group consisting of morphine, oxycodone, hydrocodone, hydromorphone, dihydrocodeine, codeine, dihydromorphine, buprenorphine, salts of these molecules, and combinations thereof.

16. The composition according to claim 15 in which said agonist is morphine or a pharmaceutically acceptable salt thereof.

\* \* \* \* \*